(12) United States Patent
Takamori et al.

(10) Patent No.: US 10,947,190 B2
(45) Date of Patent: Mar. 16, 2021

(54) METHOD FOR PRODUCING OXIDATION REACTION PRODUCT OF HYDROCARBON OR DERIVATIVE THEREOF, AND METHOD FOR PRODUCING OXIDATION REACTION PRODUCT OF OLEFIN

(71) Applicants: ACENET INC., Tokyo (JP); OSAKA UNIVERSITY, Suita (JP)

(72) Inventors: Kiyoto Takamori, Tokyo (JP); Takekatsu Shibata, Tokyo (JP); Kei Ohkubo, Osaka (JP)

(73) Assignees: ACENET INC., Tokyo (JP); Osaka University, Osaka (JP)

( * ) Notice: Subject to any disclaimer, the term of this patent is extended or adjusted under 35 U.S.C. 154(b) by 455 days.

(21) Appl. No.: 16/063,103

(22) PCT Filed: Dec. 16, 2016

(86) PCT No.: PCT/JP2016/087540
§ 371 (c)(1),
(2) Date: Jun. 15, 2018

(87) PCT Pub. No.: WO2017/104798
PCT Pub. Date: Jun. 22, 2017

(65) Prior Publication Data
US 2020/0377453 A1    Dec. 3, 2020

(30) Foreign Application Priority Data

Dec. 18, 2015  (JP) .............................. JP2015-248070
Mar. 4, 2016   (JP) .............................. JP2016-042137
Mar. 4, 2016   (JP) .............................. JP2016-042138
Mar. 4, 2016   (JP) .............................. JP2016-042139
Mar. 4, 2016   (JP) .............................. JP2016-042140

(51) Int. Cl.

| | | |
|---|---|---|
| C07C 407/00 | (2006.01) | |
| C07C 29/00 | (2006.01) | |
| C07C 45/28 | (2006.01) | |
| C07C 51/00 | (2006.01) | |
| C07C 31/04 | (2006.01) | |
| C07C 47/04 | (2006.01) | |
| C07C 53/02 | (2006.01) | |
| C07C 51/16 | (2006.01) | |
| C07C 29/48 | (2006.01) | |
| C07C 409/04 | (2006.01) | |

(52) U.S. Cl.
CPC .......... *C07C 407/003* (2013.01); *C07C 29/48* (2013.01); *C07C 45/28* (2013.01); *C07C 51/16* (2013.01); *C07C 31/04* (2013.01); *C07C 47/04* (2013.01); *C07C 53/02* (2013.01); *C07C 409/04* (2013.01)

(58) Field of Classification Search
CPC ..... C07C 407/003; C07C 29/48; C07C 45/28; C07C 51/46
See application file for complete search history.

(56) References Cited

U.S. PATENT DOCUMENTS

| | | |
|---|---|---|
| 4,208,536 A | 6/1980 | Costantini et al. |
| 4,549,025 A | 10/1985 | Dalcanale et al. |
| 2013/0287722 A1 | 10/2013 | Uhlmann |

FOREIGN PATENT DOCUMENTS

| | | |
|---|---|---|
| JP | 46-006045 B1 | 2/1971 |
| JP | 52-089625 | 7/1977 |
| JP | 60-139628 | 7/1985 |
| JP | 61-005039 | 1/1986 |
| JP | 62-195339 | 8/1987 |
| JP | 1-096143 | 4/1989 |
| JP | 2001-079417 | 3/2001 |
| JP | 2002-263502 | 9/2002 |
| JP | 2014-503457 | 2/2014 |

OTHER PUBLICATIONS

Jeffrey R. Long et al., "Oxidation of ethane to ethanol by N2O in a metalorganic framework with coordinatively unsaturated iron (II) sites", Nature Chemistry, 2014, vol. 6, pp. 590-595.

Georg Süss-Fink et al., "Hydrogen Peroxide Oxygenation of Alkanes Including Methane and Ethane Catalyzed by Iron Complexes in Acetonitrile", Advanced Synthesis & Catalysis, 2004, vol. 346, Issue 2-3, p. 317.

I. Bertini, H. B. Gray, S. J. Lippard, J. S. Valentine, "Bioinorganic Chemistry", University Science Books, California (1994).

S. J. Lippard, J. M. Berg, "Principles of Bioinorganic Chemistry", University Science Books, California (1994)—Abstract Drily.

Ishii et al., "Alkane Oxidation with Air Catalyzed by Lipophilic N-Hydroxyphthalimides without Any Solvent", The Journal of Organic Chemistry, 2001, vol. 66, No. 23, pp. 7889-7891.

Ohkubo et al., "Metal-free oxygenation of cyclohexane with oxygen catalyzed by 9-mesityl-10-methylacridinium and hydrogen chloride under visible light irradiation", Chemical Communications, 2011, vol. 47, pp. 8515-8517.

M. Schröder, "Osmium tetraoxide cis hydroxylation of unsaturated substrates", Chemical Reviews, 1980, vol. 80, No. 2, pp. 187-213.

(Continued)

*Primary Examiner* — Sikarl A Witherspoon
(74) *Attorney, Agent, or Firm* — Hamre, Schumann, Mueller & Larson, P.C.

(57) ABSTRACT

The first aspect of the present invention is intended to provide a method for producing an oxidation reaction product of the hydrocarbon or a derivative thereof efficiently using hydrocarbon or a derivative thereof as a raw material. In order to achieve the above object, the first aspect of the present invention provides a method for producing an oxidation reaction product of a hydrocarbon or a derivative thereof. The method includes the step of irradiating a reaction system with light in the presence of a raw material and a chlorine dioxide radical. The raw material is hydrocarbon or a derivative thereof, the reaction system is a reaction system containing an organic phase, and the organic phase contains the raw material and the chlorine dioxide radical. In the step of irradiating a reaction system with light, the raw material is oxidized by the light irradiation to generate an oxidation reaction product of the raw material.

20 Claims, 11 Drawing Sheets

(56) References Cited

OTHER PUBLICATIONS

E. N. Jacobsen et al., "Asymmetric Dihydroxylation via Ligand-Accelerated Catalysis", Journal of the American Chemical Society, 1988, vol. 110, No. 6, pp. 1968-1970.

S. G. Hentges et al., "Asymmetric induction in the reaction of osmium tetroxide with olefins", Journal of the American Chemical Society, 1980, vol. 102, No. 12, pp. 4263-4265.

Wensheng Yu et al., "Improved Procedure for the Oxidative Cleavage of Olefins by OsO4-NaIO4", Organic Letters, 2004, vol. 6, No. 19, pp. 3217-3219.

A. J. DelMonte et al., "Experimental and Theoretical Kinetic Isotope Effects for Asymmetric Dihydroxylation. Evidence Supporting a Rate-Limiting "(3+2)" Cycloaddition", Journal of the American Chemical Society, 1997, vol. 119, No. 41, pp. 9907-9908.

J. S. M. Wai et al., "A mechanistic insight leads to a greatly improved osmium-catalyzed asymmetric dihydroxylation process", Journal of the American Chemical Society, 1989, vol. 111, No. 3, pp. 1123-1125.

S. Kobayashi et al., "Catalytic Asymmetric Dihydroxylation of Olefins Using a Recoverable and Reusable Polymer-Supported Osmium Catalyst", Journal of the American Chemical Society, 1999, vol. 121, No. 48, pp. 11229-11230.

S. Kobayashi et al., "Catalytic Asymmetric Dihydroxylation Using Phenoxyethoxymethyl-polystyrene (PEM)-Based Novel Microencapsulated Osmium Tetroxide (PEM-MC OsO4)", Organic Letters, 2001, vol. 3, No. 17, pp. 2649-2652.

Hartmuth C. Kolb et al., "Toward an Understanding of the High Enantioselectivity in the Osmium-Catalyzed Asymmetric Dihydroxylation (AD). 1. Kinetics", Journal of the American Chemical Society, 1994, vol. 116, No. 4, pp. 1278-1291.

E. J. Corey et al., "A Critical Analysis of the Mechanistic Basis of Enantioselectivity in the Bis-Cinchona Alkaloid Catalyzed Dihydroxylation of Olefins", Journal of the American Chemical Society, 1996, vol. 118, No. 45, pp. 11038-11053.

Sandra. Y. Jonsson et al., "Osmium-Catalyzed Asymmetric Dihydroxylation of Olefins by H2O2 Using a Biomimetic Flavin-Based Coupled Catalytic System", Journal of the American Chemical Society, 2001, vol. 123, No. 7, pp. 1365-1371.

H. Dodgen et al., "The Exchange of Chlorine Dioxide with Chlorite Ion and with Chlorine in Other Oxidation States", Journal of the American Chemical Society, 1949, vol. 71, No. 7, pp. 2501-2504.

Jessica K. Leigh et al., "Kinetics and Mechanism of Styrene Epoxidation by Chlorite: Role of Chlorine Dioxide", Inorganic Chemistry, 2014, vol. 53, pp. 6715-6727.

Latshaw, "Chlorine dioxide: effective, broad-spectrum biocide for white-water systems", Tappi Journal, 1994, vol. 78, No. 4, pp. 163-166.

J. J. Leddy, "Salt, Chlor-Alkali and Related Heavy Chemicals", Riegel's Handbook of Industrial Chemistry, 8th edn. Ed., J. A. Kent, Van Nostrand Reinhold Co. Inc., New York, 1983, pp. 212-235.

I. Fábián, "The reactions of transition metal ions with chlorine (III)", Coordination Chemistry Review s , 2001, vol. 216-217, pp. 449-472.

Kohda, Akira et al., "Metal-Catalyzed Organic Photoreactions. Bond-Cleavage Selectivity and Synthetic Application of the Iron (III) Chloride Catalyzed Photooxidation of Cyclic Olefins", The Journal of Organic Chemistry., 1983, vol. 48, pp. 425-432—Front page only.

Office Action of the corresponding Japanese Patent Application (No. 2016-042137) dated Jun. 15, 2016—machine translation.

Niwa et al., "A One-Step Conversion of Benzene to Phenol with a Palladium Membrane", Science, 2002, vol. 295, pp. 105-107.

Iwasawa et al., "Direct Phenol Synthesis by Selective oxidation of Benzene with Molecular Oxygen on an Interstitial-N/Re Cluster/Zeolite Catalyst", Angewandte Chemie International Edition, 2006, vol. 45, pp. 448-452.

Ogawa et al., "Efficient Visible-Light-Induced Photocatalytic Activity on Gold-Nanoparticle-Supported Layered Titanate", Journal of the American Chemical Society, 2010, vol. 132, pp. 16762-16764.

METHOD FOR PRODUCING OXIDATION REACTION PRODUCT OF HYDROCARBON OR DERIVATIVE THEREOF, AND METHOD FOR PRODUCING OXIDATION REACTION PRODUCT OF OLEFIN

TECHNICAL FIELD

The present invention relates to a method for producing an oxidation reaction product of a hydrocarbon or a derivative thereof and a method for producing an oxidation reaction product of an olefin.

BACKGROUND ART

Background Art of First Aspect of Invention

Alcohols, carboxylic acids, and the like, which are of great use in industrial application, are produced industrially by various methods. For example, as a method for producing methanol, a method of reacting carbon monoxide obtained by partial combustion of hydrocarbon with hydrogen gas at a high temperature and a high pressure is commonly used. Carbon monoxide and hydrogen gas, which are raw materials, can be produced, for example, by partial combustion of methane (natural gas), steam reforming, and the like. Also, alcohol, carboxylic acid, and the like are commonly produced by a biochemical method such as fermentation.

Furthermore, in these years, for the effective use of natural gas such as shale gas, a method is proposed for producing an oxidation reaction product such as alcohol by oxidizing hydrocarbon contained in natural gas. As a method for producing an oxidation reaction product by a vapor phase reaction, for example, there is a method for producing ethanol by oxidizing ethane by dinitrogen monoxide in the presence of an iron catalyst (Non Patent Literature 1). As a method for producing an oxidation reaction product by a liquid phase reaction, there is a method for producing methanol by oxidizing methane by hydrogen peroxide in an acetonitrile solvent in the presence of an iron catalyst (Non Patent Literature 2).

Background Art of Second Aspect of Invention

Alcohol, carboxylic acid, and the like, which are of great use in industrial application, are produced industrially by various methods. For example, as a method for producing methanol, a method of reacting carbon monoxide obtained by partial combustion of hydrocarbon with hydrogen gas at a high temperature and a high pressure is commonly used. Carbon monoxide and hydrogen gas, which are raw materials, can be produced, for example, by partial combustion of methane (natural gas), steam reforming, and the like.

In these years, for the effective use of natural gas such as shale gas, a method is proposed for producing an oxidation reaction product such as methanol by oxidizing methane contained in natural gas. Methane monooxygenase contained in methanotrophs oxidizes methane to methanol in nature (Non Patent Literatures 3 and 4). As a method for artificially producing methanol from methane, a currently known method is a method for producing methanol by oxidizing methane by hydrogen peroxide in an acetonitrile solvent in the presence of an iron catalyst (Non Patent Literature 2).

Background Art of Third Aspect of Invention

Alcohol, carboxylic acid, and the like, which are of great use in industrial application, are produced industrially by various methods. For example, alcohol, carboxylic acid, and the like are commonly produced by a biochemical method such as fermentation. In particular, ethanol and acetic acid, which are derivatives of ethane, are commonly produced by a biochemical method such as fermentation.

Furthermore, in these years, for the effective use of natural gas such as shale gas, a method is proposed for producing an oxidation reaction product such as alcohol by oxidizing hydrocarbon contained in natural gas. As a method for producing an oxidation reaction product by a vapor phase reaction, for example, there is a method for producing ethanol by oxidizing ethane by dinitrogen monoxide in the presence of an iron catalyst (Non Patent Literature 1). As a method for producing an oxidation reaction product such as alcohol by a liquid phase reaction, there is a method for producing methanol by oxidizing methane by hydrogen peroxide in an acetonitrile solvent in the presence of an iron catalyst (Non Patent Literature 2).

Background Art of Fourth Aspect of Invention

Cyclohexanone and cyclohexanone (KA-oil), which are oxidation products of cyclohexane, are produced industrially by various kinds of methods. For example, a known method of synthesizing uses N-hydroxyphthalimide in the presence of a manganese (II) catalyst and a cobalt (II) catalyst at 100° C. (Non Patent Literature 5).

Also, known is a method of oxidizing cyclohexane with air by a photoreaction. For example, when light irradiation is performed using 9-mesityl-10-methylacridinium ion as a photocatalyst in the presence of hydrochloric acid, cyclohexanone and cyclohexanone can be obtained (Non Patent Literature 6).

Background Art of Fifth Aspect of Invention

Oxidization of an olefin to a 1,2-diol is an important industrial process for producing precursors of various kinds of chemical substances such as resins, pharmaceutical agents, dyes, insecticides, and perfume compounds in the fields of fine chemicals and speciality chemicals. Several methods for converting olefins to corresponding epoxides and alcohols by oxidization using inorganic metal oxo complexes and metallic oxides having heavy atoms have been reported. High-valent $Os^{VIII}O_4$ is an effective and selective reagent for oxidizing an olefin to a 1,2-diol (Non Patent Literatures 7 to 14). However, the toxicity, sublimation property, and waste of the osmium compound cause serious problems.

On the other hand, owing to their high reactivity, radicals are important chemical species that are widely used. For example, sodium chlorite ($NaClO_2$) is a non-toxic inexpensive oxidizing reagent and has been used as a precursor of a chlorine dioxide radical ($ClO_2 \cdot$) (Non Patent Literatures 15 to 18).

CITATION LIST

Non Patent Literature

Non Patent Literature 1: Jeffrey R. Long and co-workers Nature Chem. 2014, 6, 590
Non Patent Literature 2: Georg Suss-Fink and co-workers Adv. Synth. Catal. 2004, 346, 317
Non Patent Literature 3: I. Bertini, H. B. Gray, S. J. Lippard, J. S. Valentine, "Bioinorganic Chemistry", University Science Books, California (1994)

Non Patent Literature 4: S. J. Lippard, J. M. Berg, "Principles of Bioinorganic Chemistry", University Science Books, California (1994)

Non Patent Literature 5: Ishii, Y and co-workers J. Org. Chem. 2001, 66, 7889

Non Patent Literature 6: Ohkubo, K. and co-workers, Chem. Commun. 2011, 47, 8515

Non Patent Literature 7: M. Schroeder, Chem. Rev., 1980, 80, 187-213

Non Patent Literature 8: (a) E. N. Jacobsen, I. Marko, W. S. Mungall, G. Schroeder and K. B. Sharpless, J. Am. Chem. Soc., 1988, 110, 1968-1970; and (b) S. G. Hentges and K. B. Sharpless, J. Am. Chem. Soc., 1980, 102, 4263-4265

Non Patent Literature 9: W. Yu, Y Mei, Y Kang, Z. Hua and Z. Jin, Org. Lett., 2004, 6, 3217-3219

Non Patent Literature 10: (a) A. J. DelMonte, J. Haller, K. N. Houk, K. B. Sharpless, D. A. Singleton, T. Strassner, and A. A. Thomas, J. Am. Chem. Soc., 1997, 119, 9907-9908; and (b) J. S. M. Wai, I. Marko, J. S. Svendsen, M. G. Finn, E. N. Jacobsen and K. B. Sharpless, J. Am. Chem. Soc., 1989, 111, 1123-1125

Non Patent Literature 11: (a) S. Kobayashi, M. Endo and S. Nagayama, J. Am. Chem. Soc., 1999, 121, 11229-11230; and (b) S. Kobayashi, T. Ishida and R. Akiyama, Org. Lett., 2001, 3, 2649-2652

Non Patent Literature 12: H. C. Kolb, P. G. Andersson and K. B. Sharpless, J. Am. Chem. Soc., 1994, 116, 1278-1291

Non Patent Literature 13: E. J. Corey and M. C. Noe, J. Am. Chem. Soc., 1996, 118, 11038-11053

Non Patent Literature 14: S. Y Jonsson, K. Faernegrdh and J.-E. Baeckvall, J. Am. Chem. Soc., 2001, 123, 1365-1371

Non Patent Literature 15: H. Dodgen and H. Taube, J. Am. Chem. Soc., 1949, 71, 2501-2504

Non Patent Literature 16: J. K. Leigh, J. Rajput, and D. E. Richardson, Inorg. Chem., 2014, 53, 6715-6727

Non Patent Literature 17: C. L. Latshaw, Tappi J., 1994, 163-166

Non Patent Literature 18: (a) J. J. Leddy, in Riegel's Handbook of Industrial Chemistry, 8th edn. Ed., J. A. Kent, Van Nostrand Reinhold Co. Inc, New York, 1983, pp. 212-235; (b) I. Fabian, Coord. Chem. Rev., 2001, 216-217, 449-472

SUMMARY OF INVENTION

Technical Problem

Technical Problem to be Solved by First Aspect of Invention

The production process of carbon monoxide by partial combustion of hydrocarbon, however, has a problem of releasing large amounts of carbon dioxide (greenhouse gas). Also, the production of an oxidation reaction product by a biochemical method such as fermentation has a problem of requiring much energy in fertilization, crop-dusting, harvesting, and transport in the process of cultivating raw material crops (e.g., maize), for example. Furthermore, these methods cannot produce alcohols, carboxylic acids, and the like using hydrocarbon as a raw material, and thus are not suitable for effective use of hydrocarbon contained in natural gas.

On the other hand, the method for producing an oxidation reaction product using hydrocarbon as a raw material has the following problems. First, in the production method by a vapor phase reaction, the reaction efficiency is poor because the collision frequency of molecules in a reaction system is low. While a solid phase-vapor phase reaction using an oxidizing agent or a catalyst has mainly been studied, hydrocarbon shows a low adsorption characteristic to a solid and no efficient result has been reported. Thus, the production method by a vapor phase reaction requires extreme reaction conditions such as a high temperature and a high pressure, which cause problems in manufacturing efficiency, cost, and safety measures. On the other hand, the production method by a liquid phase reaction has difficulty in reaction control of radicals (intermediates) generated from hydrocarbon (raw material), and side reactions are likely to occur. Because of these problems, none of the methods for producing an oxidation reaction product using hydrocarbon as a raw material can produce the oxidation reaction product efficiently, and are not yet in industrial actual use.

Hence, the first aspect of the present invention is intended to provide a method for producing an oxidation reaction product of the hydrocarbon or a derivative thereof efficiently using hydrocarbon or a derivative thereof as a raw material.

Technical Problem to be Solved by Second Aspect of Invention

In the production process of carbon monoxide by partial combustion of methane, there is a problem of releasing large amounts of carbon dioxide (greenhouse gas). For solving this problem, there is a need to activate a methane molecule without combustion. Methane, however, is the most inactive hydrocarbon for lack of bipolar moment caused by a strong carbon-hydrogen bond (104 kcal/mol) and a high symmetry, which are the main chemical properties. Thus, it is difficult to activate methane without combustion. There is also a problem of the cost of hydrogen gas production.

A chlorine radical is known as a means for cleaving the carbon-hydrogen bond of methane without combustion. The chlorine radical can be obtained normally by irradiating chlorine gas with light. In this method, however, two chlorine radical molecules are generated per chlorine molecule. Thus, even if one of the chlorine radical molecules cleaves the carbon-hydrogen bond of methane to create a methyl radical, the other of the chlorine radical molecules causes the additional reaction to generate methane chloride. That is, in this method, only methane chloride which is of little use can be obtained while oxidation reaction products such as methanol and formic acid of great use cannot be obtained.

As to the production of methanol and the like utilizing methane monooxygenase contained in methanotrophs (Non Patent Literatures 3 and 4), methane monooxygenase is isolated and purified, and the property thereof is checked. However, there still remains a lot of uncertainty, even an oxidation reaction in a test tube is very difficult, and thus the production is far from the practical use.

On the other hand, the method for producing an oxidation reaction product using gaseous hydrocarbon as a raw material has the following problems. First, in the production method by a vapor phase reaction, the reaction efficiency is poor because the collision frequency of molecules in a reaction system is low. While a solid phase-vapor phase reaction using an oxidizing agent or a catalyst has mainly been studied, hydrocarbon shows a low adsorption characteristic to a solid and no efficient result has been reported. Thus, the production method by a vapor phase reaction requires extreme reaction conditions such as a high temperature and a high pressure, which cause problems in manufacturing efficiency, cost, and safety measures. On the other hand, because the production method by a liquid phase reaction (for example, Non Patent Literature 3, etc.) has difficulty in reaction control of radicals (intermediates) generated from hydrocarbon (raw material) and side reactions are likely to occur, the production method has problems in yield and selectivity. Because of these problems, none of the methods for producing an oxidation reaction product using hydrocarbon as a raw material can produce the oxidation reaction product efficiently, and are not yet in industrial actual use.

Hence, the second aspect of the present invention is intended to provide a method for producing an oxidation reaction product of methane efficiently using the methane as a raw material.

Technical Problem to be Solved by Third Aspect of Invention

However, the production of an oxidation reaction product by a biochemical method such as fermentation has a problem of requiring much energy in fertilization, crop-dusting, harvesting, and transport in the process of cultivating raw material crops (e.g., maize), for example. Furthermore, these methods cannot produce alcohols, carboxylic acids, and the like using hydrocarbon as a raw material, and thus are not suitable for effective use of hydrocarbon contained in natural gas.

On the other hand, the method for producing an oxidation reaction product using hydrocarbon as a raw material has the following problems. First, in the production method by a vapor phase reaction, the reaction efficiency is poor because the collision frequency of molecules in a reaction system is low. While a solid phase-vapor phase reaction using an oxidizing agent or a catalyst has mainly been studied, hydrocarbon shows a low adsorption characteristic to a solid and no efficient result has been reported. Thus, the production method by a vapor phase reaction requires extreme reaction conditions such as a high temperature and a high pressure, which cause problems in manufacturing efficiency, cost, and safety measures. On the other hand, the production method by a liquid phase reaction has difficulty in reaction control of radicals (intermediates) generated from hydrocarbon (raw material), side reactions are likely to occur. Because of these problems, none of the methods for producing an oxidation reaction product using hydrocarbon as a raw material can produce the oxidation reaction product efficiently, and are not yet in industrial actual use.

Hence, the third aspect of the present invention is intended to provide a method for producing an oxidation reaction product of ethane efficiently using the ethane as a raw material.

Technical Problem to be Solved by Fourth Aspect of Invention

However, the process that requires a heavy metal catalyst and a high temperature has a problem that an environmental load is high.

On the other hand, the method of using 9-mesityl-10-methylacridinium ion as a photocatalyst still has problems of a low product yield and a long reaction time.

Hence, the fourth aspect of the present invention is intended to provide a method for producing an oxidation reaction product of cyclohexane efficiently using the cyclohexane as a raw material.

Technical Problem to be Solved by Fifth Aspect of Invention

However, high energy is generally required for generating radicals. Thus, heating or the like to raise the temperature is required, which causes problems in cost and reaction control. Hence, the fifth aspect of the present invention is intended to provide a method for producing an oxidation reaction product of an olefin in which the reaction can be performed under mild conditions.

Solution to Problem

Solution to Problem of First Aspect of Invention

In order to achieve the above object, the first aspect of the present invention provides a method for producing an oxidation reaction product of hydrocarbon or a derivative thereof (hereinafter, also simply referred to as "the production method of the first aspect of the present invention", "the production method of the first aspect of the present invention", or "the first aspect of the present invention"). The method includes the step of: irradiating a reaction system with light in the presence of a raw material and a chlorine dioxide radical. The raw material is hydrocarbon or a derivative thereof, the reaction system is a reaction system containing an organic phase, and the organic phase contains the raw material and the chlorine dioxide radical. In the step of irradiating a reaction system with light, the raw material is oxidized by the light irradiation to generate an oxidation reaction product of the raw material.

Solution to Problem of Second Aspect of Invention

In order to achieve the above object, the second aspect of the present invention provides a method for producing an oxidation reaction product of methane (hereinafter, also simply referred to as "the production method of the second aspect of the present invention", "the production method of the second aspect of the present invention", or "the second aspect of the present invention"). The method includes the step of: irradiating a reaction system with light in the presence of methane and a chlorine dioxide radical. The reaction system is a reaction system containing an organic phase, and the organic phase contains the methane and the chlorine dioxide radical. In the step of irradiating a reaction system with light, the methane is oxidized by the light irradiation to generate an oxidation reaction product of the methane.

Solution to Problem of Third Aspect of Invention

In order to achieve the above object, the third aspect of the present invention provides a method for producing an oxidation reaction product of ethane (hereinafter, also simply referred to as "the production method of the third aspect of the present invention", "the production method of the third aspect of the present invention", or "the third aspect of the present invention"). The method includes the step of: irradiating a reaction system with light in the presence of ethane and a chlorine dioxide radical. The reaction system is a reaction system containing an organic phase, and the organic phase contains the ethane and the chlorine dioxide radical. In the step of irradiating a reaction system with light, the ethane is oxidized by the light irradiation to generate an oxidation reaction product of the ethane.

Solution to Problem of Fourth Aspect of Invention

In order to achieve the above object, the fourth aspect of the present invention provides a method for producing an oxidation reaction product of cyclohexane (hereinafter, also simply referred to as "the production method of the fourth aspect of the present invention", "the production method of the fourth aspect of the present invention", or "the fourth aspect of the present invention"). The method includes the step of: irradiating a reaction system with light in the presence of cyclohexane and a chlorine dioxide radical. The reaction system is a reaction system containing an organic phase, and the organic phase contains the cyclohexane and the chlorine dioxide radical. In the step of irradiating a reaction system with light, the cyclohexane is oxidized by the light irradiation to generate an oxidation reaction product of the cyclohexane.

Solution to Problem of Fifth Aspect of Invention

In order to achieve the above object, the fifth aspect of the present invention provides a method for producing an oxidation reaction product of an olefin (hereinafter, also simply referred to as "the production method of the fifth aspect of the present invention", "the production method of the fifth aspect of the present invention", or "the fifth aspect of the present invention"). The method includes the steps of: reacting at least one of a Lewis acid or a Brønsted acid with a radical source to generate a radical; and oxidizing an olefin using the radical as an oxidizing agent.

Advantageous Effects of Invention

Advantageous Effects of First Aspect of Invention

According to the production method of the first aspect of the present invention, using hydrocarbon or a derivative thereof as a raw material, an oxidation reaction product of the hydrocarbon or a derivative thereof can be produced efficiently.

Advantageous Effects of Second Aspect of Invention

According to the production method of the second aspect of the present invention, using methane as a raw material, an oxidation reaction product of the methane can be produced efficiently.

Advantageous Effects of Third Aspect of Invention

According to the production method of the third aspect of the present invention, using ethane as a raw material, an oxidation reaction product of the ethane can be produced efficiently.

Advantageous Effects of Fourth Aspect of Invention

According to the production method of the fourth aspect of the present invention, using cyclohexane as a raw material, an oxidation reaction product of the cyclohexane can be produced efficiently.

Advantageous Effects of Fifth Aspect of Invention

According to the method for producing an oxidation reaction product of an olefin of the fifth aspect of the present invention, because the reaction can be performed under mild conditions, the reaction can be controlled easily at low cost.

BRIEF DESCRIPTION OF DRAWINGS

In FIG. 9, (a) shows a spectrum of a MeCN solution that contains $NaClO_2$ (0.10 mM) at 353 K after 1-hour reflux; (b) shows a spectrum of a MeCN solution that contains $NaClO_2$ (0.10 mM) and $CF_3COOH$ (10 mM); and (c) shows a spectrum of a MeCN solution that contains $NaClO_2$ (0.10 mM) and $Sc(OTf)_3$ (10 mM).

In FIG. 10, (a) shows the result obtained regarding $ClO_2 \cdot$; (b) shows the result obtained regarding $H^+ClO_2 \cdot$; and (c) shows the result obtained regarding $Sc^{3+}ClO_2 \cdot$.

In FIG. 15, (a) shows a spin distribution of $H^+ClO_2 \cdot$; and (b) shows a spin distribution of $Sc^{3+}ClO_2 \cdot$.

Figure 19:
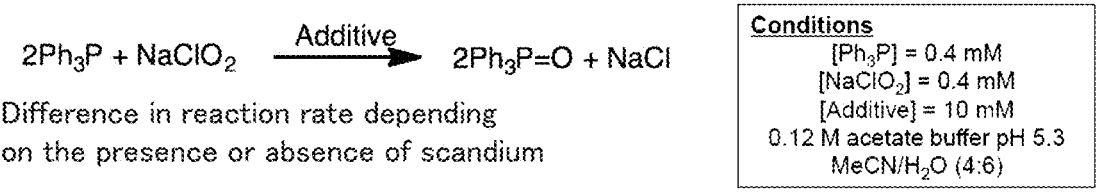
Figure 19:
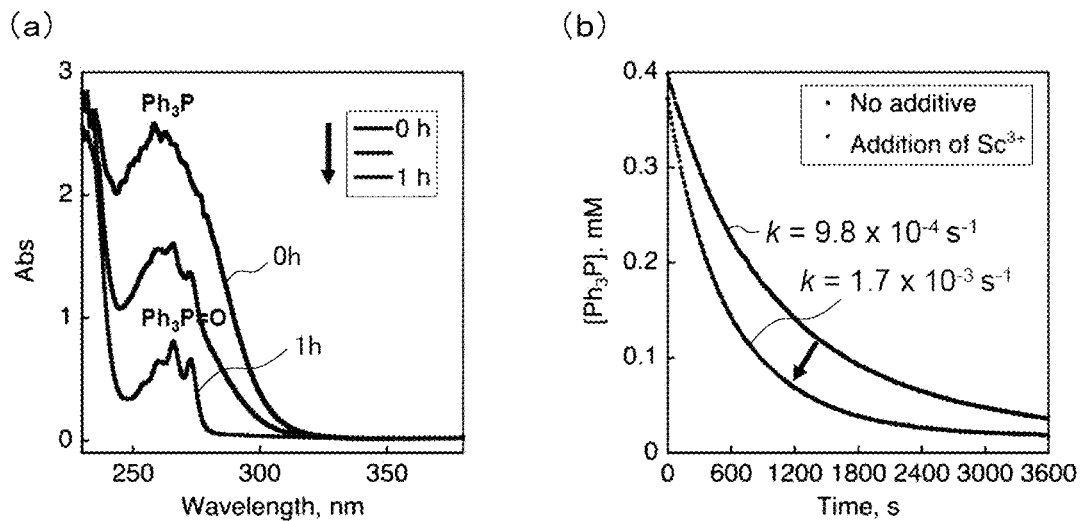

(a) of FIG. 19 is an ultraviolet-visible absorption spectrum showing conversion of triphenylphosphine to triphenylphosphine oxide over time; and (b) of FIG. 19 is a graph showing the change of a triphenylphosphine ($Ph_3P$) concentration over time in the presence and the absence of $Sc(OTf)_3$ ($Sc^{3+}$).

DESCRIPTION OF EMBODIMENTS

The present invention is described below in more detail with reference to illustrative examples. The present invention, however, is not limited by the following description.

Description of Embodiments of First to Fourth Invention

In the first aspect of the present invention, for example, the raw material may be methane. The second aspect of the present invention is an invention in which the raw material is methane in the first aspect of the present invention.

In the first aspect of the present invention, for example, the raw material may be ethane. The third aspect of the present invention is an invention in which the raw material is ethane in the first aspect of the present invention.

In the first aspect of the present invention, for example, the raw material may be cyclohexane. The fourth aspect of the present invention is an invention in which the raw material is cyclohexane in the first aspect of the present invention.

In the step of irradiating a reaction system with light (hereinafter, also referred to as the reaction step) of the production method of each of the first to fourth aspects of the present invention, at least the organic phase may be irradiated with light.

The production method of each of the first to fourth aspects of the present invention may further include the step of generating the chlorine dioxide radicals.

In the production method of each of the first to fourth aspects of the present invention, the reaction system may be a biphasic reaction system that further contains an aqueous phase. In this case, the production method of the present invention may further include the step of generating the chlorine dioxide radicals. In the step of generating the chlorine dioxide radicals, the aqueous phase may contain a chlorine dioxide radical source and the chlorine dioxide radicals may be generated from the chlorine dioxide radical source. Furthermore, in the step of generating the chlorine dioxide radicals, for example, the chlorine dioxide radical source may be a chlorite ion ($ClO_2^-$) and at least one of a Lewis acid and a Brønsted acid may be reacted with the chlorite ion to generate the chlorine dioxide radical.

The production method of each of the first to fourth aspects of the present invention may further include the step of recovering the oxidation reaction product after the reaction step. The recovery step may be a step of recovering the aqueous phase containing the oxidation reaction product from the reaction system.

In the production method of each of the first to fourth aspects of the present invention, for example, the reaction may be performed in an atmosphere in which a temperature is minus 100° C. to 200° C. and a pressure is 0.1 to 10 MPa. Alternatively, in the production method of the present invention, for example, the reaction may be performed in an atmosphere in which a temperature is 0° C. to 40° C. and a pressure is 0.1 to 0.5 MPa.

In the reaction step in the production method of each of the first to fourth aspects of the present invention, for example, light irradiation may be performed in the state where oxygen ($O_2$) is dissolved in the aqueous phase.

In the production method of each of the first to fourth aspects of the present invention, the organic phase contains, for example, an organic solvent. The organic solvent may be, for example, a hydrocarbon solvent, a halogenated solvent, or a fluorous solvent. In the case where the raw material is cyclohexane in the production method of the first aspect of the present invention (i.e., the production method of the fourth aspect of the present invention), for example, the cyclohexane may serve as the raw material of the oxidation reaction product as well as the organic solvent.

In the production method of the first aspect of the present invention, for example, the raw material hydrocarbon may be saturated hydrocarbon. The saturated hydrocarbon may be, as described above, methane, ethane, or cyclohexane, for example.

In the production method of the first aspect of the present invention, for example, the raw material hydrocarbon may be nonaromatic unsaturated hydrocarbon.

In the production method of the first aspect of the present invention, for example, the raw material hydrocarbon may be the aromatic hydrocarbon. The aromatic hydrocarbon may be, for example, benzene.

In the production method of the first aspect of the present invention, in the case where the raw material hydrocarbon is saturated hydrocarbon or nonaromatic unsaturated hydrocarbon, for example, the oxidation reaction product may be at least one selected from the group consisting of alcohol, carboxylic acid, aldehyde, ketone, percarboxylic acid, and hydroperoxide.

In the production method of the first aspect of the present invention, in the case where the raw material hydrocarbon is methane (i.e., the production method of the second aspect of the present invention), for example, the oxidation reaction product may include at least one selected from the group consisting of methanol, formic acid, formaldehyde, and methyl hydroperoxide.

In the production method of the first aspect of the present invention, in the case where the raw material hydrocarbon is ethane (i.e., the production method of the third aspect of the present invention according to the present invention), for example, the oxidation reaction product may include at least one selected from the group consisting of ethanol, acetic acid, acetaldehyde, and ethyl hydroperoxide.

In the production method of the first aspect of the present invention, in the case where the raw material hydrocarbon is cyclohexane (i.e., the production method of the fourth aspect of the present invention), for example, the oxidation reaction product may include at least one selected from the group consisting of cyclohexanol, cyclohexanone, cyclohexane hydroperoxide, and ring-opening oxide (e.g., adipic acid).

In the production method of the first aspect of the present invention, in the case where the raw material hydrocarbon is aromatic hydrocarbon, for example, the oxidation reaction product may include at least one of phenol and quinone. It is to be noted that, while "phenol" denotes both hydroxy benzene and aromatic hydroxy compounds in general (including hydroxy benzene) each obtained by substituting a hydrogen atom of an aromatic (e.g., aromatic hydrocarbon or heteroaromatic) nucleus with a hydroxy group (hydroxyl group), the "phenol" denotes the latter in the present invention, unless otherwise stated. Furthermore, while "quinone" denotes both p-benzoquinone and dicarbonyl compounds in general (including p-benzoquinone and o-benzoquinone) obtained by substituting two hydrogen atoms of an aromatic ring (e.g., a benzene ring) in an aromatic (e.g., aromatic hydrocarbon or heteroaromatic) with two oxygen atoms, the "quinone" denotes the latter in the present invention, unless otherwise stated.

In the production method of the first aspect of the present invention, in the case where the raw material hydrocarbon is benzene, for example, the oxidation reaction product may include at least one selected from the group consisting of hydroxy benzene, p-benzoquinone, o-benzoquinone, hydroquinone, and catechol.

More specifically, the production method of each of the first to fourth aspects of the present invention can be performed as described below, for example.

[1. Hydrocarbon or Derivative Thereof]

First, a raw material (substrate) hydrocarbon or a derivative there is provided. The raw material may be hydrocarbon itself or a derivative thereof.

The hydrocarbon is not particularly limited, and may be, for example, nonaromatic or aromatic and saturated or unsaturated. More specifically, the hydrocarbon may be, for example, straight-chain or branched saturated or unsaturated hydrocarbon (e.g., straight-chain or branched alkane, straight-chain or branched alkene, straight-chain or branched alkyne, etc.). The hydrocarbon may be, for example, saturated or unsaturated hydrocarbon (e.g., cycloalkane, cycloalkene, etc.) having a nonaromatic ring structure. Furthermore, the hydrocarbon may be aromatic hydrocarbon. The hydrocarbon may or may not include one or more aromatic or nonaromatic rings and may or may not include one or more straight-chain or branched saturated or unsaturated hydrocarbon in its structure. Specific examples of the hydrocarbon include methane, ethane, propane, n-butane, 2-methylpropane, n-pentane, n-hexane, ethylene, propylene, 1,3-butadiene, acetylene, cyclopentane, cyclohexane, cycloheptane, cyclooctane, methyl cyclohexane, cyclohexene, benzene, toluene, o-xylene, m-xylene, p-xylene, mesitylene, durene, biphenyl, naphthalene, 1-methyl naphthalene, 2-methyl naphthalene, anthracene, phenanthrene, pyrene, and styrene.

In the present invention, a "derivative" of hydrocarbon is an organic compound containing hetero element (an element other than carbon and hydrogen). The hetero element is not particularly limited, and the examples thereof include oxygen (O), nitrogen (N), sulfur (S), and halogens. Examples of the halogen include fluorine (F), chlorine (Cl), bromine (Br), and iodine (I). The derivative may be, for example, an organic compound having a structure in which a hydrocarbon group and any substituent or atomic group are bound. Also, a derivative may be, for example, a compound having a structure in which more than one hydrocarbon group is bound through any atomic group, wherein the hydrocarbon group may or may not be substituted with one or more arbitrary substituents. By oxidizing a part of the hydrocarbon group by an oxidation reaction in the reaction step, an oxidation reaction product of a derivative of the hydrocarbon may be produced. The hydrocarbon group is not particularly limited, and can be, for example, a monovalent or divalent or more group induced from the hydrocarbon. In the hydrocarbon group, for example, one or more carbon atoms may be substituted with a heteroatom. Specifically, for example, by substituting one carbon atom (and a hydrogen atom bound thereto) of a phenyl group with a nitrogen atom, a pyridyl group may be formed. There is no limitation on the substituent or the atomic group, and examples of the substituent or the atomic group include hydroxy groups, halogen groups (a fluoro group, a chloro group, a bromo group, an iodo group, etc.), alkoxy groups, aryloxy groups (e.g., a phenoxy group, etc.), carboxy groups, alkoxycarbonyl groups, aryloxycarbonyl groups (e.g., a phenoxycarbonyl group, etc.), mercapto groups, alkylthio groups, arylthio groups (e.g., a phenylthio group, etc.), amino groups (e.g., an amino group, an alkylamino group, a dialkylamino group, etc.) each having or not having a substituent, ether bonds (—O—), ester bonds (—CO—O—), and thioether bonds (—S—).

In the present invention, a chain compound (e.g., alkane, unsaturated aliphatic hydrocarbon, etc.) or a chain substituent (e.g., an alkyl group, hydrocarbon groups such as an unsaturated aliphatic hydrocarbon group, etc.) induced from the chain compound may be straight-chain or branched, unless otherwise stated, and the number of carbons thereof is not particularly limited, and may be, for example, 1 to 40, 1 to 32, 1 to 24, 1 to 18, 1 to 12, 1 to 6, or 1 to 2 (at least 2 in the case of an unsaturated hydrocarbon group). Furthermore, in the present invention, as to a cyclic compound (e.g., cyclic saturated hydrocarbon, nonaromatic cyclic unsaturated hydrocarbon, aromatic hydrocarbon, a heteroaromatic compound, etc.) or a cyclic group (e.g., a cyclic saturated hydrocarbon group, a nonaromatic cyclic unsaturated hydrocarbon group, an aryl group, a heteroaryl group, etc.) induced from the cyclic compound, the number of ring members (the number of atoms that compose a ring) is not particularly limited and may be, for example, 5 to 32, 5 to 24, 6 to 18, 6 to 12, or 6 to 10. When a substituent or the like has isomers, any isomer can be used, unless otherwise stated. For example, in the case of simply describing as a "naphthyl group", it may be a 1-naphthyl group or a 2-naphthyl group.

In the present invention, when a compound (e.g., the electron donor-acceptor linked molecule) has isomers such as tautomers and stereoisomers (e.g., a geometric isomer, a conformer, and an optical isomer), any isomer can be used in the present invention, unless otherwise stated. Furthermore, when a compound (e.g., the electron donor-acceptor linked molecule) can form salt, the salt can be used in the present invention, unless otherwise stated. The salt may be an acid addition salt or a base addition salt. Moreover, an acid that forms the acid addition salt may be either an inorganic acid or an organic acid, and a base that forms the base addition salt may be either an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxides, alkali metal hydroxides, alkaline-earth metal hydroxides, carbonates, and hydrogencarbonates. More specifically, the inorganic base may be, for example, sodium hydroxide, potassium hydroxide, potassium carbonate, sodium carbonate, sodium hydrogencarbonate, potassium hydrogencarbonate, calcium hydroxide, and calcium carbonate. The organic base also is not particularly limited, and examples thereof include ethanolamine, triethylamine, and tris(hydroxymethyl)aminomethane. The method for producing these salts also is not particularly limited. For example, they can be produced by adding an acid or a base such as described above to the compound as appropriate by a known method.

The raw material (substrate) is, as described above, methane in the second aspect of the present invention, ethane in the third aspect of the present invention, and cyclohexane in the fourth aspect of the present invention according to the present invention.

[2. Reaction System]

Next, the reaction system is provided. The reaction system contains, as described above, an organic phase. The reaction system may be, for example, a monophasic reaction system containing only an organic phase or a biphasic reaction system containing an organic phase and an aqueous phase.

(1) Organic Phase

First, the organic phase is described.

The organic phase contains, as described above, the raw material (hydrocarbon or a derivative thereof). The organic phase is, for example, an organic phase in which the raw material is dissolved in an organic solvent.

The organic solvent is not limited to particular solvents. In the case where the reaction system is a biphasic reaction system containing an aqueous phase and an organic phase, the organic solvent is preferably a solvent that can form the biphasic system. One kind of the organic solvents may be used alone or two or more of them may be used in combination. Examples of the organic solvent include, as described above, hydrocarbon solvents, halogenated solvents, and fluorous solvents. The "fluorous solvent" is one kind of the halogenated solvents. For example, the "fluorous solvent" is a solvent in which all of or the most of hydrogen atoms of hydrocarbon are substituted with fluorine atoms. The fluorous solvent may be, for example, a solvent in which at least 50%, at least 60%, at least 70%, at least 80%, or at least 90% of hydrogen atoms of hydrocarbon are substituted with fluorine atoms.

The hydrocarbon solvent is not particularly limited, and examples thereof include n-hexane, cyclohexane, benzene, toluene, o-xylene, m-xylene, and p-xylene. For example, the hydrocarbon solvent may also serve as a raw material hydrocarbon.

The halogenated solvent is not particularly limited, and examples thereof include methylene chloride, chloroform, carbon tetrachloride, carbon tetrabromide, and the fluorous solvent described below.

Examples of the fluorous solvent include solvents represented by the following chemical formulae (F1) to (F6). Among them, for example, $CF_3(CF_2)_4CF_3$ and the like are preferable. Use of the fluorous solvent brings about an advantageous effect of suppressing or preventing a side reaction owing to its low reactivity, for example. Examples of the side reaction include an oxidation reaction of a solvent, a hydrogen abstraction reaction or a chlorination reaction of a solvent by chlorine radicals, or a reaction between radicals derived from the raw material (substrate) and a solvent (for example, in the case where the raw material is methane, a reaction between methyl radicals and a solvent). Furthermore, due to the difficulty in mixing of a fluorous solvent and water, a reaction system (fluorous phase) and a product recovery system (aqueous phase) can be separated, which suppresses further oxidation reaction of a product.

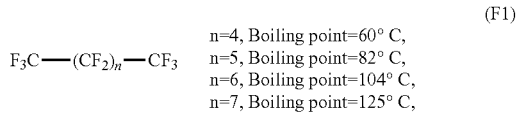
(F1)

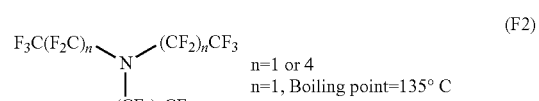
(F2)

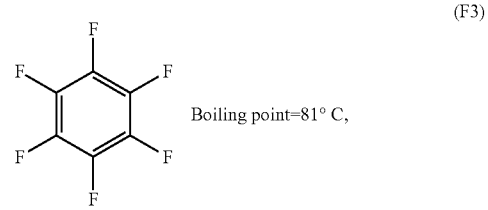 [SMILES: Fc1c(F)c(F)c(F)c(F)c1F]
(F3)

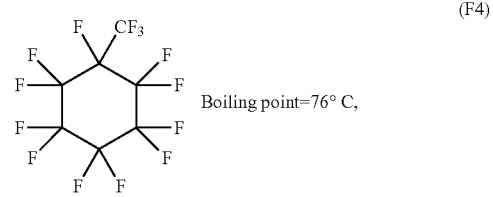 [SMILES: FC(F)(F)C1(F)C(F)(F)C(F)(F)C(F)(F)C(F)(F)C1(F)F]
(F4)

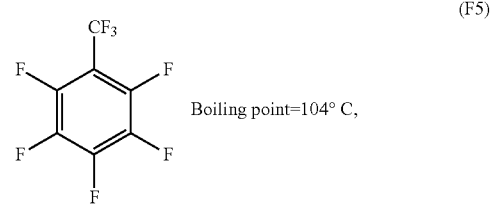 [SMILES: Fc1c(F)c(F)c(C(F)(F)F)c(F)c1F]
(F5)

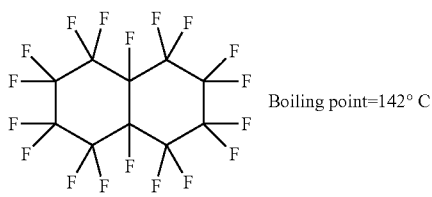

(F6) Boiling point=142° C

It is to be noted that the boiling point of the organic solvent is not particularly limited and can be selected as appropriate. In the reaction step, if there is a need to set the temperature high, it is preferable to select a solvent having a high boiling point. The production method of the present invention, however, can be performed without heating (for example, at ordinary temperature and normal pressure) as described below, for example. In such a case, there is no need for a solvent to have a high boiling point, rather, from the viewpoint of handleability, a solvent having a not so high boiling point is preferable.

In the present invention, in the "solvent" (e.g., an organic solvent in the organic phase or water in the aqueous phase), a raw material (the hydrocarbon or a derivative thereof), a Lewis acid, a Brønsted acid, a radical source, and the like may or may not be dissolved. For example, the production method of the present invention may be performed in the state where the raw material, the Lewis acid, the Brønsted acid, the radical source, and the like are dispersed or precipitated in the solvent.

The concentration of hydrocarbon or a derivative thereof, which is the raw material (substrate), in the organic phase is not particularly limited, and may be, for example, 0.0001 mol/L or more and 60 mol/L or less.

The organic phase may or may not further contain components other than the raw material (hydrocarbon or a derivative thereof) and the organic solvent. Such components are not particularly limited, and examples thereof include a Brønsted acid, a Lewis acid, and oxygen ($O_2$).

The organic phase contains, as described above, the chlorine dioxide radicals. In the case where the reaction system is a monophasic system containing only an organic phase, for example, the chlorine dioxide radicals may be generated separately without involving the organic phase that composes the reaction system and the generated radicals may be extracted by the organic phase. Then, the organic phase containing the extracted dioxide radicals can be subjected to the reaction step as the reaction system. The dioxide radicals can be generated, as described below, in an aqueous phase provided separately, for example (the chlorine dioxide radical generating step). On the other hand, in the case where the reaction system is a biphasic system containing the organic phase and the aqueous phase, for example, the chlorine dioxide radicals may be generated in the aqueous phase of the reaction system and the generated chlorine dioxide radicals may be extracted from the aqueous phase in the organic phase. Then, the biphasic reaction system containing the aqueous phase and the organic phase that contains the chlorine dioxide radicals may be subjected to the reaction step.

(2) Aqueous Phase

Next, the aqueous phase is described. As described above, the reaction system may be a biphasic reaction system that further contains an aqueous phase besides the organic phase. Furthermore, in the case where the reaction system is a monophasic system containing only the organic phase, as described above, the aqueous phase may be used separately for generating the chlorine dioxide radicals.

The aqueous phase may contain a chlorine dioxide radical source, for example. The chlorine dioxide radical source can be, for example, sodium chlorite ($NaClO_2$) as described below. Furthermore, the aqueous phase may contain at least one of a Lewis acid and a Brønsted acid, for example. The aqueous phase contains a chlorite ion ($ClO_2^-$) and a Brønsted acid, for example. The aqueous phase is, for example, an aqueous phase in which the sodium chlorite ($NaClO_2$) and the Brønsted acid (e.g., hydrochloric acid) is dissolved in water. For example, in the state where the sodium chlorite and the Brønsted acid are dissolved in the aqueous phase, the light irradiation (the reaction step) described below may be started. Alternatively, in the state where the chlorine dioxide radical source is contained in the aqueous phase, the organic phase and the aqueous phase may be brought into contact with each other and the chlorine dioxide radicals may be generated by irradiating the aqueous phase with light. Then, by maintaining the light irradiation, the reaction step may be performed.

The aqueous phase can be produced by mixing the chlorine dioxide radical source and water, for example. Furthermore, components other than the chlorine dioxide radical source may or may not be mixed as appropriate. Examples of such a component include the Lewis acid, the Brønsted acid, and the oxygen ($O_2$).

The chlorine dioxide radical source is not particularly limited, and is, for example, chlorous acid ($HClO_2$) or salt thereof. The salt of the chlorous acid is not particularly limited, and may be, for example, metal salt. The metal salt may be, for example, alkali metal salt, alkali earth metal salt, or rare earth salt. More specifically, examples of the metal salt include sodium chlorite ($NaClO_2$), lithium chlorite ($LiClO_2$), potassium chlorite ($KClO_2$), magnesium chlorite ($Mg(ClO_2)_2$), and calcium chlorite ($Ca(ClO_2)_2$). One of these chlorous acids and salts thereof may be used alone or two or more of them may be used in combination. Among them, from the viewpoint of cost, handleability, and the like, sodium chlorite ($NaClO_2$) is preferable.

In the aqueous phase, the concentration of the chlorous acid or salt thereof is not particularly limited, and may be, for example, 0.0001 mol/L or more and 1 mol/L or less in terms of a chlorite ion ($ClO_2^-$) concentration. Furthermore, the number of mols of the chlorite ion ($ClO_2^-$) may be, for example, at least 0.00001 times and at most 1000 times the number of mols of the raw material (hydrocarbon or a derivative thereof).

One kind of the Lewis acids and Brønsted acids may be used alone or two or more of them may be used in combination. Furthermore, only one of the Lewis acid and the Brønsted acid may be used alone, both of them may be used in combination, or one substance may serve as the Lewis acid as well as the Brønsted acid. It is to be noted that, in the present invention, the "Lewis acid" denotes a substance that functions as a Lewis acid to the chlorine dioxide radical source, for example.

The concentration of at least one of the Lewis acid and the Brønsted acid in the aqueous phase is not particularly limited, and can be set as appropriate depending on, for example, the kind or the like of a raw material (substrate) and a desired product (oxidation reaction product). For example, the concentration may be 0.0001 mol/L or more and 1 mol/L or less.

The Lewis acid may be, for example, an organic substance or an inorganic substance. The organic substance may be, for example, an ammonium ion, an organic acid (e.g., carboxylic acid), or the like. The inorganic substance may include one or both of metal ions and nonmetal ions. The metal ion may include one or both of typical metal ions and transition metal ions. The inorganic substance may be, for example, at least one selected from the group consisting of alkali earth metal ions (e.g., $Ca^{2+}$), rare earth ions, $Mg^{2+}$, $Sc^{3+}$, $Li^+$, $Fe^{2+}$, $Fe^{3+}$, $Al^{3+}$, silicate ions, and borate ions. Examples of the alkali earth metal ion include ions of calcium, strontium, barium, and radium. More specifically, examples of the alkali earth metal ion include $Ca^{2+}$, $Sr^{2+}$, $Ba^{2+}$, and $Ra^{2+}$. Furthermore the "rare earth metal" is a generic name of a set of seventeen elements, specifically, two elements such as scandium$_{21}$Sc and yttrium$_{39}$Y and fifteen elements (lanthanoids) from lanthanum$_{57}$La to lutetium$_{71}$Lu. Examples of the rare earth ion include corresponding trivalent cations of the seventeen elements. Examples of the counter ion of the Lewis acid include a trifluoromethanesulfonate ion (also referred to as "$CF_3SO_3^-$" or "$CF_3COO^-$"), a trifluoroacetate ion ($CF_3COO^-$), an acetate ion, a fluoride ion, a chloride ion, a bromide ion, an iodide ion, a sulfate ion, a hydrogen sulfate ion, a sulfite ion, a nitrate ion, a nitrite ion, a phosphate ion, and a phosphite ion. For example, the Lewis acid may be scandium triflate (Sc(OTf)$_3$).

The Lewis acid (including the counter ion) may be, for example, at least one selected from the group consisting of $AlCl_3$, $AlMeCl_2$, $AlMe_2Cl$, $BF_3$, $BPh_3$, $BMe_3$, $TiC_4$, $SiF_4$, and $SiC_4$. It is to be noted that the "Ph" indicates a phenyl group and the "Me" indicates a methyl group.

The Lewis acidity of the Lewis acid is, for example, 0.4 eV or more, although it is not limited. The upper limit of the Lewis acidity is not particularly limited and is, for example, 20 eV or less. It is to be noted that the Lewis acidity can be measured, for example, by the method described in Ohkubo, K.; Fukuzumi, S. Chem. Eur. J., 2000, 6, 4532, J. Am. Chem. Soc. 2002, 124, 10270-10271 or the method described in J. Org. Chem. 2003, 68, 4720-4726. Specifically, the Lewis acidity can be measured by the following method.

(Measurement Method of Lewis Acidity)

As to acetonitrile (MeCN) that contains cobalt tetraphenylporphyrin, saturated $O_2$, and an object whose Lewis acidity is to be measured (e.g., a cation of a metal or the like, represented by $M^{n+}$ in the following chemical reaction formula (1a)) in the following chemical reaction formula (1a), the change of the ultraviolet-visible absorption spectrum is measured at room temperature. On the basis of the obtained reaction rate constant ($k_{cat}$), the ΔE value (eV), which is an indicator of the Lewis acidity, can be calculated. The higher the $k_{cat}$, the stronger the Lewis acidity. Furthermore, the Lewis acidity of an organic compound can be estimated from the energy level of the lowest unoccupied molecular orbital (LUMO) calculated by the quantum chemical calculation. The higher the value at the positive side, the stronger the Lewis acidity.

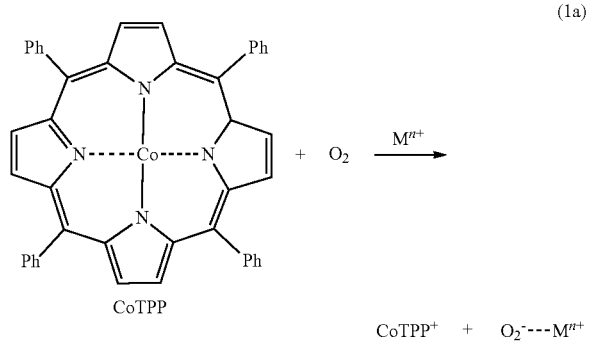

(1a)

The Brønsted acid is not particularly limited, and may be, for example, an inorganic acid or an organic acid. Examples of the Brønsted acid include trifluoromethanesulfonic acid, trifluoroacetic acid, acetic acid, hydrofluoric acid, hydrochloric acid, hydrobromic acid, hydroiodic acid, sulfuric acid, sulfurous acid, nitric acid, nitrous acid, phosphoric acid, and phosphorous acid. The acid dissociation constant $pK_a$ of the Brønsted acid is, for example, 10 or less. The lower limit of the $pK_a$ is not particularly limited, and is, for example, −10 or more.

As to the oxygen ($O_2$), for example, by blowing air or oxygen gas into at least one of an organic phase or water before or after addition of the chlorine dioxide radical source, the Lewis acid, the Brønsted acid, a reactive substrate (raw material), and the like, oxygen may be dissolved. At this time, for example, the water may be saturated with oxygen ($O_2$). By allowing at least one of the aqueous phase and the organic phase to contain the oxygen ($O_2$), for example, the oxidation reaction of hydrocarbon or a derivative thereof, which is the raw material (substrate), can further be promoted.

It is to be noted that, in the present invention, a Lewis acid, a Brønsted acid, a radical source, and the like may or may not be dissolved in water of the aqueous phase as described above. For example, the production method of the present invention may be performed in the state where the Lewis acid, the Brønsted acid, the radical source, and the like are dispersed or precipitated in water.

[3. Chlorine Dioxide Radical Generating Step]

In the production method of the present invention, as described above, the chlorine dioxide radical generating step of generating the chlorine dioxide radicals may be performed.

The chlorine dioxide radical generating step may be performed, for example, by dissolving the chlorine dioxide radical source (e.g., chlorous acid or salt thereof) in water, allowing the resultant to stand still, and allowing chlorine dioxide radicals to be generated from chlorite ions naturally, although it is not particularly limited. At this time, for example, the presence of at least one of the Lewis acid and the Brønsted acid in the water further promotes the generation of chlorine dioxide radicals. Furthermore, for example, the chlorine dioxide radicals may be generated by irradiating the aqueous phase with light described above. However, as described above, the chlorine dioxide radicals can be generated by allowing the aqueous phase to stand still without performing light irradiation.

The mechanism of generating chlorine dioxide radicals from chlorite ions in water can be speculated to be the following scheme 1, for example. It is to be noted, however, that the scheme 1 merely illustrates a presumable mechanism and by no means limits the present invention. The first (uppermost) reaction formula in the scheme 1 shows a disproportionation reaction of a chlorite ion ($ClO_2^-$), and it can be considered that the equilibrium is prone to move rightward owing to the presence of at least one of a Lewis acid and a Brønsted acid in water. The second (middle) reaction formula in the scheme 1 shows a dimerization reaction in which a hypochlorite ion ($ClO^-$) and a chlorite ion generated in the first reaction formula react to each other to generate dichlorine dioxide ($Cl_2O_2$). It is considered that this reaction proceeds more smoothly when the amount of proton $H^+$ contained in water is greater, i.e., the acidity is stronger. The third (lowermost) reaction formula in the scheme 1 shows radical generation. In this reaction, dichlorine dioxide generated in the second reaction formula reacts with a chlorite ion to generate a chlorine dioxide radical.

Scheme 1

Disproportionation reaction

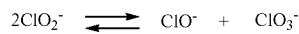

Dimerization reaction

Radical generation

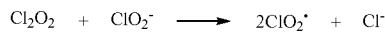

In the case where a biphasic reaction system containing the organic phase and the aqueous phase is used in the subsequent reaction step, for example, after generating the chlorine dioxide radicals in the biphasic reaction system, the reaction system may be subjected to the reaction step as it is. Furthermore, in the case where a monophasic reaction system containing only the organic phase is used in the subsequent reaction step, for example, after generating the chlorine dioxide radicals in the aqueous phase and extracting the generated chlorine dioxide radicals to the organic phase, the aqueous phase may be removed, and the organic phase containing the chlorine dioxide radicals may be subjected to the reaction step as the monophasic reaction system.

[4. Reaction Step]

Subsequently, the reaction step is performed. Hereinafter, the present invention is described with reference to an example in which a biphasic reaction system that contains the organic phase and the aqueous phase is used as the reaction system used in the reaction step.

First, prior to the reaction step, two phases (i.e., the aqueous phase and the organic phase) are brought into contact with each other. At this time, the aqueous phase and the organic phase may be mixed to be in the form of emulsion or the like. However, instead of this, the reaction step may be performed simply in the state where two layers (i.e., a water layer (the aqueous phase) and an organic layer (the organic phase)) are separated and in contact with each other only at the interface.

Figure 1:
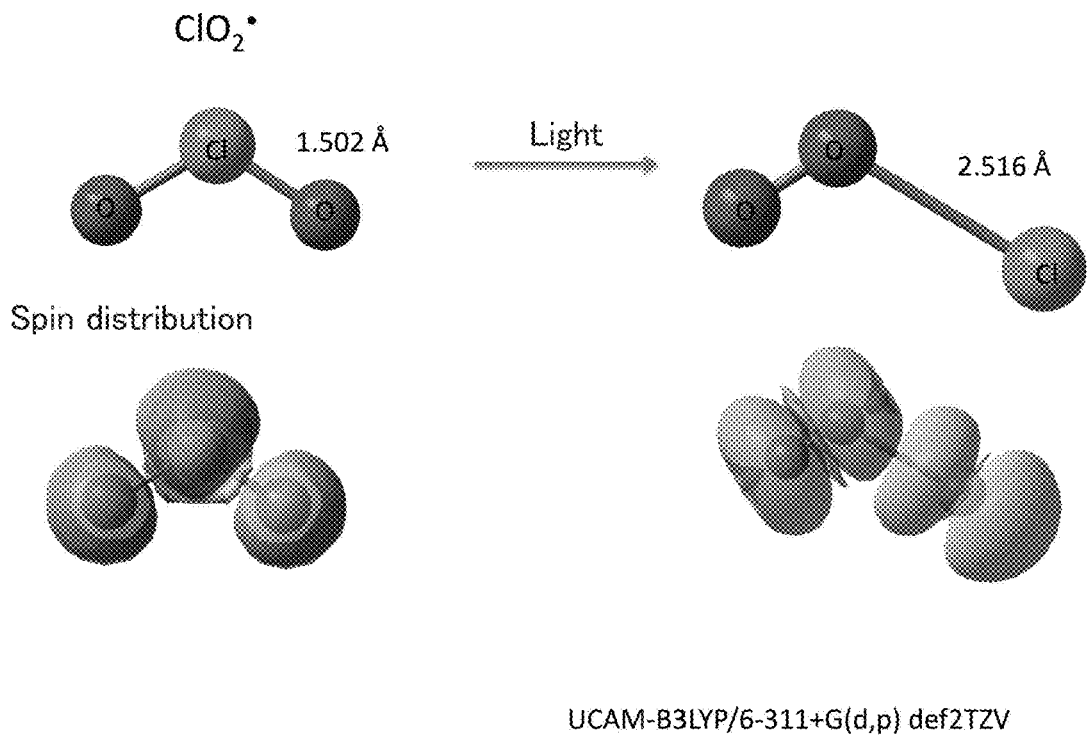
FIG. 1 shows an example of the prediction based on the calculation result of UCAM-B3LYP/6-311+G(d, p) def2TZV in the case where a chlorine dioxide radical ($ClO_2 \cdot$) is irradiated with light.

Next, in the reaction step, for example, the organic phase is irradiated with light as described above. When a chlorine dioxide radical ($ClO_2\cdot$) in the organic phase is irradiated with light, a prediction can be as shown in FIG. 1, for example. FIG. 1 shows the result of the calculation by UCAM-B3LYP/6-311+G(d, p) def2TZV The view on the left side of FIG. 1 shows the state of a chlorine dioxide radical ($ClO_2\cdot$) molecule before the light irradiation, and the view on the right side of FIG. 1 shows the state of a chlorine dioxide radical ($ClO_2\cdot$) molecule after the light irradiation. As shown in FIG. 1, before the light irradiation, two oxygen atoms O are each bound to a chlorine atom Cl, and the bond length of Cl—O is 1.502 Å (0.1502 nm). On the other hand, after the light irradiation, only one of the oxygen atoms O is bound to a chlorine atom Cl, the bond length of Cl—O is 2.516 Å (0.2516 nm), and the other of the oxygen atoms is bound to the oxygen atom that is bound to chlorine atom Cl. It is considered that, thereby the Cl—O bond is cleaved and a chlorine radical (Cl.) and an oxygen molecule ($O_2$) are generated. It is to be noted, however, that FIG. 1 shows an example of the prediction of the calculation result and by no means limits the present invention.

Figure 2:
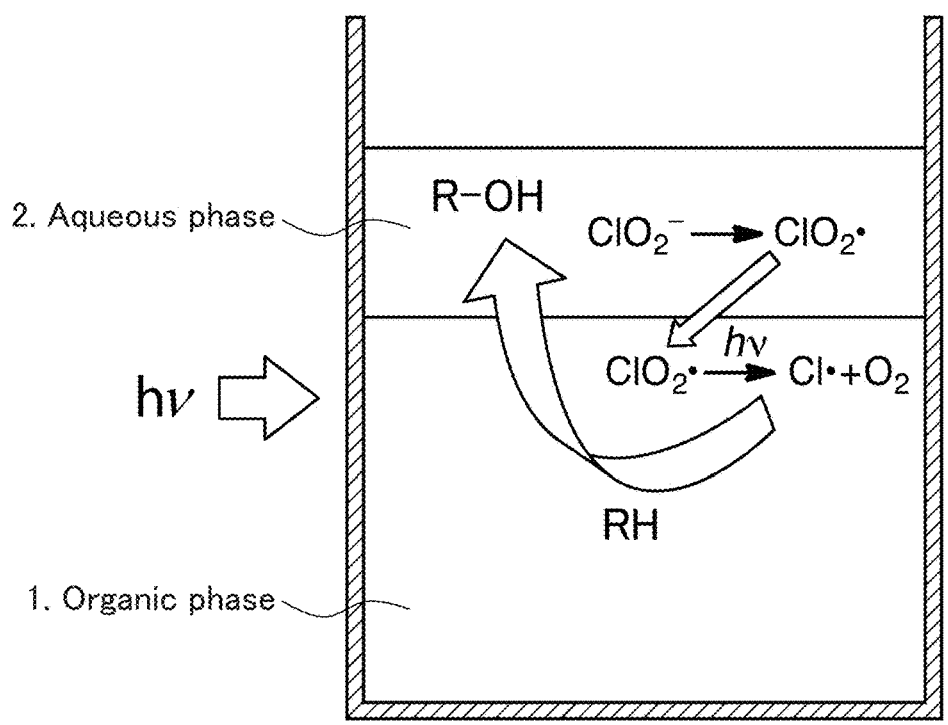
FIG. 2 is a view schematically showing an example of the reaction step in the production method of the first aspect of the present invention.

FIG. 2 schematically shows an example of the reaction step. As shown in FIG. 2, in this reaction system, two layers (i.e., a water layer (the aqueous phase) and an organic layer (the organic phase)) are separated and in contact with each other only at the interface in a reaction vessel. The upper layer is a water layer (the aqueous phase) 2 and the lower layer is an organic layer (the organic phase) 1. It is to be noted that, while FIG. 2 is a cross sectional view, for viewability, hatching of the water layer and organic layer is omitted. As shown in FIG. 2, a chlorite ion ($ClO_2^-$) in the water layer (aqueous phase) reacts with an acid, thereby generating a chlorine dioxide radical ($ClO_2\cdot$). Because the chlorine dioxide radical ($ClO_2\cdot$) is water-insoluble, it is dissolved in the organic layer. Subsequently, by irradiating the organic layer containing the chlorine dioxide radical ($ClO_2\cdot$) with light and applying light energy hv (h denotes the Planck constant and v denotes the light frequency) to the organic layer, the chlorine dioxide radical ($ClO_2\cdot$) in the organic layer is degraded, thereby generating a chlorine radical (Cl.) and an oxygen molecule ($O_2$). Thereby, a substrate (a raw material indicated with RH in FIG. 2) in the organic layer (organic phase) is oxidized, thereby generating an alcohol (indicated with R—OH in FIG. 2), which is an oxidation reaction product. Because the alcohol is water-soluble, it can be dissolved in the water layer. It is to be noted, however, that FIG. 2 shows merely an illustrative example and by no means limits the present invention. For example, although FIG. 2 shows an example in which an oxidation reaction product is a water-soluble alcohol, as described above, the oxidation reaction product is not limited to a water-soluble alcohol and can be any possible oxidation reaction product. Furthermore, in FIG. 2, an organic solvent in the organic layer (organic phase) may be, for example, a fluorous solvent. The organic solvent, however, is not limited to a fluorous solvent, and any organic solvent can be used as described above. Moreover, in FIG. 2, while the water layer is the upper layer and the organic layer is the lower layer, for example, if the organic layer has a lower density (specific gravity), the organic layer serves as the upper layer. The production method of the present invention is not limited to the state where the layers are separated as shown in FIG. 2. For example, as described above, the production method of the present invention may be performed in the state where the two phases are in the form of emulsion or the like or the production method of the present invention may be performed while stirring the two phases.

Figure 3:
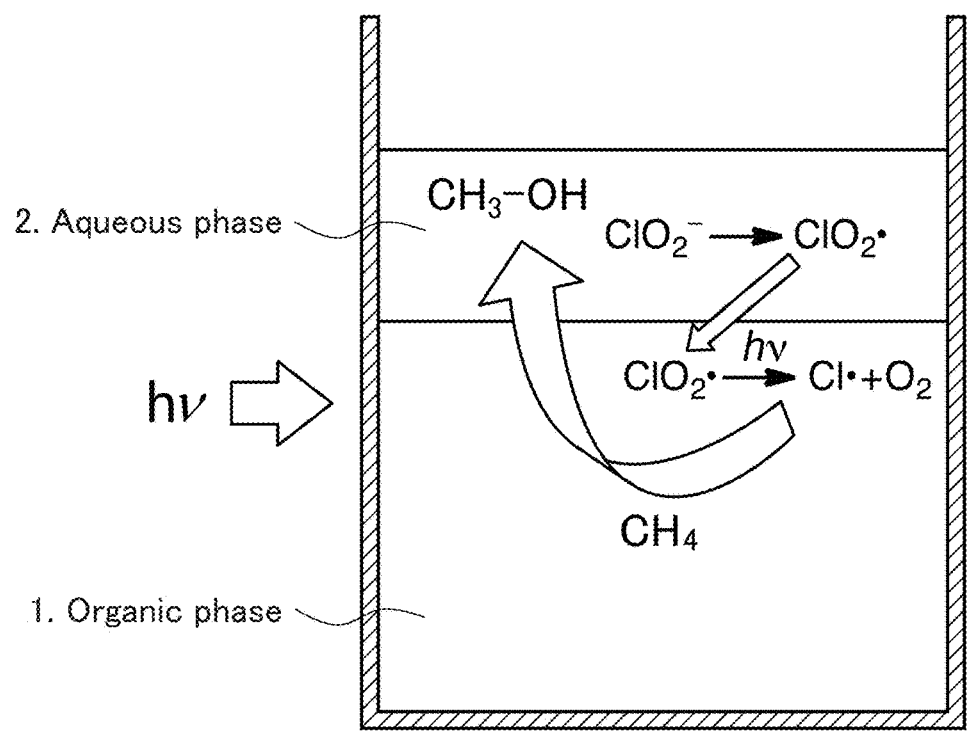
FIG. 3 is a view schematically showing an example of the reaction step in the production method of the second aspect of the present invention.

FIG. 3 schematically shows another example of the reaction step. FIG. 3 is the same as FIG. 2 except that the substrate (raw material) is methane ($CH_4$) and the oxidation reaction product is methanol ($CH_3$—OH). Because methanol is water-soluble, it can be dissolved in a water layer. Furthermore, while FIG. 3 shows an example in which the oxidation reaction product is methanol, as described above, the oxidation reaction product in the case where the substrate (the raw material) is methane is not limited to methanol and can be any possible oxidation reaction product.

Figure 4:
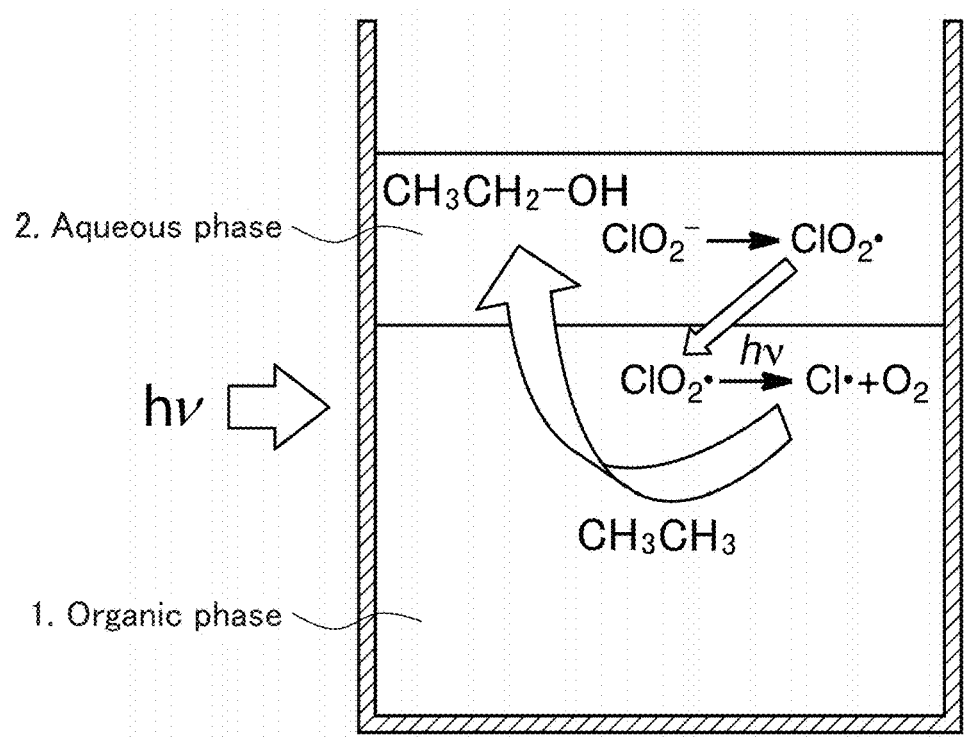
FIG. 4 is a view schematically showing an example of the reaction step in the production method of the third aspect of the present invention.

FIG. 4 schematically shows still another example of the reaction step. FIG. 4 is the same as FIG. 2 except that the substrate (raw material) is ethane ($CH_3CH_3$) and the oxidation reaction product is ethanol ($CH_3CH_2$—OH). Because ethanol is water-soluble, it can be dissolved in a water layer. Furthermore, while FIG. 4 shows an example in which the oxidation reaction product is ethanol, as described above, the oxidation reaction product in the case where the substrate (raw material) is ethane is not limited to ethanol and can be any possible oxidation reaction product.

Figure 5:
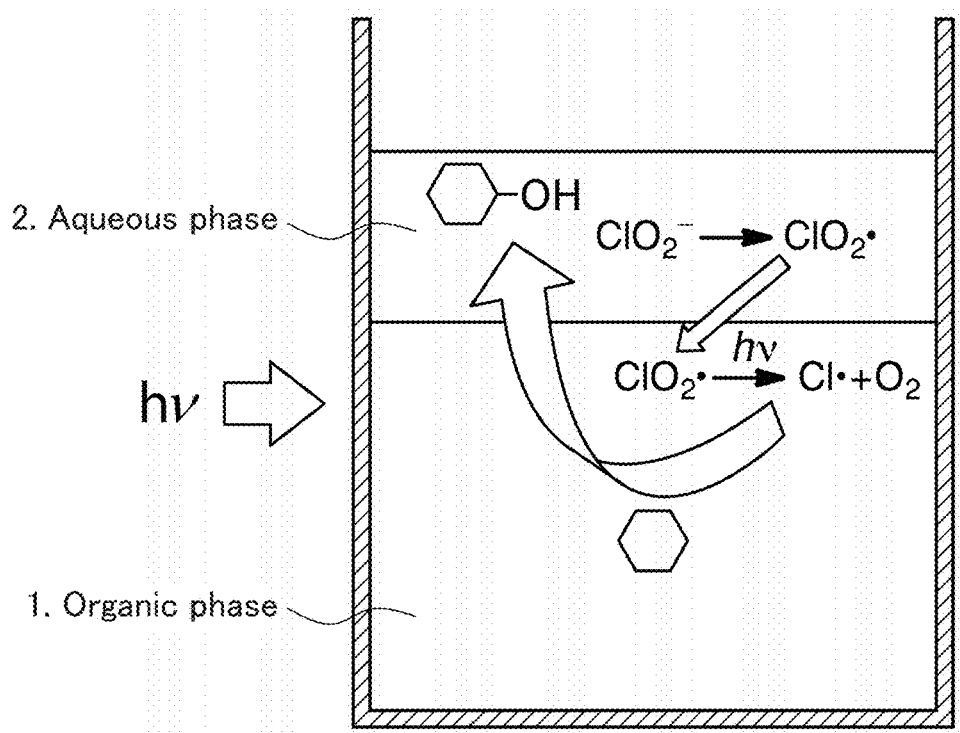
FIG. 5 is a view schematically showing an example of the reaction step in the production method of the fourth aspect of the present invention.

FIG. 5 schematically shows still another example of the reaction step. FIG. 5 is the same as FIG. 2 except that the substrate (raw material) is cyclohexane and the oxidation reaction product is cyclohexanol. Because cyclohexanol is water-soluble, it can be dissolved in a water layer. Furthermore, while FIG. 5 shows an example in which the oxidation reaction product is cyclohexanol, as described above, the oxidation reaction product in the case where the substrate (raw material) is cyclohexane is not limited to cyclohexanol and can be any possible oxidation reaction product.

In the reaction step, the wavelength of the light is not particularly limited, and may be, for example, 200 nm or more and 800 nm or less. The time for light irradiation is also not particularly limited, and may be, for example, 1 min or longer and 1000 h or shorter. The reaction temperature is also not particularly limited, and may be, for example, 0° C. or higher and 100° C. or lower. The ambient pressure in the reaction is not particularly limited, and may be, for example, 0.1 MPa or more and 100 MPa or less. According to the present invention, for example, as described in the Examples below, the reaction step or all the steps including the reaction step can be performed at ordinary temperature (room temperature) and a normal pressure (atmospheric pressure) without heating, pressurizing, depressurizing, or the like at all. It is to be noted that the "room temperature" is not particularly limited, and is, for example, 5 to 35° C. Furthermore, according to the present invention, for example, as described in the Examples below, the reaction step or all the steps including the reaction step can be performed in the atmosphere without performing inert gas substitution or the like.

In the light irradiation, the light source is not particularly limited. For example, excitation can be performed easily by using visible light contained in natural light such as sunlight, for example. Also, for example, instead of or in addition to the natural light, a light source such as a xenon lamp, a halogen lamp, a fluorescent lamp, or a mercury lamp may or may not be used as appropriate. Furthermore, a filter that cuts wavelengths other than a necessary wavelength may or may not be used as appropriate.

The mechanism of generating ethanol by an oxidation reaction of ethane can be speculated as the following scheme 2, for example. It is to be noted, however, that the scheme 2 merely illustrates a presumable mechanism and by no means limits the present invention. The scheme 2 is described specifically as follows. First, as shown in FIG. 1, a chlorine dioxide radical is degraded by light irradiation, thereby generating a chlorine radical (Cl.) and an oxygen molecule ($O_2$). The chlorine radical serves as a hydrogen abstraction agent to ethane and generates an ethyl radical ($CH_3CH_2$.). Then, the oxygen molecule oxidizes the ethyl radical as shown in the scheme 2, thereby generating ethanol.

Scheme 2

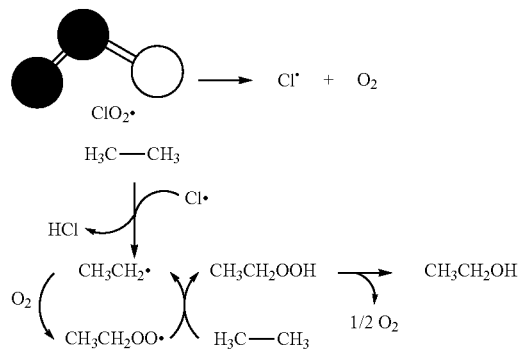

The reaction formula of the case where methanol and formic acid are generated by an oxidation reaction of methane using sodium chlorite is, for example, as the following scheme 3. It is to be noted, however, that the scheme 3 is an example and the oxidation reaction of methane using the present invention is not limited thereto.

Scheme 3

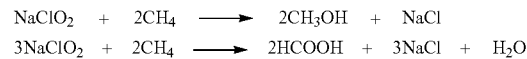

$NaClO_2 + 2CH_4 \longrightarrow 2CH_3OH + NaCl$ $3NaClO_2 + 2CH_4 \longrightarrow 2HCOOH + 3NaCl + H_2O$ The mechanism of generating methanol by an oxidation reaction of methane can be speculated as the following scheme 4, for example. It is to be noted, however, that the scheme 4 merely illustrates a presumable mechanism and by no means limits the present invention. The scheme 4 is described specifically as follows. Similar to the case where ethanol is generated from ethane (scheme 2), first, a chlorine dioxide radical is degraded by light irradiation, thereby generating a chlorine radical (Cl.) and an oxygen molecule ($O_2$). The chlorine radical serves as a hydrogen abstraction agent to methane and generates a methyl radical ($CH_3$.). Then, the oxygen molecule oxidizes the methyl radical as shown in the scheme 4, thereby generating methanol.

Scheme 4

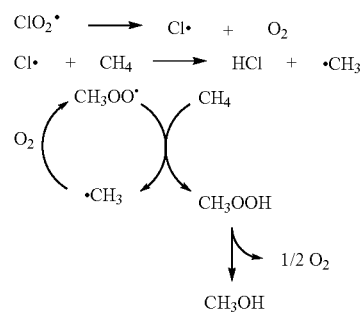

The mechanism of generating cyclohexanol by an oxidation reaction of cyclohexane can be speculated as the following scheme 5, for example. It is to be noted, however, that the scheme 5 merely illustrates a presumable mechanism and by no means limits the present invention. The scheme 5 is described specifically as follows. First, as shown in FIG. 1, a chlorine dioxide radical is degraded by light irradiation, thereby generating a chlorine radical (Cl.) and an oxygen molecule ($O_2$). The chlorine radical serves as a hydrogen abstraction agent to cyclohexane and generates a cyclohexyl radical. Then, the oxygen molecule oxidizes the cyclohexyl radical as shown in the scheme 5, thereby generating cyclohexanol.

Scheme 5

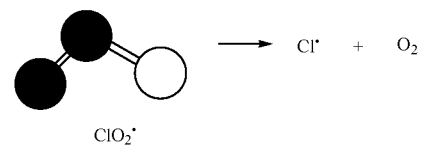

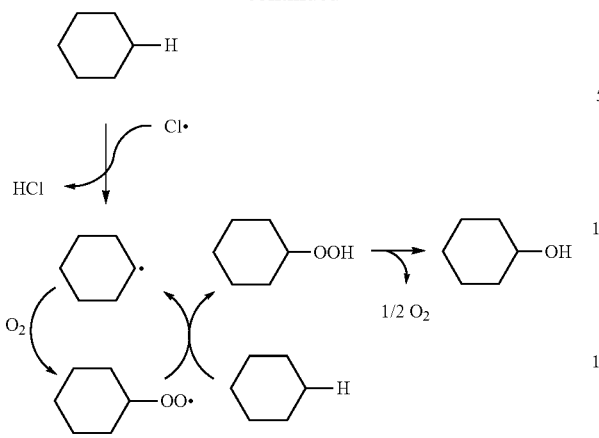

In the first aspect of the present invention, the raw material (substrate) is not limited only to ethane, methane, or cyclohexane, and may be, as described above, any hydrocarbon or a derivative thereof. Examples of the hydrocarbon or a derivative thereof, which is a raw material (substrate), are as described above, for example.

In the first aspect of the present invention, for example, as shown in the following scheme A, the raw material is represented by the following chemical formula (A1), and the oxidation reaction product of the raw material may be at least one of an alcohol represented by the following chemical formula (A2) and a carboxylic acid represented by the following chemical formula (A3). In the scheme A, Rs are each any atom or atomic group, and may be, for example, a hydrogen atom, a hydrocarbon group, or a derivative thereof. The hydrocarbon group can be any hydrocarbon group, and may be, for example, a straight-chain or branched saturated or unsaturated hydrocarbon group that may or may not contain a ring structure. The ring structure may be, for example, an aromatic ring or a non-aromatic ring. Furthermore, for example, in the scheme A, the oxidation reaction product may contain aldehyde in addition to or instead of at least one of alcohol and carboxylic acid.

Scheme A

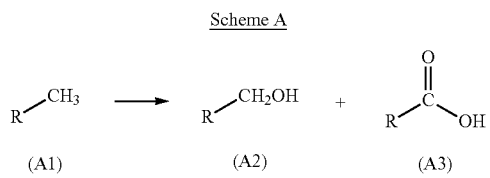

In the scheme A, in the case where a raw material (substrate) (A1) is methane, for example, as shown in the scheme A1, an oxidation reaction product may contain at least one of methanol and formic acid. In the case where a raw material (substrate) (A1) is ethane, for example, as shown in the scheme A2, an oxidation reaction product may contain at least one of ethanol and acetic acid. It is to be noted, however, that the schemes A1 and A2 are merely illustrative examples and the oxidation reaction of methane or ethane is not limited thereto in the production method of the present invention.

Scheme A1

Scheme A2

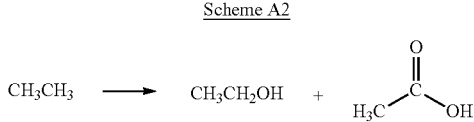

Furthermore, for example, as shown in the following scheme B, the raw material is represented by the following chemical formula (B1), and the oxidation reaction product of the raw material may be at least one of an alcohol represented by the following chemical formula (B2) and a carbonyl compound (e.g., ketone) represented by the following chemical formula (B3). In the scheme B, Rs are each any atom or atomic group, and may be, for example, a hydrocarbon group or a derivative thereof. The hydrocarbon group can be any hydrocarbon group, and may be, for example, a straight-chain or branched saturated or unsaturated hydrocarbon group that may or may not contain a ring structure. The ring structure may be, for example, an aromatic ring or a non-aromatic ring. Rs may be identical to or different from each other. Furthermore, for example, in each of the following chemical formulae (B1), (B2), and (B3), two Rs may together form a ring structure with a carbon atom to which Rs are bound.

Scheme B

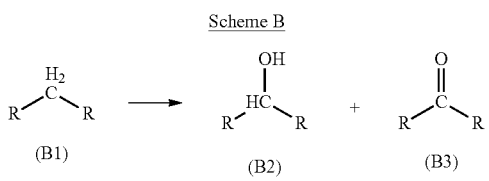

In the scheme B, in the case where a raw material (substrate) (B1) is cyclohexane, for example, as shown in the scheme B1, an oxidation reaction product may contain at least one of cyclohexanol and cyclohexanone. It is to be noted, however, that the scheme B1 is merely an illustrative example and the oxidation reaction of cyclohexane is not limited thereto in the production method of the present invention.

Scheme B1

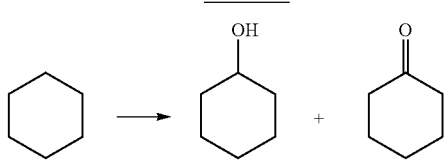

In the present invention, for example, as shown in the following scheme C, the raw material is an aromatic compound represented by the following chemical formula (C1), and the oxidation reaction product of the aromatic compound may be at least one of phenol represented by the following chemical formula (C2) and quinone represented by the following chemical formula (C3). In the scheme C, Rs are each any atom or atomic group, and may be, for example, a hydrogen atom, a hydrocarbon group, or a derivative thereof. The hydrocarbon group can be any hydrocarbon group, and may be, for example, a straight-chain or branched saturated or unsaturated hydrocarbon group that may or may not contain a ring structure. The ring structure may be, for example, an aromatic ring or a non-aromatic ring. Rs may be identical to or different from each other. Furthermore, for example, in each of the following chemical formulae (C1), (C2), and (C3), two Rs may together form a ring structure with a benzene ring to which Rs are bound. It is to be noted, however, that the scheme C is merely an illustrative example and does not limit the present invention. In other words, as described above, in the production method of the present invention, a raw material (substrate) aromatic compound is not limited to the following chemical formula (C1), and the oxidation reaction product of the aromatic compound is not limited to the following formulae (C2) and (C3).

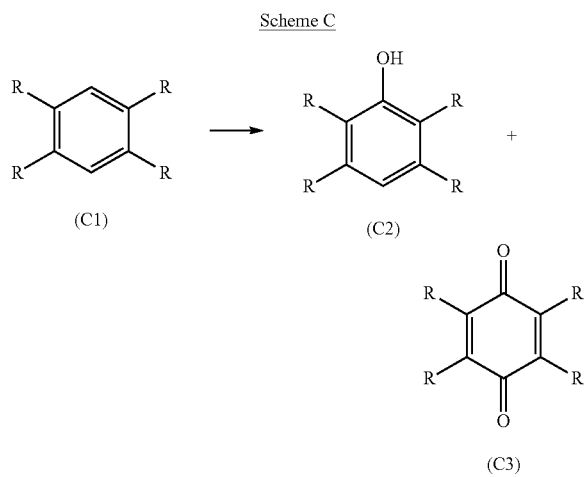

Scheme C (C1)   (C2)

(C3)

In the scheme C, in the case where a raw material (substrate) (C1) is benzene, for example, as shown in the scheme C1, an oxidation reaction product may contain at least one of hydroxy benzene and p-benzoquinone. It is to be noted, however, that the scheme C1 is merely an illustrative example and the oxidation reaction of benzene is not limited thereto in the production method of the present invention.

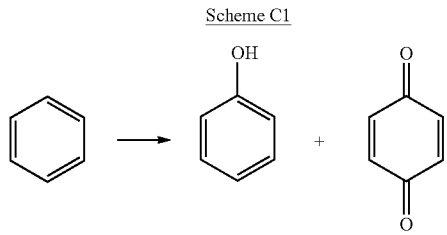 [SMILES: c1ccccc1 ; Oc1ccccc1 ; O=C1C=CC(=O)C=C1]

Scheme C1

In the case where the raw material (substrate) is an aromatic compound, it is preferable that an electron donor group is bound to an aromatic ring of the raw material aromatic compound, because this allows an oxidation reaction (including an oxidative substitution reaction) of the raw material aromatic compound to proceed more easily. The number of the electron donor groups may be one or more, and the electron donor group with a strong electron-donating property is preferable. More specifically, it is more preferable that the raw material aromatic compound is such that at least one substituent selected from the group consisting of —OR$^{100}$, —NR$^{200}_2$, and AR$^{100}$ is covalently bound to the aromatic ring. R$^{100}$ is a hydrogen atom or any substituent, and when a plurality of R$^{100}$s are present, they may be identical to or different from each other. R$^{200}$s are each a hydrogen atom or any substituent, and they may be identical to or different from each other. AR$^{100}$ is an aryl group, and when a plurality of AR$^{100}$s are present, they may be identical to or different from each other.

AR$^{100}$ may be a group derived from any aromatic ring such as a benzene ring, a naphthalene ring, an anthracene ring, a phenanthrene ring, a pyridine ring, a thiophene ring, or a pyrene ring. The aromatic ring further may have one or more substituents thereon, and when a plurality of substituents are present, they may be identical to or different from each other. AR$^{100}$ may be a phenyl group, for example.

R$^{100}$ preferably is at least one selected from the group consisting of a hydrogen atom, alkyl groups, aryl groups, and acyl groups. The alkyl group preferably is a straight-chain or branched alkyl group having 1 to 6 carbon atoms, and a methyl group is particularly preferable. The acyl group preferably is a straight-chain or branched acyl group having 1 to 6 carbon atoms. The aryl group is the same as AR$^{100}$, for example, and is a phenyl group, for example.

R$^{200}$ preferably is at least one selected from the group consisting of a hydrogen atom, alkyl groups, aryl groups, and acyl groups. The alkyl group preferably is a straight-chain or branched alkyl group having 1 to 6 carbon atoms, and a methyl group is particularly preferable. The acyl group preferably is a straight-chain or branched acyl group having 1 to 6 carbon atoms. The aryl group is the same as AR$^{100}$, for example, and is a phenyl group, for example. As —NR$^{200}_2$, an amino group substituted with an electron donor substituent, such as a dimethylamino group or a diphenylamino group, is preferable because of its particularly high electron-donating property.

Furthermore, the raw material (substrate) aromatic compound may be such that, for example, a substituent such as an alkyl group is covalently bound to the aromatic ring, and the substituent may be oxidized in the reaction step. For example, the oxidizing agent may contain an oxygen atom, the raw material aromatic compound may contain a methylene group (—CH$_2$—) covalently bound to the aromatic ring, and in the reaction step, the methylene group (—CH$_2$—) may be converted to a carbonyl group (—CO—) by oxidation. In this case, an atom or atomic group that is bound to the methylene group and the carbonyl group is not particularly limited, and examples thereof include a hydrogen atom, alkyl groups, and aryl groups. The alkyl group preferably is a straight-chain or branched alkyl group having 1 to 6 carbon atoms. The alkyl group and aryl group may further be substituted with one or more substituents. When they are substituted with a plurality of substituents, the substituents may be identical to or different from each other. For example, the methylene group becomes a methyl group (—CH$_3$) when hydrogen is bound thereto, and it becomes a formyl group (—CHO) after oxidation. The methylene group becomes an ethyl group (—CH$_2$CH$_3$) when a methyl group is bound thereto, and it becomes an acetyl group (—COCH$_3$) after oxidation. The methylene group becomes a benzyl group (—CH$_2$Ph) when a phenyl group is bound thereto, and it becomes a benzoyl group (—COPh) after oxidation. Furthermore, for example, the substituent (before oxidization) that is covalently bound to an aromatic ring is a formyl group (—CHO), and it may become a carboxy group (—COOH) after oxidization.

Furthermore, for example, the raw material (substrate) may be an olefin, and the olefin may be, for example, an aromatic olefin or an aliphatic olefin. The olefin may be an olefin represented by the following chemical formula (D1) in the following scheme D, for example. Furthermore, the oxidation reaction product of the olefin is not particularly limited, and, for example, may contain at least one of an epoxide and a diol as in the following scheme D. In each of the following chemical formulae (D1), (D2), and (D3), Rs each may be a hydrogen atom or any substituent, and Rs may be identical to or different from each other. The arbitrary substituent may be, for example, an alkyl group, an unsaturated aliphatic hydrocarbon group, an aryl group, a heteroaryl group, a halogen, a hydroxy group (—OH), a mercapto group (—SH), or an alkylthio group (—SR and R are each an alkyl group), and the substituent may or may not be substituted with another substituent. The alkyl group preferably is a straight-chain or branched alkyl group having 1 to 6 carbon atoms. Furthermore, the olefin, which is a substance to be oxidized, may be an olefin containing one olefin bond (carbon-carbon double bond) or an olefin containing two or more olefin bonds.

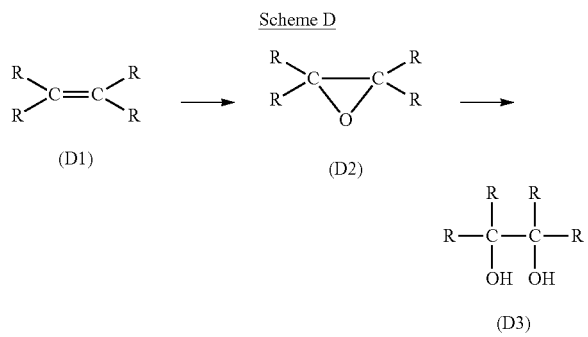

The olefin may be, for example, an aromatic olefin. That is, for example, in the chemical formula (D1), at least one of Rs may be an aromatic ring (an aryl group or a heteroaryl group). In the present invention, the aromatic olefin is not particularly limited. It is preferable that an electron donor group is bound to an aromatic ring of the aromatic olefin, for example, because this allows an oxidation reaction (including an oxidative substitution reaction) of the aromatic olefin to proceed more easily. The number of the electron donor groups may be one or more, and the electron donor group with a strong electron-donating property is preferable. More specifically, it is more preferable that the aromatic olefin is such that at least one substituent selected from the group consisting of —OR$^{100}$, —NR$^{200}_{2}$, and AR$^{100}$ is covalently bound to the aromatic ring.

In the production method of the oxidation reaction product of the first aspect of the present invention, the olefin may be at least one selected from the group consisting of ethylene, propylene, styrene, and butadiene. Furthermore, the oxidation reaction product may be, as described above, at least one of an epoxide and a diol, for example. The examples thereof are shown in the following schemes D1 to D3. It is to be noted, however, that the schemes D1 to D3 are merely illustrative examples, and the oxidation reactions of ethylene, propylene and styrene are not limited thereto in the present invention.

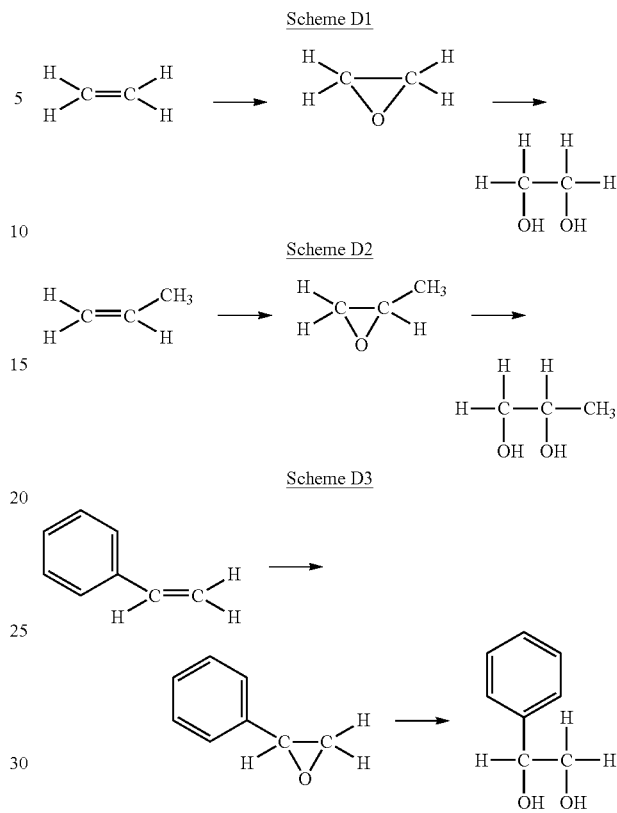

It is to be noted that, in the production method of the first to fourth aspects of the present invention, the ratio between the oxidation reaction products to be obtained (for example, the ratio between alcohol and carboxylic acid and the ratio between phenol and quinone in the first aspect of the present invention, the ratio between methanol and formic acid in the second aspect of the present invention, the ratio between ethanol and acetic acid in the third aspect of the present invention, and the ratio between cyclohexanol and cyclohexanone in the fourth aspect of the present invention) can be adjusted by setting reaction conditions as appropriate.

Furthermore, in the production method of the first aspect of the present invention, the oxidation reaction product of the raw material (substrate) is not limited to the alcohol, carboxylic acid, aldehyde, ketone, phenol, quinone, and the like. For example, in addition to or instead of these, the oxidation reaction product may contain a chlorinated product of the raw material (substrate). It is to be noted that, for example, in the case where two chlorine atom radicals Cl. are involved in the vapor phase reaction of hydrocarbon (for example, the vapor phase reaction using chlorine gas Cl$_2$), it is speculated that chlorination is preferentially caused even in the presence of oxygen molecule O$_2$. In the production method of the present invention, it is speculated that although chlorine atom radicals Cl. and oxygen molecules O$_2$ are generated by degradation of chlorine dioxide radicals, because the reaction is performed in a liquid phase, chlorination of the substrate is suppressed and the alcohol, carboxylic acid, aldehyde, ketone, phenol, quinone, and the like are preferentially generated. It is to be noted, however, that these speculations are merely illustrative examples and by no means limit the present invention. Furthermore, according to the present invention in which the reaction is performed in a biphasic system containing an aqueous phase and an organic phase, even the oxidation reaction of hydrocarbon gas (e.g., methane, ethane, etc.), which has been difficult to be performed in a liquid phase, can be performed efficiently in a liquid phase. Thus, an oxidation reaction product (e.g., methanol, formic acid, ethanol, acetic acid, etc.) of the hydrocarbon gas of great use in terms of industrial application can be produced efficiently from the hydrocarbon gas.

Furthermore, in the production method of the second aspect of the present invention, the oxidation reaction product of the raw material (substrate) methane is not limited to the methanol, formic acid, formaldehyde, methyl hydroperoxide, and the like. For example, in addition to or instead of these, the oxidation reaction product may contain a chlorinated product of the raw material (substrate) methane. It is to be noted that, for example, in the case where two chlorine atom radicals Cl. are involved in the vapor phase reaction of hydrocarbon (for example, the vapor phase reaction using chlorine gas $Cl_2$), it is speculated that chlorination is preferentially caused even in the presence of oxygen molecule $O_2$. In the production method of the present invention, it is speculated that although chlorine atom radicals Cl. and oxygen molecules $O_2$ are generated by degradation of chlorine dioxide radicals, because the reaction is performed in a liquid phase, chlorination of the substrate is suppressed and the methanol, formic acid, formaldehyde, methyl hydroperoxide, and the like are preferentially generated. It is to be noted, however, that these speculations are merely illustrative examples and by no means limit the present invention. Furthermore, according to the present invention in which the reaction is performed in a biphasic system containing an aqueous phase and an organic phase, even the oxidation reaction of methane, which is hydrocarbon gas that has been difficult to be performed in a liquid phase, can be performed efficiently in a liquid phase. Thus, an oxidation reaction product (e.g., methanol, formic acid, etc.) of the hydrocarbon gas of great use in terms of industrial application can be produced efficiently from the methane.

Furthermore, in the production method of the third aspect of the present invention, the oxidation reaction product of the raw material (substrate) is not limited to the ethanol, acetic acid, acetaldehyde, ethyl hydroperoxide, and the like. For example, in addition to or instead of these, the oxidation reaction product may contain a chlorinated product of the raw material (substrate). It is to be noted that, for example, in the case where two chlorine atom radicals Cl. are involved in the vapor phase reaction of hydrocarbon (for example, the vapor phase reaction using chlorine gas $Cl_2$), it is speculated that chlorination is preferentially caused even in the presence of oxygen molecule $O_2$. In the production method of the present invention, it is speculated that although chlorine atom radicals Cl. and oxygen molecules $O_2$ are generated by degradation of chlorine dioxide radicals, because the reaction is performed in a liquid phase, chlorination of the substrate is suppressed and the ethanol, acetic acid, acetaldehyde, ethyl hydroperoxide, and the like are preferentially generated. It is to be noted, however, that these speculations are merely illustrative examples and by no means limit the present invention. Furthermore, according to the present invention in which the reaction is performed in a biphasic system containing an aqueous phase and an organic phase, even the oxidation reaction of ethane, which is hydrocarbon gas that has been difficult to be performed efficiently in a liquid phase, can be performed efficiently in a liquid phase. Thus, an oxidation reaction product (e.g., ethanol, acetic acid, etc.) of ethane of great use in terms of industrial application can be produced efficiently from the hydrocarbon gas.

Furthermore, in the production method of the fourth aspect of the present invention, the oxidation reaction product of the raw material (substrate) is not limited to the cyclohexanol, cyclohexanone, cyclohexane hydroperoxide, ring-opening oxide (e.g., adipic acid), and the like. For example, in addition to or instead of these, the oxidation reaction product may contain a chlorinated product of the raw material (substrate) cyclohexane. It is to be noted that, for example, in the case where two chlorine atom radicals Cl. are involved in the vapor phase reaction of hydrocarbon (for example, the vapor phase reaction using chlorine gas $Cl_2$), it is speculated that chlorination is preferentially caused even in the presence of oxygen molecule $O_2$. In the production method of the present invention, it is speculated that although chlorine atom radicals Cl. and oxygen molecules $O_2$ are generated by degradation of chlorine dioxide radicals, because the reaction is performed in a liquid phase, chlorination of the substrate is suppressed and the cyclohexanol, cyclohexanone, cyclohexane hydroperoxide, ring-opening oxide (e.g., adipic acid), and the like are preferentially generated. It is to be noted, however, that these speculations are merely illustrative examples and by no means limit the present invention. Furthermore, according to the present invention in which the reaction is performed in a biphasic system containing an aqueous phase and an organic phase, even the oxidation reaction of cyclohexane can be performed efficiently in a liquid phase. Thus, an oxidation reaction product (e.g., cyclohexanol, cyclohexane, etc.) of cyclohexane of great use in terms of industrial application can be produced efficiently from cyclohexane.

Furthermore, after the reaction step, the step of recovering the oxidation reaction product is performed as necessary. The recovery step may be, as described above, a step of recovering the aqueous phase containing the oxidation reaction product from the reaction system, for example. This is because the oxidation reaction products such as lower alcohols and lower carboxylic acids (e.g., methanol, ethanol, formic acid, carboxylic acid, etc.) are easily dissolved in the aqueous phase. Furthermore, in the case where the oxidation reaction product is hardly dissolved in the aqueous phase and easily dissolved in the organic phase (for example, in the case where the oxidation reaction product is benzoquinone and the solvent of the organic phase is benzene), the organic phase containing the oxidation reaction product may be recovered from the reaction system. For example, in the case where the oxidation reaction product is hardly dissolved both in the aqueous phase and the organic phase, for example, the oxidation reaction product may be recovered by filtration or the like. Furthermore, the recovered oxidation reaction product is isolated and purified as necessary. The method of isolating and purifying the recovered oxidation reaction product is not particularly limited, and can be performed as appropriate by distillation, filtration, or the like according to a common organic synthesis reaction.

It is to be noted that, as described above, the reaction step in the production method of the first to fourth aspect of the present invention can be performed only in an organic phase. For example, an aqueous phase that contains a chlorine dioxide radical source such as described above is provided separately and chlorine dioxide radicals are generated in the aqueous phase (chlorine dioxide radical generating step). Subsequently, the chlorine dioxide radicals are extracted from the aqueous phase to the organic phase by liquid separation or the like. The raw material (substrate) may be added to the organic phase prior to the extraction of the chlorine dioxide radicals, simultaneously with the extraction of the chlorine dioxide radicals, or after the extraction of the chlorine dioxide radicals. Subsequently, in the state where the aqueous phase and the organic phase are separated (in the state where the organic phase alone is present) and the organic phase contains the raw material (substrate) and the chlorine dioxide radicals, the reaction step is performed by light irradiation in the manner as described above. The reaction step in the production method of the present invention, however, is preferably performed in the state where the aqueous phase and the organic phase are not separated but kept in contact with each other (in the biphasic reaction system). This brings about, for example, an advantageous effect of recovering a water-soluble oxidation reaction product from the aqueous phase without difficulty, as described above. Another advantageous effect is that, for example, when the chlorine dioxide radical generating step and the reaction step (step of generating an oxidation reaction product of a raw material) are performed simultaneously in a biphasic reaction system in which an aqueous phase contains a chlorine dioxide radical source, the high reaction efficiency can be achieved.

According to the present invention, for example, by a very simple method of simply irradiating a chlorine dioxide radical aqueous solution with light, chlorine atom radicals Cl. and oxygen molecules $O_2$ are generated and an oxidation reaction can be performed. Furthermore, by such a simple method, for example, hydrocarbon or a derivative thereof can be converted to an oxidation reaction product efficiently even under very mild conditions such as ordinary temperature and normal pressure.

Furthermore, according to the first to fourth aspects of the present invention, for example, without using a toxic heavy metal catalyst or the like, an oxidation reaction product of the raw material (hydrocarbon or a derivative thereof) can be obtained. This makes it possible to obtain the oxidation reaction product efficiently by a method with very small environmental load in addition to the advantage that the reaction can be performed under very mild conditions such as ordinary temperature and normal pressure.

Description of Embodiments of Fifth Aspect of Invention

The fifth aspect of the present invention is described more specifically below with reference to examples. The present invention, however, is not limited by the following description.

[1. Radical Generating Step, Etc.]

A method for producing an oxidation reaction product of an olefin according to the fifth aspect of the present invention, for example, includes a step of mixing at least one of a Lewis acid and Brønsted acid with a radical source to obtain a mixture. In the mixing step, any substance other than the radical source and at least one of the Lewis acid and the Brønsted acid may or may not be mixed. That is, the mixture obtained by the mixing step may or may not further contain any substance other than a radical source and at least one of a Lewis acid and a Brønsted acid. For example, a solvent is preferably further mixed in the mixing step from the viewpoint of reactivity or the like. It is to be noted that, in the present invention, a Lewis acid, a Brønsted acid, a radical source, and the like may or may not be dissolved in the "solvent". For example, after the mixing step, the radical source and at least one of the Lewis acid and the Brønsted acid may be dissolved, dispersed, or precipitated in the solvent. Furthermore, in the present invention, the "Lewis acid" denotes a substance that functions as a Lewis acid to the radical source, for example.

The method for producing an oxidation reaction product of an olefin according to the fifth aspect of the present invention includes, as described above, a step of reacting at least one of the Lewis acid and the Brønsted acid with the radical source to generate radicals. The radical generating step is a step of generating (producing) radicals by a reaction in the obtained mixture after the mixing step, for example. The mixture may be, as described above, in the form of a solution, a suspension, a colloid, or the like, for example. From the viewpoint of reactivity, the mixture is preferably in the form of a solution or a colloid, for example. In the radical producing step, for example, the mixture may be simply allowed to stand still at room temperature or, as necessary, heated or irradiated with light. The reaction temperature and reaction time in the radical producing step are not particularly limited, and can be, for example, determined as appropriate depending on the kind or the like of a reactant (raw material) and a desired product. In the case of irradiating the mixture with light, the wavelength of the light is not particularly limited, and can be, for example, determined as appropriate depending on the absorption band or the like of the reactant (raw material). It is to be noted that, the reaction time and reaction temperature can be adjusted by the concentrations of the radical source and at least one of the Lewis acid and the Brønsted acid in the mixture, for example. For example, the reaction time can be reduced by increasing the concentrations in the mixture. The present invention, however, is not limited thereto.

The concentration of at least one of the Lewis acid and the Brønsted acid is not particularly limited, and can be determined as appropriate depending on the kind or the like of the reactant (raw material), for example. Furthermore, the solvent is not particularly limited, may be, for example, water or an organic solvent, and can be selected as appropriate depending on the kind of a solute. Examples of the organic solvent include halogenated solvents such as methylene chloride, chloroform, and carbon tetrachloride; ketone such as acetone; nitrile solvents such as acetonitrile; alcohol solvents such as methanol and ethanol; acetic acid solvents; and sulfuric acid solvents. These solvents may be used alone or two or more of them may be used in combination. The acetic acid solvent and the sulfuric acid solvent may be obtained, for example, by dissolving acetic acid and sulfuric acid in water, respectively. These solvents each serve as a solvent as well as a Lewis acid or a Brønsted acid, for example. The kind of the solvent may be selected as appropriate depending on the solubility or the like of the solute (e.g., the radical source, at least one of the Lewis acid and the Brønsted acid, etc.), for example.

In the method for producing an oxidation reaction product of an olefin according to the fifth aspect of the present invention, as described above, the reaction may be performed by heating, by light irradiation without performing heating, or simply allowing the mixture to stand still at room temperature without performing heating or light irradiation to produce radicals. The definition of the "room temperature" is not particularly limited, and is, for example, 5° C. to 35° C. When the heating is unnecessary, for example, the cost of heating by an electric furnace or the like is not needed, which greatly reduces the cost of manufacturing radicals. In addition to this, when the heating is unnecessary, for example, an unexpected runaway reaction due to the radical chain reaction and accumulation of peroxide are suppressed, which increases the safety of the reaction significantly and reduces the cost. These descriptions, however, are merely illustrative examples and by no means limit the present invention.

The method for producing an oxidation reaction product of an olefin according to the fifth aspect of the present invention may further include a step of irradiating a mixture obtained by the mixing step with light, for example. Furthermore, as described above, radicals may be produced by the reaction caused by the light irradiation. The wavelength of the light is, for example, as described above. The light source is not particularly limited. For example, excitation can be performed easily by using visible light contained in natural light such as sunlight, for example. Also, for example, instead of or in addition to the natural light, a light source such as a xenon lamp, a halogen lamp, a fluorescent lamp, or a mercury lamp may or may not be used as appropriate. Furthermore, a filter that cuts wavelengths other than a necessary wavelength may or may not be used as appropriate.

In the method for producing an oxidation reaction product of an olefin according to the fifth aspect of the present invention, the Lewis acidity of the Lewis acid is, for example, 0.4 eV or more. The upper limit of the Lewis acidity is not particularly limited, and is, for example, 20 eV or less. It is to be noted that the Lewis acidity can be measured, for example, by the method described in Ohkubo, K.; Fukuzumi, S. Chem. Eur. J., 2000, 6, 4532, J. Am. Chem. Soc. 2002, 124, 10270-10271 or the method described in J. Org. Chem. 2003, 68, 4720-4726. Specifically, the Lewis acidity can be measured by the following method.

(Measurement Method of Lewis Acidity)

As to acetonitrile (MeCN) that contains cobalt tetraphenylporphyrin, saturated $O_2$, and an object whose Lewis acidity is to be measured (e.g., a cation of a metal or the like, represented by $M^{n+}$ in the following chemical reaction formula (1a)) in the following chemical reaction formula (1a), the change of the ultraviolet-visible absorption spectrum is measured at room temperature. On the basis of the obtained reaction rate constant ($k_{cat}$), the ΔE value (eV), which is an indicator of the Lewis acidity, can be calculated. The higher the $k_{cat}$, the stronger the Lewis acidity.

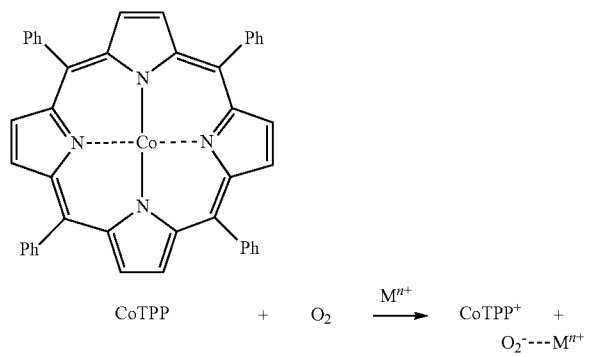

(1a)

Furthermore, in the method for producing an oxidation reaction product of an olefin according to the fifth aspect of the present invention, the Lewis acid may include one or both of metal ions and nonmetal ions, for example. The metal ion may include one or both of typical metal ions and transition metal ions. The inorganic substance may be, for example, at least one selected from the group consisting of alkali earth metal ions (e.g., $Ca^{2+}$), rare earth ions, $Mg^{2+}$, $Sc^{3+}$, $Li^+$, $Fe^{2+}$, $Fe^{3+}$, $Al^{3+}$, silicate ions, and borate ions. Examples of the alkali earth metal ion include ions of calcium, strontium, barium, and radium. More specifically, examples of the alkali earth metal ion include $Ca^{2+}$, $Sr^{2+}$, $Ba^{2+}$, and $Ra^{2+}$. Furthermore the "rare earth metal" is a generic name of a set of seventeen elements, specifically, two elements such as scandium$_{21}$Sc and yttrium$_{39}$Y and fifteen elements (lanthanoids) from lanthanum$_{57}$La to lutetium$_{71}$Lu. Examples of the rare earth ion include corresponding trivalent cations of seventeen elements.

The Lewis acid (including the counter ion) may be, for example, at least one selected from the group consisting of $AlCl_3$, $AlMeC_2$, $AlMe_2Cl$, $BF_3$, $BPh_3$, $BMe_3$, $TiC_4$, $SiF_4$, and $SiC_4$. It is to be noted that the "Ph" indicates a phenyl group and the "Me" indicates a methyl group.

In the method for producing an oxidation reaction product of an olefin according to the fifth aspect of the present invention, the acid dissociation constant $pK_a$ of the Brønsted acid is, for example, 5 or more. The upper limit of the $pK_a$ is not particularly limited and is, for example, 50 or less.

In the method for producing an oxidation reaction product of an olefin according to the fifth aspect of the present invention, the radical source may include at least one selected from the group consisting of halogen ions, hypohalite ions, halite ions, halate ions, and perhalate ions, for example. Particularly preferably, the radical source includes a chlorite ion, for example. The radical source may include oxoacid or salt thereof (e.g., halogen oxoacid or salt thereof), for example. Examples of the oxoacid include boric acid, carbonic acid, orthocarbonic acid, carboxylic acid, silicic acid, nitrous acid, nitric acid, phosphorous acid, phosphoric acid, arsenic acid, sulfurous acid, sulfuric acid, sulfonic acid, sulfinic acid, chromic acid, dichromic acid, and permanganic acid. Examples of the halogen oxoacid include chlorine oxoacids such as hypochlorous acid, chlorous acid, chloric acid, and perchloric acid; bromine oxoacids such as hypobromous acid, bromous acid, bromic acid, and perbromic acid; and iodine oxoacids such as hypoiodous acid, iodous acid, iodic acid, and periodic acid. The radical source may be selected as appropriate by taking the intensity of the reactivity of a radical species into consideration according to the application, for example. For example, hypochlorous acid exhibiting high reactivity or chlorous acid exhibiting somewhat lower reactivity than the hypochlorous acid and allowing a reaction to be controlled more easily may be selectively used according to the application.

Furthermore, in the method for producing an oxidation reaction product of an olefin according to the fifth aspect of the present invention, when a compound (e.g., an olefin serving as a substance to be oxidized) has isomers such as tautomers and stereoisomers (e.g., a geometric isomer, a conformer, and an optical isomer), any isomer can be used in the present invention, unless otherwise stated. Furthermore, when a compound (e.g., an olefin, etc.) can form a salt, the salt can be used in the present invention, unless otherwise stated. The salt may be an acid addition salt or a base addition salt. Moreover, an acid that forms the acid addition salt may be either an inorganic acid or an organic acid, and a base that forms the base addition salt may be either an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxides, alkali metal hydroxides, alkaline-earth metal hydroxides, carbonates, and hydrogencarbonates. More specifically, the inorganic base may be, for example, sodium hydroxide, potassium hydroxide, potassium carbonate, sodium carbonate, sodium hydrogencarbonate, potassium hydrogencarbonate, calcium hydroxide, and calcium carbonate. The organic base also is not particularly limited, and examples thereof include ethanolamine, triethylamine, and tris(hydroxymethyl)aminomethane. The method for producing these salts also is not particularly limited. For example, they can be produced by adding an acid or a base such as described above to the compound as appropriate by a known method.

Moreover, in the method for producing an oxidation reaction product of an olefin according to the fifth aspect of the present invention, a chain substituent (e.g., an alkyl group, hydrocarbon groups such as an unsaturated aliphatic hydrocarbon group, etc.) may be straight-chain or branched, unless otherwise stated, and the number of carbons thereof is not particularly limited, and may be, for example, 1 to 40, 1 to 32, 1 to 24, 1 to 18, 1 to 12, 1 to 6, or 1 to 2 (at least 2 in the case of an unsaturated hydrocarbon group). Furthermore, in the present invention, as to a cyclic group (e.g., an aryl group, a heteroaryl group, etc.), the number of ring members (the number of carbons that compose a ring) is not particularly limited and may be, for example, to 32, 5 to 24, 6 to 18, 6 to 12, or 6 to 10. When a substituent or the like has isomers, any isomer can be used, unless otherwise stated. For example, in the case of simply describing as a "naphthyl group", it may be a 1-naphthyl group or a 2-naphthyl group.

[2. Oxidation Reaction Step, Etc.]

The method for producing an oxidation reaction product of an olefin according to the fifth aspect of the present invention includes a step of oxidizing olefin using the radicals as an oxidizing agent as described above.

The method of conducting the method for producing an oxidation reaction product of an olefin according to the fifth aspect of the present invention is not particularly limited. For example, in the mixing step, in addition to a radical source and at least one of a Lewis acid and a Brønsted acid, the olefin may be further mixed therewith. At this time, preferably, a solvent is further mixed therewith as described above. Then, in the radical generating step, the generated radicals may react with the olefin to generate the oxidation reaction product. That is, the oxidation reaction step and the radical generating step may be performed simultaneously in the same reaction system in balance. In this case, the concentrations of the olefin, at least one of the Lewis acid and the Brønsted acid, and the radical source (the concentrations mol/l of reactants with respect to the solvent) are not particularly limited, for example, and each can be determined as appropriate. Furthermore, for example, the concentration of the substance to be oxidized (olefin) is preferably as high as possible as it accelerates the reaction rate and the concentration of the oxidizing agent (radical source) is preferably not too high as it allows smooth progress of the reaction. It is to be noted, however, that this description is merely an illustrative example, and by no means limits the present invention.

In the oxidation reaction step in the method for producing an oxidation reaction product of an olefin according to the fifth aspect of the present invention, as described above, an olefin is oxidized using the radicals as an oxidizing agent, for example. The radical source may be oxoacid and radicals generated from the oxoacid may be an oxidizing agent. As an example, the oxidation reaction product may be produced by oxidizing the substance to be oxidized using chlorite ion $ClO_2^-$ as the radical source and radicals $ClO_2$ generated from the chlorite ion $ClO_2^-$ as an oxidizing agent.

In the method for producing an oxidation reaction product of an olefin according to the fifth aspect of the present invention, the olefin serving as a substance to be oxidized is not particularly limited, and may be, for example, an aromatic olefin or an aliphatic olefin. The olefin may be, for example, an olefin represented by the following chemical formula (AA1). Furthermore, the oxidation reaction product of the olefin is not particularly limited and, for example, may contain at least one of an epoxide and a diol as in the following scheme AA. In each of the following chemical formulae (AA1), (AA2), and (AA3), Rs each may be a hydrogen atom or any substituent, and Rs may be identical to or different from each other. Examples of the arbitrary substituent include an alkyl group, an unsaturated aliphatic hydrocarbon group, an aryl group, a heteroaryl group, a halogen, a hydroxy group (—OH), a mercapto group (—SH), or an alkylthio group (—SR and R are each an alkyl group), the substituent may or may not be substituted with another substituent. The alkyl group preferably is a straight-chain or branched alkyl group having 1 to 6 carbon atoms. Furthermore, the olefin, which is a substance to be oxidized, may be an olefin containing one olefin bond (carbon-carbon double bond) or an olefin containing two or more olefin bonds.

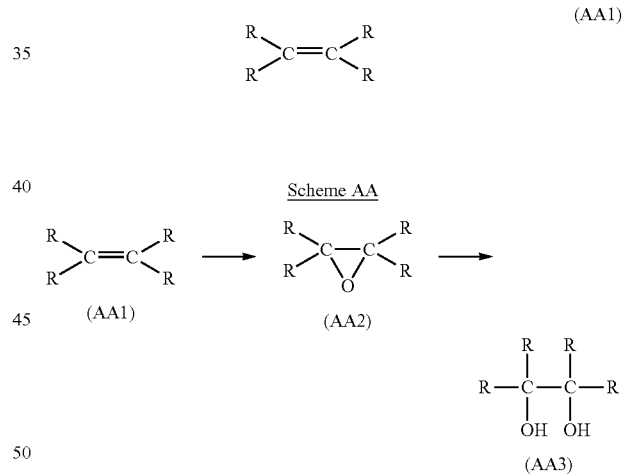

The olefin may be, for example, an aromatic olefin. That is, for example, in the chemical formula (AA1), at least one of Rs may be an aromatic ring (an aryl group or a heteroaryl group). In the present invention, the aromatic olefin is not particularly limited. It is preferable that an electron donor group is bound to an aromatic ring of the aromatic olefin, for example, because this allows an oxidation reaction (including an oxidative substitution reaction) of the raw material aromatic compound to proceed more easily. The number of the electron donor groups may be one or more, and the electron donor group with a strong electron-donating property is preferable. More specifically, it is more preferable that the raw material aromatic compound is such that at least one substituent selected from the group consisting of —$OR^{100}$, —$NR^{200}_2$, and $AR^{100}$ is covalently bound to the aromatic ring. $R^{100}$ is a hydrogen atom or any substituent, and when a plurality of $R^{100}$s are present, they may be identical to or different from each other. $R^{200}$s are each a hydrogen atom or any substituent, and they may be identical to or different from each other. $AR^{100}$ is an aryl group, and when a plurality of $AR^{100}$s are present, they may be identical to or different from each other.

$AR^{100}$ may be a group derived from any aromatic ring such as a benzene ring, a naphthalene ring, an anthracene ring, a phenanthrene ring, a pyridine ring, a thiophene ring, or a pyrene ring. The aromatic ring further may have one or more substituents thereon, and when a plurality of substituents are present, they may be identical to or different from each other. $AR^{100}$ may be a phenyl group, for example.

$R^{100}$ preferably is at least one selected from the group consisting of a hydrogen atom, alkyl groups, aryl groups, and acyl groups. The alkyl group preferably is a straight-chain or branched alkyl group having 1 to 6 carbon atoms, and a methyl group is particularly preferable. The acyl group preferably is a straight-chain or branched acyl group having 1 to 6 carbon atoms. The aryl group is the same as $AR^{100}$, for example, and is a phenyl group, for example.

$R^{200}$ preferably is at least one selected from the group consisting of a hydrogen atom, alkyl groups, aryl groups, and acyl groups. The alkyl group preferably is a straight-chain or branched alkyl group having 1 to 6 carbon atoms, and a methyl group is particularly preferable. The acyl group preferably is a straight-chain or branched acyl group having 1 to 6 carbon atoms. The aryl group is the same as $AR^{100}$ for example, and is a phenyl group, for example. As $-NR^{200}{}_2$, an amino group substituted with an electron donor substituent, such as a dimethylamino group or a diphenylamino group, is preferable because of its particularly high electron-donating property.

In the method for producing an oxidation reaction product of an olefin according to the fifth aspect of the present invention, the olefin may be at least one selected from the group consisting of ethylene, propylene, styrene, and butadiene. Furthermore, the oxidation reaction product may be, for example, at least one of an epoxide and a diol as described above. The examples of the reaction are shown in the following schemes AA1 to AA3. It is to be noted, however, that the schemes AA1 to AA3 are merely illustrative examples, and the oxidation reactions of ethylene, propylene, and, styrene are not limited thereto in the fifth aspect of the present invention.

Scheme AA1

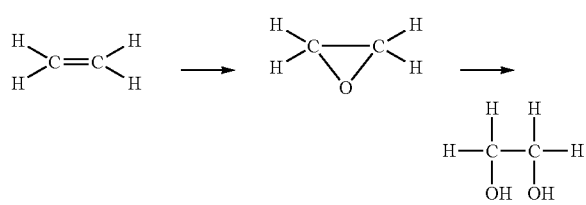

Scheme AA2

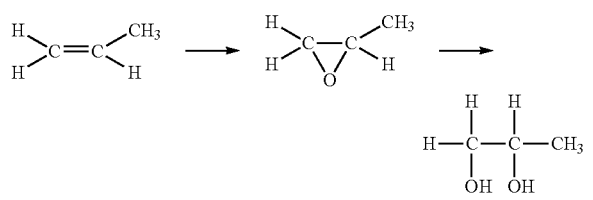

Scheme AA3

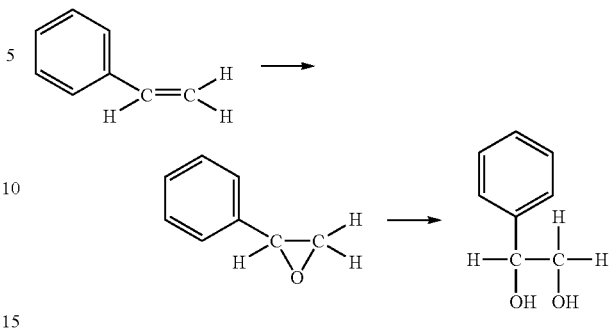

In oxidization of an olefin (for example, the olefin (AA1) in the scheme AA), for example, by adjusting the concentration of at least one of the radical source, the oxidizing agent, and at least one of the Lewis acid and Brønsted acid, oxidation reaction products can be selectively generated. For example, an epoxide is prone to be obtained when the concentrations are low with respect to the substance to be oxidized and a diol is prone to be obtained when the concentrations are high with respect to the substance to be oxidized, although the present invention is not limited thereto. Furthermore, for example, instead of changing the concentrations, by changing the intensity of the reactivity of a radical species generated from the radical source, oxidation reaction products can be selectively generated. For example, an epoxide is prone to be obtained with a radical species having low reactivity and a diol is prone to be obtained with a radical species having high reactivity, although the present invention is not limited thereto. It is to be noted that the use of the oxidation reaction product is not particularly limited. For example, when the substance to be oxidized (raw material aromatic compound) is styrene, styrene oxide can be utilized as an adhesive agent and a diol can be utilized as a perfume. As described above, the epoxide and the diol are in demand in different uses. Thus, the selective production of the epoxide and the diol by controlling the reaction condition allows the fifth aspect of the present invention to be applied to further wider uses.

EXAMPLES

Examples of the present invention are described below. It is to be noted, however, that the present invention is by no means limited to the following examples.

Examples of First to Fourth Aspects of the Present Invention

First, Examples of the first to fourth aspects of the present invention are described.

Examples 1 to 7

Figure 9:
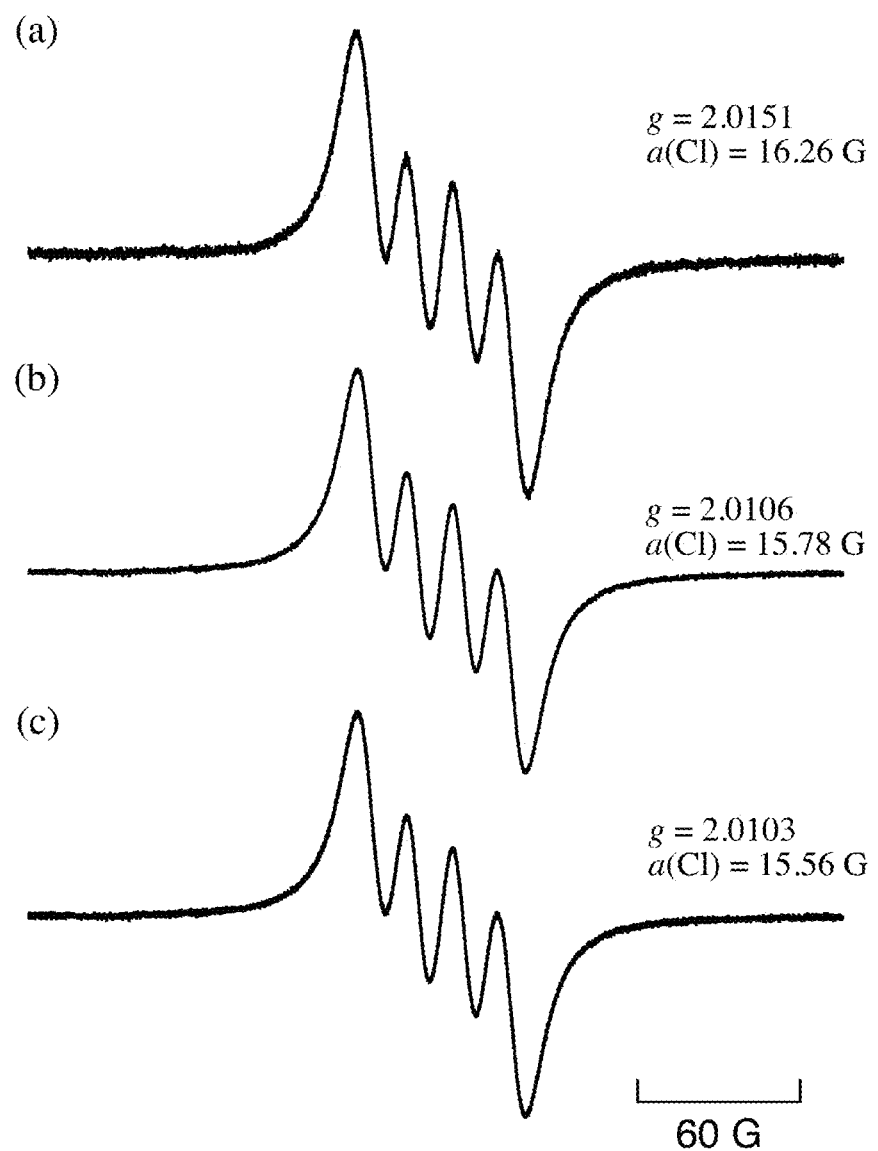
FIG. 9 shows EPR spectra of MeCN solutions measured at 298 K.

A substrate (raw material) hydrocarbon was dissolved in an organic solvent, thereby preparing an organic phase. On the other hand, sodium chlorite (NaClO$_2$) and an acid were dissolved in water (H$_2$O or D$_2$O) and the thus obtained aqueous solution was saturated with oxygen gas (O$_2$), thereby preparing an aqueous phase. Thereafter, the aqueous phase and the organic phase were added to the same reaction vessel and brought into contact with each other, thereby preparing a biphasic system. Furthermore, the biphasic system was irradiated with light in the atmosphere with a xenon lamp having a wavelength of >290 nm at room temperature (about 25° C.) without applying or reducing pressure. It is to be noted that, during the light irradiation, the biphasic system was not stirred and a water layer (aqueous phase) and an organic layer (organic phase) were kept separated. In this manner, an oxidation reaction product of the substrate (raw material) hydrocarbon was produced. Furthermore, the organic layer (organic phase) right after the light irradiation was subjected to electronic paramagnetic resonance (EPR) measurement. As a result, similarly to (b) of FIG. 9 of Example 8 (Example of the fifth aspect of the present invention) described below, peaks derived from chlorine dioxide radical ClO$_2\cdot$ were observed. Thereby, it was confirmed that the chlorine dioxide radical CO$_2$. was generated in the organic layer (organic phase).

The kind and amount (concentration) of each of a solvent (an organic solvent and water), a substrate (a raw material), and an acid, and the amount (concentration) of sodium chlorite (NaClO$_2$) used in each of Examples 1 to 7 are summarized in the following tables 1 and 2. Furthermore, the yield of each of the oxidation reaction products and the light irradiation time are also summarized in the following tables 1 and 2. It is to be noted that, in the following tables 1 and 2, "D" indicates heavy hydrogen. In Example 6, as a benzene (serving as a substrate as well as a solvent), a deuterated benzene (benzene d6) in which all six hydrogen atoms on an aromatic ring are substituted with heavy hydrogen was used. Furthermore, the conversion ratio of each of the substrates and the yield of each of the oxidation reaction products were calculated by measuring the $^1$HNMR of each of the substrates before reaction and the oxidation reaction products after reaction and comparing the peak intensity ratio of each component between them. In Example 4, each of the oxidation reaction products was isolated and purified and the weight thereof was measured. It is to be noted that, in Example 4, besides acetic acid and ethanol described in the following table 1, a trace amount of ethyl acetate speculated to be obtained by the reaction of the acetic acid and ethanol was detected.

TABLE 1

| | Solvent | Substrate (Raw Material) | Acid | NaClO$_2$ | Yield | Light irradiation time |
|---|---|---|---|---|---|---|
| Ex. 1 | CF$_3$(CF$_2$)$_4$CF$_3$ D$_2$O (4:1 v/v, 2 mL) | CH$_3$CH$_3$ (4.1 mM) | CF$_3$COOD (100 mM) | 200 mM | 70% CH$_3$COOH 17% CH$_3$CH$_2$OH | 50 min |
| Ex. 2 | CF$_3$(CF$_2$)$_4$CF$_3$ D$_2$O (4:1 v/v, 2 mL) | CH$_4$ (1.1 mM) | DCl (100 mM) | 200 mM | 76% HCOOH 14% CH$_3$OH | 60 min |
| Ex. 3 | CF$_3$(CF$_2$)$_4$CF$_3$ D$_2$O (4:1 v/v, 2 mL) | CH$_3$CH$_3$ (12 mM) | DCl (100 mM) | 200 mM | 27% CH$_3$COOH 9% CH$_3$CH$_2$OH | 30 min |
| Ex. 4 | CF$_3$(CF$_2$)$_4$CF$_3$ (100 mL) D$_2$O (26 mL) | CH$_3$CH$_3$ (excess) | DCl (200 mM) | 400 mM × 5 | 0.13 g CH$_3$COOH 0.09 g CH$_3$CH$_2$OH | 12 h |
| Ex. 5 | CDCl$_3$ D$_2$O (4:1 v/v, 2 mL) | CH$_3$CH$_3$ (20 mM) | DCl (100 mM) | 200 mM | 14% CH$_3$COOH 1.5% CH$_3$CH$_2$OH | 50 min |

TABLE 2

| | Solvent | Substrate (Raw Material) | Acid | NaClO$_2$ | Yield | Light irradiation time |
|---|---|---|---|---|---|---|
| Ex. 6 | Benzene D$_2$O (4:1 v/v, 2 mL) | Benzene | DCl | [ClO$_2$] = 4 mM (in Benzene) | 3.0% Phenol 2.2% p-Benzoquinone 1.4% Chlorobenzene 7.0% o-Chlorophenol 4.8% p-Chlorophenol (vs [ClO$_2$]$_0$) | 10 min |
| Ex. 7 | Perfluorodecalin H$_2$O (4:1 v/v, 1 mL) | Cyclohexane (1M) | Sc(OTf)$_3$ (100 mM) | 100 mM | 7% Cyclohexanol 15% Cyclohexanone (vs [NaClO$_2$]$_0$) | 24 h |

As can be seen from Examples 1 to 7, by simply conducting light irradiation in the atmosphere at ordinary temperature and normal pressure, oxidation reaction products such as alcohol, carboxylic acid, ketone, phenol, and quinone could be produced from hydrocarbon efficiently. In particular, according to Example 2, by simply conducting light irradiation in the atmosphere at ordinary temperature and normal pressure, oxidation reaction products such as methanol and formic acid could be produced from methane efficiently. According to Examples 1 and 3 to 5, by simply conducting light irradiation in the atmosphere at ordinary temperature and normal pressure, oxidation reaction products such as ethanol and acetic acid could be produced from ethane efficiently. According to Example 7, by simply conducting light irradiation in the atmosphere at ordinary temperature and normal pressure, oxidation reaction products such as cyclohexanol and cyclohexanone could be produced from cyclohexane efficiently. It is to be noted that, while a xenon lamp was used as a light source in the present examples, use of sunlight, LED, or the like as a light source achieves further energy saving and cost reduction.

Furthermore, as can be seen from Examples 1 to 7, by using hydrocarbon as a raw material (substrate), oxidation reaction products of great use in terms of industrial application can be obtained efficiently according to the present invention. For example, methanol and formic acid obtained in Example 2 and ethanol and acetic acid obtained in Examples 1 and 3 to 5 all are of great use in various applications such as fuels, solvents, and raw materials of chemical products. Furthermore, hydroxy benzene obtained in Example 6 has great use in various applications such as pharmaceutical agents and raw materials of chemical products, and p-benzoquinone obtained in Example 6 has great use in various applications such as oxidizing agents, dehydrogenating agents, and polymerization inhibitors. The mixture of cyclohexanol and cyclohexanone obtained in Example 7 are commonly known as KA oil (ketone alcohol oil). The KA oil is of great use in terms of industrial application because it can be converted to adipic acid by further oxidization and can be used as a raw material of a polyamide resin (product name: nylon). As described above, the method for producing an oxidation reaction product of great use in terms of industrial application efficiently by using hydrocarbon as a raw material (substrate) has never been reported. That is, according to the present examples, it was confirmed that the first to fourth aspects of the present invention have great superiority over conventional arts from the viewpoint of industrial utility value.

Example of Fifth Aspect of the Present Invention

Next, Example of the fifth aspect of the present invention is described.

Example 8

In the present example, it was confirmed that efficient dihydroxylation of styrene can be performed by scandium triflate and sodium chlorite. Specifically, by the dihydroxylation of styrene by scandium triflate and chlorite ions ($ClO_2^-$) at ordinary temperature and normal pressure, 1-phenylethane-1,2-diol could be produced efficiently. It was confirmed that the scandium triflate working as a strong Lewis acid generates chlorine dioxide radicals ($ClO_2\cdot$) from the chlorite ions ($ClO_2^-$) and increases the reactivity of the chlorine dioxide radicals ($ClO_2\cdot$).

Oxidization of an olefin to a 1,2-diol is an important industrial process for producing precursors of various kinds of chemical substances such as resins, pharmaceutical agents, dyes, insecticides, and perfume compounds in the fields of fine chemicals and speciality chemicals. Several methods for converting olefins to corresponding epoxides and alcohols by oxidization using inorganic metal oxo complexes and metallic oxides having heavy atoms have been reported. High-valent $Os^{VIII}O_4$ is an effective and selective reagent for oxidizing an olefin to a 1,2-diol (References, etc. 1 to 8 [the same as Non Patent Literatures 7 to 14]). However, the toxicity, sublimation property, and waste of the osmium compound cause serious problems. Sodium chlorite ($NaClO_2$) is a non-toxic inexpensive oxidizing reagent and has been used as a precursor of a chlorine dioxide radical ($ClO_2\cdot$) (References, etc. 9 to 12 [the same as Non Patent Literatures 15 to 18]). $ClO_2\cdot$ is known as a reactive stable radical. $ClO_2\cdot$, however, is an explosive gas which is yellow at room temperature. $ClO_2\cdot$ can be experimentally prepared by oxidization of $NaClO_2$ by $Cl_2$ and reaction of chloric acid potassium ($KClO_3$) and oxalic acid (Reference, etc. 13). These methods cause serious problems such as the toxicity of $Cl_2$ and the explosivity of $ClO_3^-$. There has been an attempt on epoxidation of an olefin using $NaClO_2$ as a precursor of $ClO_2\cdot$. However, because the oxidization ability of $ClO_2\cdot$ was not strong enough to oxidize an olefin to a diol in the absence of an acid, a 1,2-diol product could not be obtained (References, etc. 14 to 17). The activation of Cl=O double bond of $ClO_2\cdot$ is a key for selectively dihydroxylating an olefin in one step.

The present example reports an efficient synthesis method of a dihydroxylated product of styrene at ordinary temperature and normal pressure by the activation of $ClO_2\cdot$ using scandium triflate [$Sc(OTf)_3$] as a Lewis acid (Reference, etc. 18). The mechanism of dihydroxylation was disclosed on the basis of the detection of a radical intermediate by the EPR and UV-Vis absorption spectroscopy.

Figure 11:
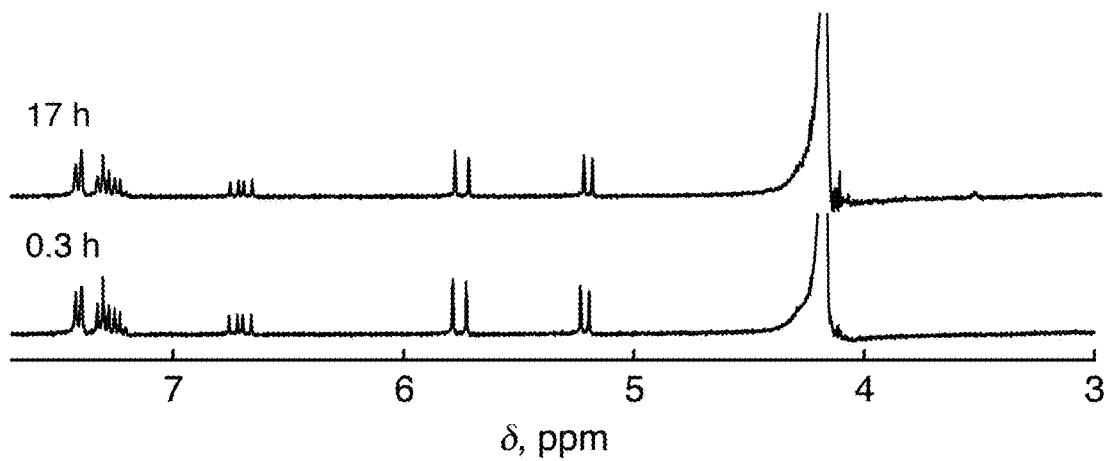
FIG. 11 is a spectral diagram showing the result of tracing the reaction of styrene (2.0 mM) by $NaClO_2$ (20 mM) in an aqueous MeCN solution ($MeCN/H_2O$ 1:1 v/v) at room temperature (25° C.) utilizing $^1HNMR$.
Figure 12:
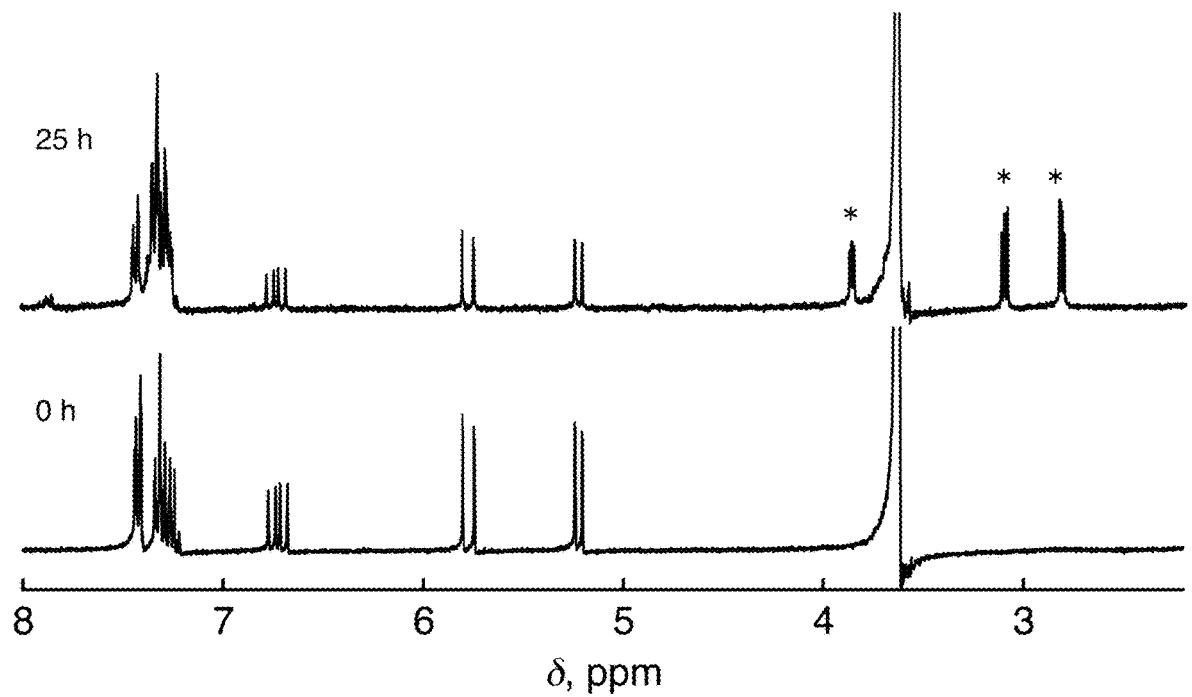
FIG. 12 shows $^1HNMR$ spectra of $CD_3CN/D_2O$ (4:1 v/v) that contains styrene (66 mM) and $NaClO_2$ (200 mM) at 60° C. (333 K) collected 0 hours and 25 hours after mixing. The mark "*" indicates the peak derived from styrene oxide.
Figure 13:
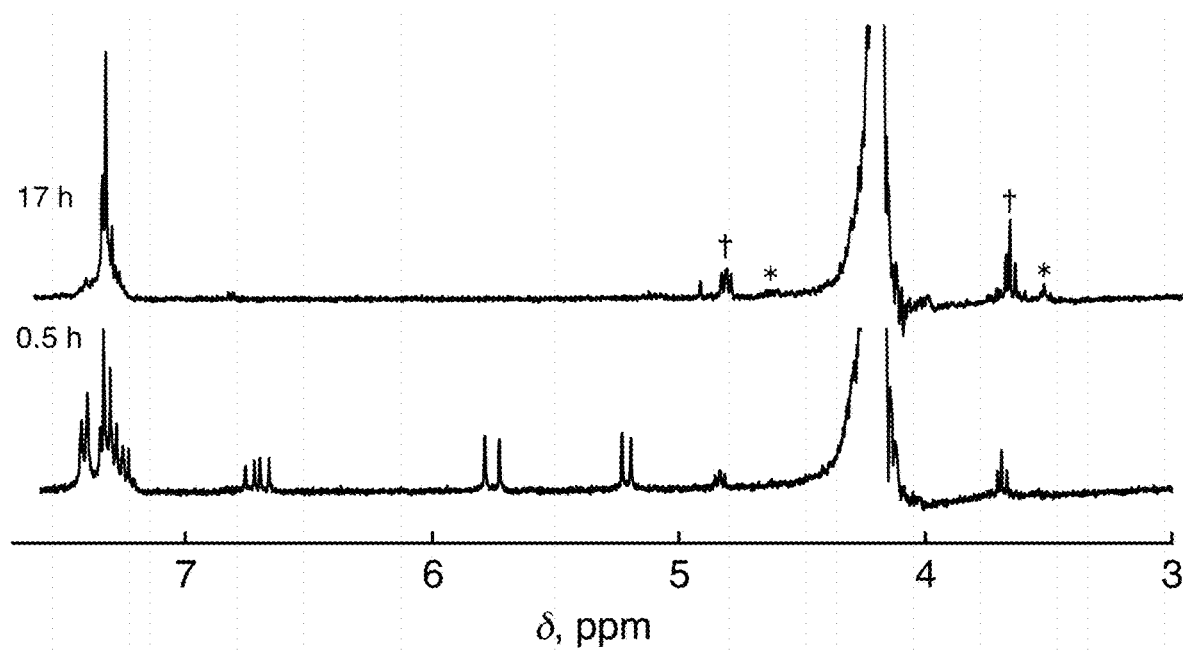
FIG. 13 shows $^1HNMR$ spectra of $CD_3CN/D_2O$ (1:1 v/v) that contains styrene (2.0 mM), $NaClO_2$ (20 mM), and $Sc(OTf)_3$ (30 mM) at 25° C. collected 0.6 hours and 17 hours after mixing. The mark "*" and the mark "†" indicate the peak derived from 1-phenylethane-1,2-diol and the peak derived from 2-chloro-1-phenylethanol, respectively.
Figure 14:
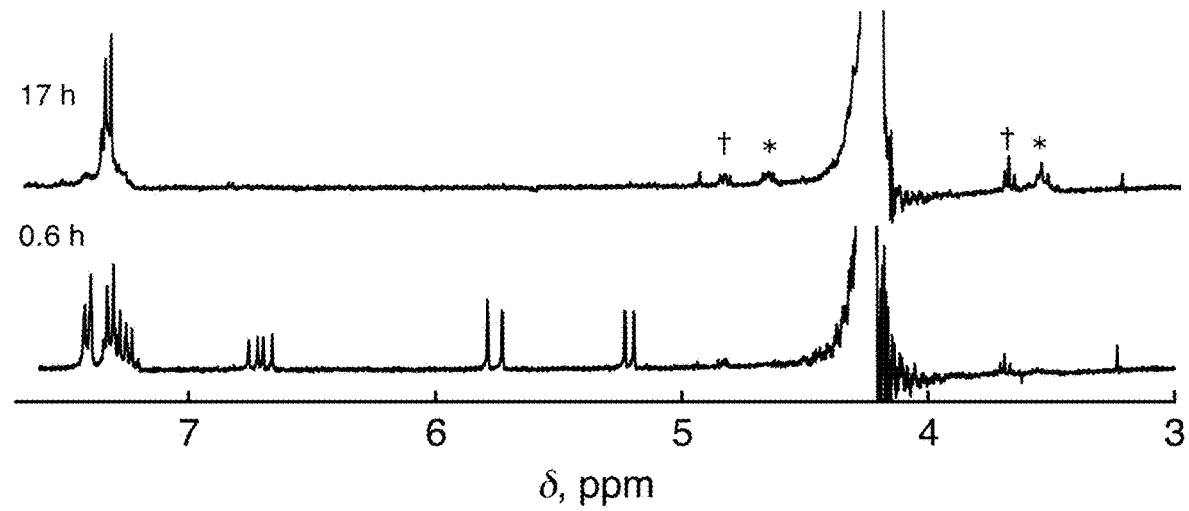
FIG. 14 shows $^1HNMR$ spectra of $CD_3CN/D_2O$ (1:1 v/v) that contains styrene (2.0 mM), $NaClO_2$ (20 mM), and $CF_3COOD$ (30 mM) collected 0.5 hours and 17 hours after mixing. The mark "*" and the mark "†" indicate the peak derived from 1-phenylethane-1,2-diol and the peak derived from 2-chloro-1-phenylethanol, respectively.
Figure 18:
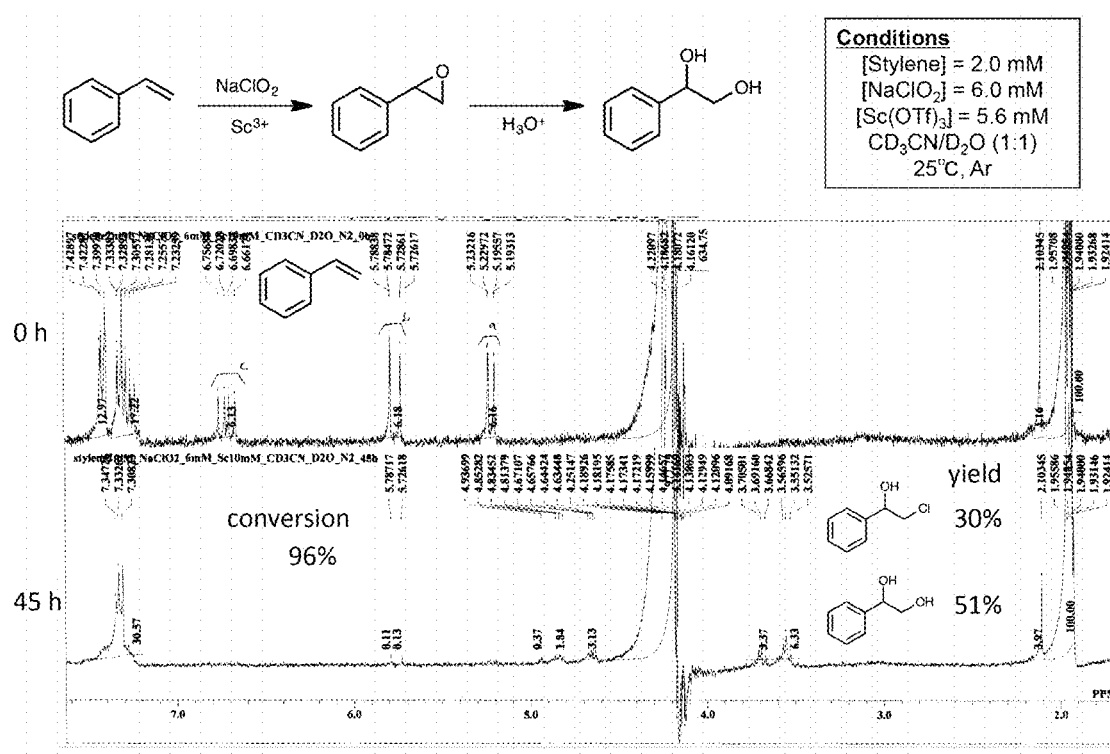
FIG. 18 shows $^1HNMR$ spectra of $CD_3CN/D_2O$ (1:1 v/v) that contains styrene (2.0 mM), $NaClO_2$ (6.0 mM), and $Sc(OTf)_3$ (5.6 mM) at 25° C. in the Ar atmosphere collected 0 hours and 45 hours after mixing.

In the reaction of styrene (2.0 mM) by $NaClO_2$ (20 mM) in an aqueous MeCN solution ($MeCN/H_2O$ 1:1 v/v) at room temperature (25° C.), dihydroxylation of styrene was not caused (see FIG. 11). FIG. 11 shows the results obtained by performing the above-described reaction using a $^1HNMR$ spectrum measurement solvent $CD_3CN/D_2O$ (1:1 v/v) as $MeCN/H_2O$ and tracing the reaction utilizing $^1HNMR$. FIG. 11 shows the $^1HNMR$ spectra of $CD_3CN/D_2O$ (1:1 v/v) collected 0.3 hours and 17 hours after the start of the reaction. When the temperature was increased to 333 K, a dihydroxylated product was not formed but epoxidation was caused (FIG. 12) (References, etc. 14 and 19). FIG. 12 shows the $^1HNMR$ spectra of $CD_3CN/D_2O$ (4:1 v/v) that contains styrene (66 mM) and $NaClO_2$ (200 mM) at 60° C. (333 K) collected 0 hours and 25 hours after mixing. The mark "*" indicates the peak derived from styrene oxide. In contrast, in the case where $CF_3COOH$ (30 mM) as a Brønsted acid was added as an additive, an epoxide was not formed at all 17 hours after mixing, instead, 1-phenylethane-1,2 diol (1) and 2-chloro-1-phenylethanol (2) were produced at the yield of 15% and 69%, respectively [reaction formula (1)]. They were measured utilizing the $^1HNMR$ spectrum (FIG. 13) (Reference, etc. 20). FIG. 13 shows the $^1HNMR$ spectra of $CD_3CN/D_2O$ (1:1 v/v) that contains styrene (2.0 mM), $NaClO_2$ (20 mM), and $Sc(OTf)_3$ (30 mM) at 25° C. collected 0.6 hours and 17 hours after mixing. The mark "*" and the mark "†" indicate the peak derived from 1-phenylethane-1,2-diol, and the peak derived from 2-chloro-1-phenylethanol, respectively. FIG. 14 shows the $^1HNMR$ spectra of $CD_3CN/D_2O$ (1:1 v/v) that contains styrene (2.0 mM), $NaClO_2$ (20 mM), and $CF_3COOD$ (30 mM) collected 0.5 hours and 17 hours after mixing. The mark "*" and the mark "†" indicate the peak derived from 1-phenylethane-1,2-diol and the peak derived from 2-chloro-1-phenylethanol, respectively. FIG. 18 shows the $^1HNMR$ spectra of $CD_3CN/D_2O$ (1:1 v/v) that contains styrene (2.0 mM), $NaClO_2$ (6.0 mM), and $Sc(OTf)_3$ (5.6 mM) at 25° C. in the Ar atmosphere collected 0 hours and 45 hours after mixing. As shown in FIG. 18, when $Sc(OTf)_3$ (30 mM) which is a strong Lewis acid was used instead of $CF_3COOH$, the yield of diol (1) was remarkably increased to 51% [see the following reaction formula (1)] (FIG. 18) (Reference, etc. 21).

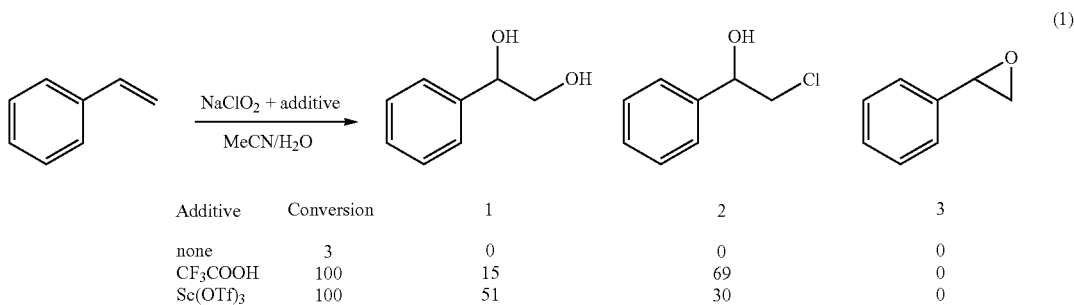

(1)

| Additive | Conversion | 1 | 2 | 3 |
|---|---|---|---|---|
| none | 3 | 0 | 0 | 0 |
| CF$_3$COOH | 100 | 15 | 69 | 0 |
| Sc(OTf)$_3$ | 100 | 51 | 30 | 0 |

Figure 6:
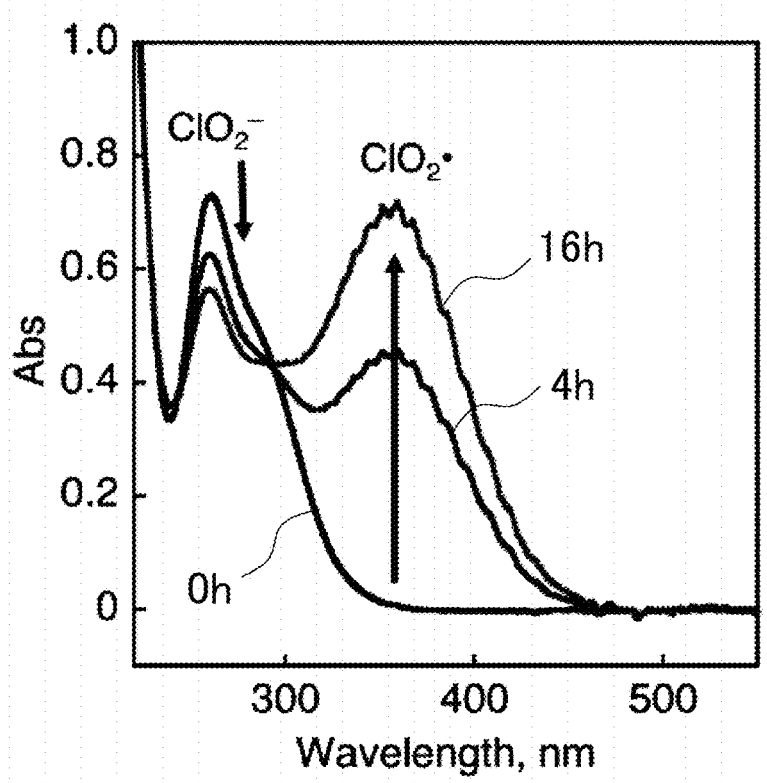
FIG. 6 shows an ultraviolet-visible absorption spectrum of $NaClO_2$ (5.0 mM) collected 0, 4, and 16 hours after mixing with $Sc(OTf)_3$ (10 mM) in an aqueous solution at 298 K.
Figure 7A:
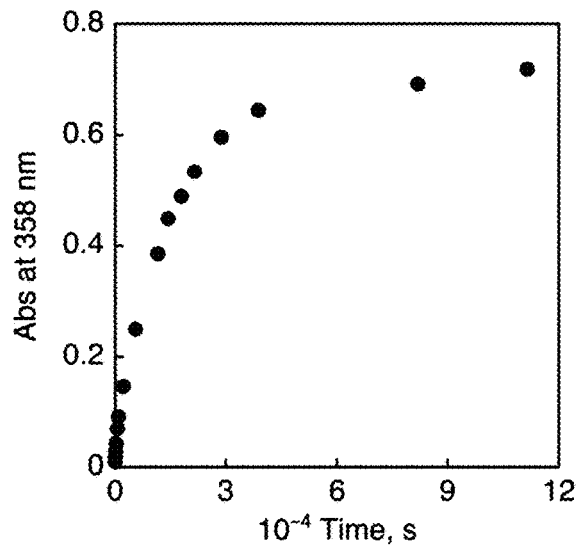
FIG. 7A shows a time profile of UV-Vis absorption at 358 nm in formation of $Sc^{3+}(ClO_2 \cdot)$ by a reaction between $Sc(OTf)_3$ (10 mM) and $NaClO_2$ (5.0 mM) in an aqueous solution (0.20 M acetate buffer having a pH of 2.9) at 298 K.
Figure 7B:
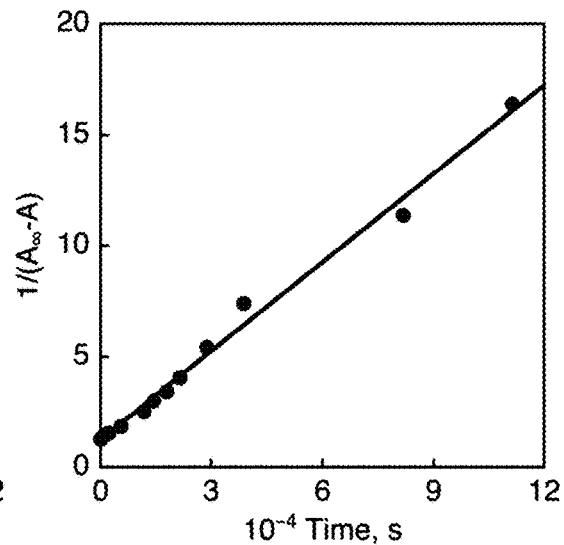
FIG. 7B shows a secondary plot.

The UV-Vis absorption spectroscopy was adopted for clarifying the reaction mechanism and the detection of a reactive intermediate. As shown in FIG. 6, NaClO$_2$ showed the absorption band at 260 nm in an aqueous solution. The absorption band was quenched by adding Sc(OTf)$_3$ (10 mM), and in accordance with this, a new absorption band was increased at 358 nm, and it was identified (assigned) that this absorption band was based on ClO$_2$. (References, etc. 22, 23). Also in the presence of CF$_3$COOH, a similar change of the absorption spectrum was measured (Reference, etc. 24). FIG. 6 shows the change of occurrence of the absorption band at 358 nm with time. FIG. 6 shows the ultraviolet-visible absorption spectrum of NaClO$_2$ (5.0 mM) collected 0, 4, and 16 hours after mixing with Sc(OTf)$_3$ (10 mM) in an aqueous solution at 298 K. In FIG. 6, the horizontal axis indicates a wavelength (nm) and the vertical axis indicates an absorbance. FIG. 7A shows a time profile of UV-Vis absorption at 358 nm in the same reaction as shown in FIG. 6 (formation of Sc$^{3+}$(ClO$_2^-$) by a reaction between Sc(OTf)$_3$ (10 mM) and NaClO$_2$ (5.0 mM) in an aqueous solution (0.20 M acetate buffer having a pH of 2.9) at 298 K). In FIG. 7A, the horizontal axis indicates a time (second) and the vertical axis indicates an absorbance at 358 nm. FIG. 7B shows the secondary plot of the measurement result of FIG. 7A. The time profile (FIG. 7A) meets the secondary plot (FIG. 7B) well. In generation of ClO$_2$. using Sc(OTf)$_3$, two molecules of ClO$_2^-$ are involved in the rate-determining step (see below). The rate constant of the two molecules was determined as 0.16M$^{-1}$s$^{-1}$ based on the slope of the straight line.

Figure 8A:
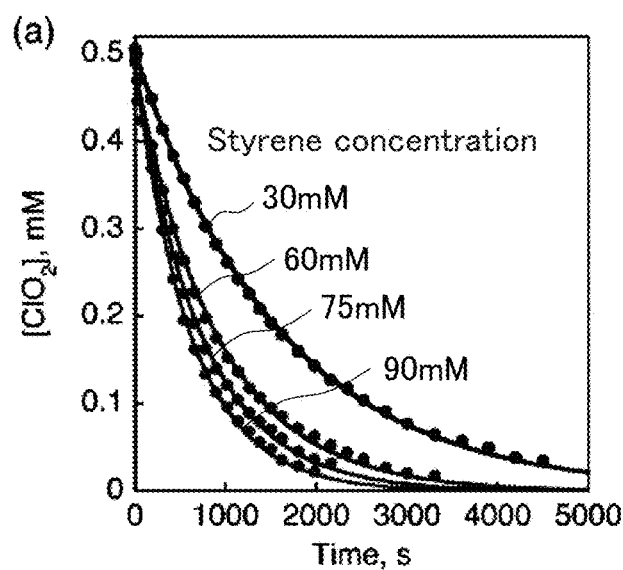
FIG. 8A shows a time profile of UV-Vis absorption at 358 nm in consumption of $Sc^{3+}(ClO_2 \cdot)$ in the presence of styrene (30 to 90 mM) in a $MeCN/H_2O$ (1:1 v/v) solution at 298 K.
Figure 8B:
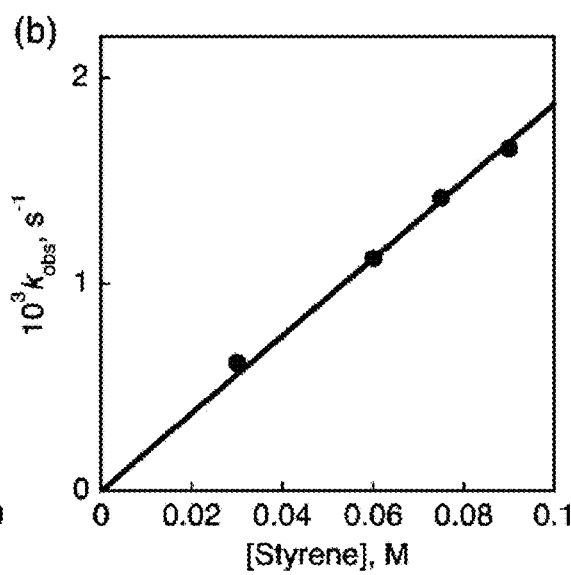
FIG. 8B shows a pseudo first-order rate-styrene concentration plot.

In the absence of a substrate, no decay of an absorbance at 358 nm based on ClO$_2$. generated from NaClO$_2$ using Sc(OTf)$_3$ was observed in MeCN at 298 K. FIG. 8A shows the time profile of UV-Vis absorption at 358 nm in consumption of Sc$^{3+}$(ClO$_2^-$) in the presence of styrene (30 to 90 mM) in a MeCN/H$_2$O (1:1 v/v) solution at 298 K. In FIG. 8A, the horizontal axis indicates a time (second) and the vertical axis indicates a ClO$_2$. concentration. FIG. 8B shows the pseudo first-order rate-styrene concentration plot. In the presence of an excessive amount of styrene, the rate of decay was in accordance with the pseudo first order (FIG. 8B). The pseudo first-order rate ($k_{obs}$) observed on the increase in dihydroxyl was increased linearly with the increase in a styrene concentration (FIG. 8B). The two-molecule rate constant of the consumption of ClO$_2$. and styrene was determined as $1.9 \times 10^{-2}$M$^{-1}$s$^{-1}$ (Reference, etc. 25). For clarifying the radical structure, electronic paramagnetic resonance (EPR) was performed. Pure ClO$_2$. was prepared by refluxing a MeCN solution containing NaClO$_2$ at 353 K for 1 hour. The EPR spectrum of the thus obtained pure ClO$_2$. was measured after being cooled to 298 K. As a result, a distinctive isotropic signal was observed with g=2.0151 (±0.0002) together with four hyperfine lines derived from an unpaired electron of a Cl nucleus (I=3/2 in $^{35}$Cl and $^{37}$Cl, each having the same type of magnetic moment of 0.821 and 0.683 ((a) of FIG. 9) (Reference, etc. 26). The G value was remarkably changed by addition of CF$_3$COOH (g=2.0106) and Sc(OTf)$_3$ (g=2.0103) ((b) and (c) of FIG. 9). The hyperfine coupling constant of ClO$_2$. was decreased in the presence of CF$_3$COOH (15.78 G) and Sc(OTf)$_3$ (15.56 G) (a(Cl)=16.26 G) (Reference, etc. 27). This shows that proton and Sc$^{3+}$ bind to ClO$_2$' to form H$^+$ClO$_2$. and Sc$^{3+}$ClO$_2$. as reaction intermediates for strongly dihydroxylating styrene (Reference, etc. 28).

Figure 10:
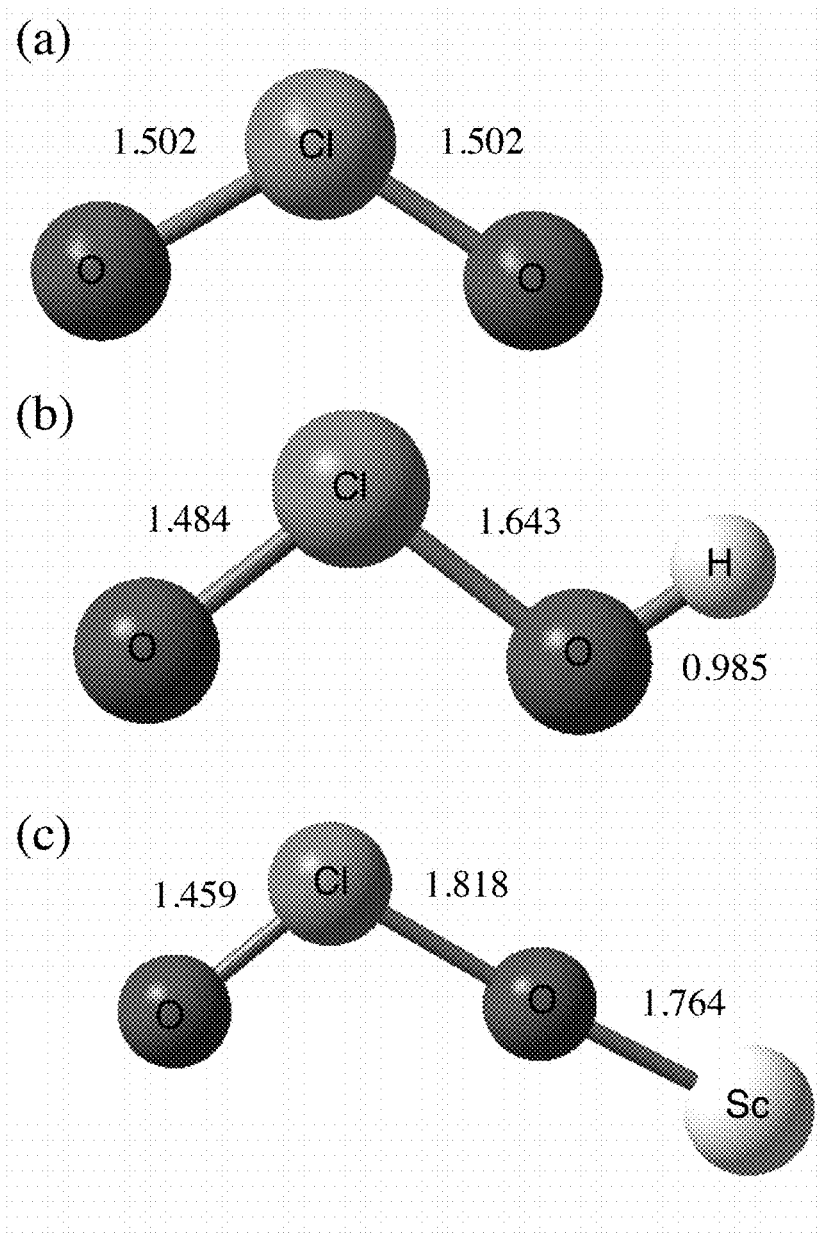
FIG. 10 shows the bond lengths (Å) of the DFT-optimized structures obtained by the theoretical calculation at the level of CAM-B3LYP/6-311+G(d, p).
Figure 15:
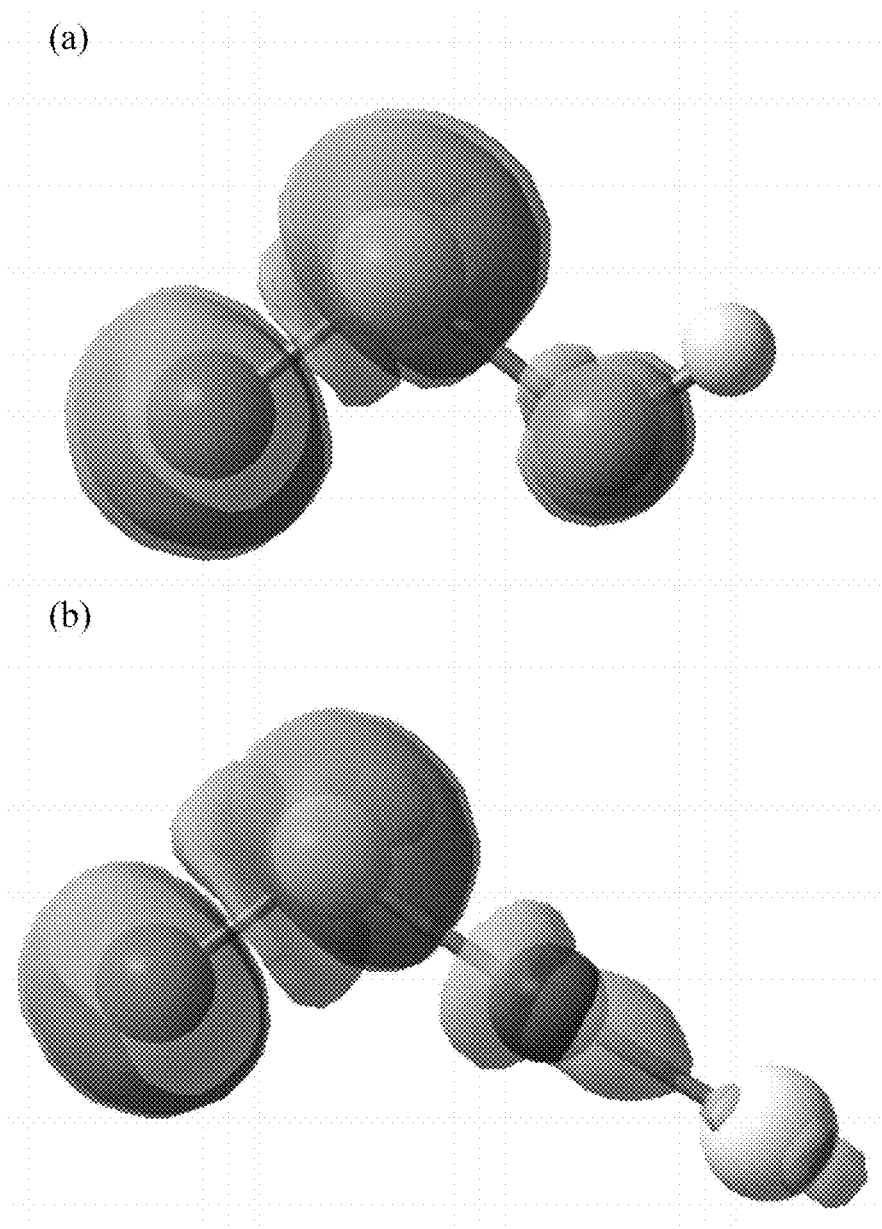
FIG. 15 is a diagram showing spin distributions calculated by DFT at the level of CAM-B3LYP/6-311+G (d, p).

As shown in FIG. 10, properties of ClO$_2$., H$^+$ClO$_2$., and Sc$^{3+}$ClO$_2$. were calculated on the basis of the density functional theory (DFT), and the reaction mechanism for dihydroxylation was predicted. The optimization of a structure was performed by the theoretical calculation at the level of DFT CAM-B3LYP/6-311+G(d, p). FIG. 10 shows the bond lengths (Å) of the DFT-optimized structures obtained by the theoretical calculation at the level of CAM-B3LYP/6-311+G(d, p). In FIG. 10, (a) shows the result obtained regarding ClO$_2$·; (b) shows the result obtained regarding H$^+$ClO$_2$·; and (c) shows the result obtained regarding Sc$^{3+}$ClO$_2$·. The bond length of the Cl—O double bond of ClO$_2$. was calculated as 1.502 Å ((a) of FIG. 10). The bond length of the Cl—O double bond of H$^+$ClO$_2$. was calculated as 1.643 Å ((b) of FIG. 10). (c) of FIG. 10 shows that, as compared to ClO$_2$., the bond strength of Sc$^{3+}$ClO$_2$. is also remarkably weakened (Cl—O: 1.818 Å). There is a possibility that the cleavage of the Cl—O bond may affect advantageously on generation of C1O. as a strong oxidizing agent in the presence of a substrate. FIG. 15 shows spin distributions obtained by the theoretical calculation at the level of CAM-B3LYP/6-311+G (d, p). In FIG. 15, (a) shows the spin distribution of H$^+$ClO$_2$. and (b) shows the spin distribution of Sc$^{3+}$ClO$_2$·.

On the basis of the above described results, the dihydroxylation mechanism of styrene by ClO$_2$. is shown in the following reaction formulae (2) to (5) and scheme 11. The disproportionation reaction of NaClO$_2$ is caused in the presence of H$^+$ or Sc$^{3+}$, thereby forming ClO$^-$ and ClO$_3^-$ [reaction formula (2)] (Reference, etc. 29). ClO$^-$ easily reacts with ClO$_2^-$ and protons, thereby generating Cl$_2$O$_2$ [reaction formula (3)]. Subsequently, Cl$_2$O$_2$ is reduced by ClO$_2^-$, thereby generating a reactive species ClO$_2$. [reaction formula (4)]. An overall stoichiometry is given by the reaction formula (5). ClO$_2$. is activated by binding to acids such as H$^+$ and Sc$^{3+}$. When ClO$_2$ binds to H$^+$, on the basis of the DFT calculation (see above), the Cl—O bond is not cleaved. The oxidization of styrene by H$^+$ proceeds by addition of ClO$_2$. to the styrene double bond. In contrast, the dihydroxylation of styrene by Sc$^{3+}$ is caused, as shown in scheme 11, by addition of ClO. and $Sc^{3+}$O. generated by homolytic fission of $Sc^{3+}$Cl—O bond of a $Sc^{3+}ClO_2$. complex to the styrene double bond. Subsequently, a scandium complex is hydrolyzed for obtaining a diol and $Sc^{3+}$ClO. as end products (scheme 11). $Sc^{3+}$ClO can be reused by adding a large excessive amount of $ClO_2^-$ to cause $Sc^{3+}ClO_2$. to be formed through oxidization. Also, ClO⁻ can be regenerated by $ClO_2^-$ as shown in reaction formula (2). Addition of ClO. formed by cleaving the Cl—O bond of $Sc^{3+}ClO_2$. to β carbon of styrene gave two isomers. When the β carbon-ClO bond is formed, as shown in scheme 11, a chlorine compound was obtained as a minor end product.

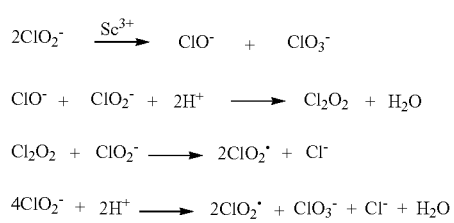

As described above, it was confirmed by the present example that $ClO_2$. is an effective dihydroxylation reagent for styrene as a Lewis acid in the presence of $Sc^{3+}$. The present invention can provide a unique dihydroxylation pathway of an olefin without causing hazardous wastes such as heavy metals.

REFERENCES, ETC

1. M. Schroeder, Chem. Rev., 1980, 80, 187-213.
2. (a) E. N. Jacobsen, I. Marko, W. S. Mungall, G. Schroeder and K. B. Sharpless, J. Am. Chem. Soc., 1988, 110, 1968-1970; and (b) S. G. Hentges and K. B. Sharpless, J. Am. Chem. Soc., 1980, 102, 4263-4265.
3. W. Yu, Y Mei, Y Kang, Z. Hua and Z. Jin, Org. Lett., 2004, 6, 3217-3219.
4. (a) A. J. DelMonte, J. Haller, K. N. Houk, K. B. Sharpless, D. A. Singleton, T. Strassner, and A. A. Thomas, J. Am. Chem. Soc., 1997, 119, 9907-9908; and (b) J. S. M. Wai, I. Marko, J. S. Svendsen, M. G. Finn, E. N. Jacobsen and K. B. Sharpless, J. Am. Chem. Soc., 1989, 111, 1123-1125.
5. (a) S. Kobayashi, M. Endo and S. Nagayama, J. Am. Chem. Soc., 1999, 121, 11229-11230; and (b) S. Kobayashi, T. Ishida and R. Akiyama, Org. Lett., 2001, 3, 2649-2652.
6. H. C. Kolb, P. G. Andersson and K. B. Sharpless, J. Am. Chem. Soc., 1994, 116, 1278-1291.
7. E. J. Corey and M. C. Noe, J. Am. Chem. Soc., 1996, 118, 11038-11053.
8. S. Y Jonsson, K. Faernegrdh and J.-E. Baeckvall, J. Am. Chem. Soc., 2001, 123, 1365-1371.
9. H. Dodgen and H. Taube, J. Am. Chem. Soc., 1949, 71, 2501-2504.
10. J. K. Leigh, J. Rajput, and D. E. Richardson, Inorg. Chem., 2014, 53, 6715-6727.
11. C. L. Latshaw, Tappi J., 1994, 163-166.
12. (a) J. J. Leddy, in Riegel's Handbook of Industrial Chemistry, 8th edn. Ed., J. A. Kent, Van Nostrand Reinhold Co. Inc, New York, 1983, pp. 212-235; and (b) I. Fabian, Coord. Chem. Rev., 2001, 216-217, 449-472.
13. M. J. Masschelen, J. Am. Works Assoc., 1984, 76, 70-76.
14. X.-L. Geng, Z. Wang, X.-Q. Li, and C. Zhang J. Org. Chem., 2005, 70, 9610-9613.
15. A. Jangam and D. E. Richardson, Tetrahedron Lett., 2010, 51, 6481-6484.
16. J. J. Kolar and B. O. Lindgren, Acta Chem. Scand. B, 1982, 36, 599-605.

Scheme 11

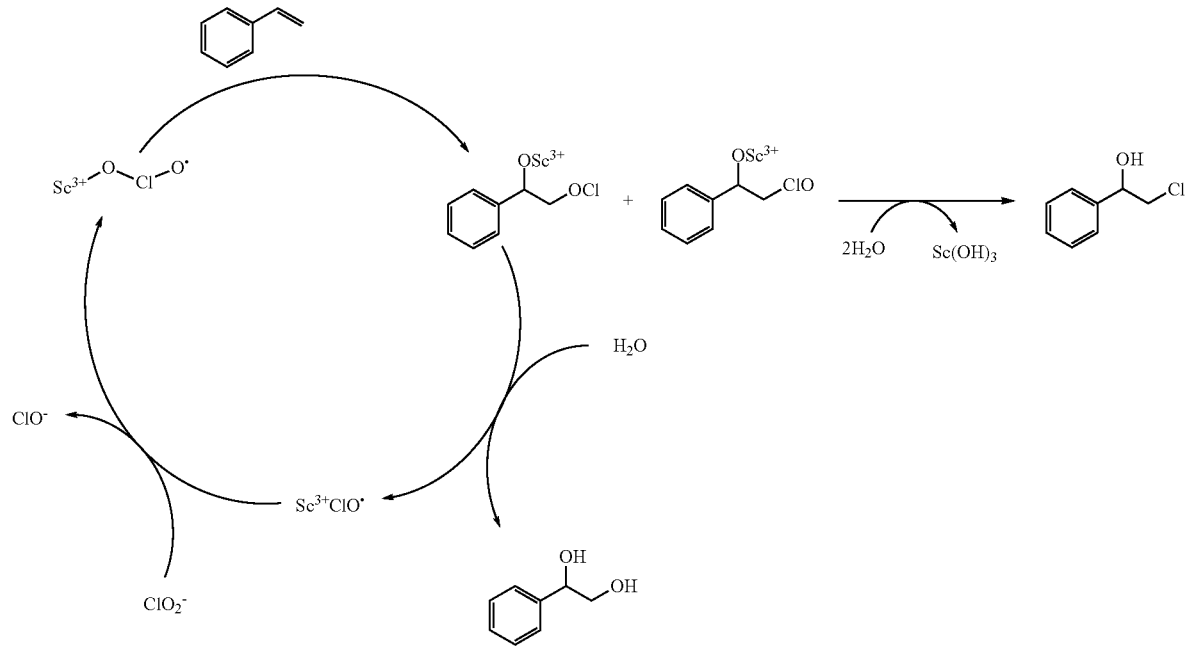

17. B. O. Lindgren, T. Nilsson, Acta Chem. Scand. B, 1974, 28, 847-852.
18. (a) S. Fukuzumi and K. Ohkubo, J. Am. Chem. Soc., 2002, 124, 10270-10271; and (b) S. Fukuzumi and K. Ohkubo, Chem.-Eur. J., 2000, 6, 4532-4535.
19. Epoxidation of styrene (66 mM) by $NaClO_2$ (200 mM) was checked in a $MeCN/H_2O$ mixture solution (4:1 v/v) at 333 K (Reference, etc. 14). The yield of styrene oxide was 44% and the conversion ratio of styrene was 61%.
20. E. V. Bakhmutova-Albert, D. W. Margerum, J. G. Auer and B. M. Applegate, Inorg. Chem., 2008, 47, 2205-2211.
21. As a result of measurement utilizing $^1HNMR$, styrene epoxide as an intermediate in reaction by $CF_3COOH$ or $Sc(OTf)_3$ was not observed.
22. C. Rav-Acha, E. Choushen (Goldstein) and S. Sarel, Helv. Chim. Acta, 1986, 69, 1728-1733.
23. There is a possibility that $ClO_2$. generated from acetic anhydride and $NaClO_2$ (Reference, etc. 22) is in the protonated form ($H^+ClO_2^-$) in a $ClO_2$. aqueous solution.
24. W. Masschelein, Ind. Eng. Chem. Prod. Res. Devel., 1967, 6, 137-142.
25. This numerical value is slightly greater than the value of the conversion of styrene to epoxide by $ClO_2$. ($1.17 \times 10^{-2}$ $M^{-1}$ $s^{-1}$) (Reference, etc. 10).
26. (a) T. Ozawa and T. Kwan, Chem. Pharm. Bull., 1983, 31, 2864-2867; and (b) T. Ozawa, T. Trends Org. Chem., 1991, 2, 51-58.
27. The calculated values of the spin distribution of $Sc^{3+}$ $ClO_2$ and $H^+ClO_2$. are shown in FIG. 15. According to this, each of Sc and H nuclei does not show a spin density. This means that the EPR spectrum does not show the hyperfine splitting derived from Sc (I=7/2) or H (I=1/2).
28. As to the bond between $Sc^{3+}$ and an oxo group of a metal oxo complex, see the following references:
(a) J. Chen, X. Wu, K. M. Davis, Y-M. Lee, M. S. Seo, K.-B. Cho, H. Yoon, Y J. Park, S. Fukuzumi, Y N. Pushkar and W. Nam, J. Am. Chem. Soc., 2013, 135, 6388-6391; (b) H. Yoon, Y-M. Lee, X. Wu, K.-B. Cho, Y N. Pushkar, W. Nam and S. Fukuzumi, J. Am. Chem. Soc., 2013, 135, 9186-9194; and (c) S. Fukuzumi, K. Ohkubo, Y-M. Lee and W. Nam, Chem.-Eur. J., 2015, 21, 17548-17559.
29. As to the disproportionation of a neutral radical by $Sc^{3+}$, see the following reference:
I. Nakanishi, T. Kawashima, K. Ohkubo, T. Waki, Y Uto, T. Kamada, T. Ozawa, K. Matsumoto and S. Fukuzumi, S. Chem. Commun., 2014, 50, 814-816.

Example 9

Figure 16:
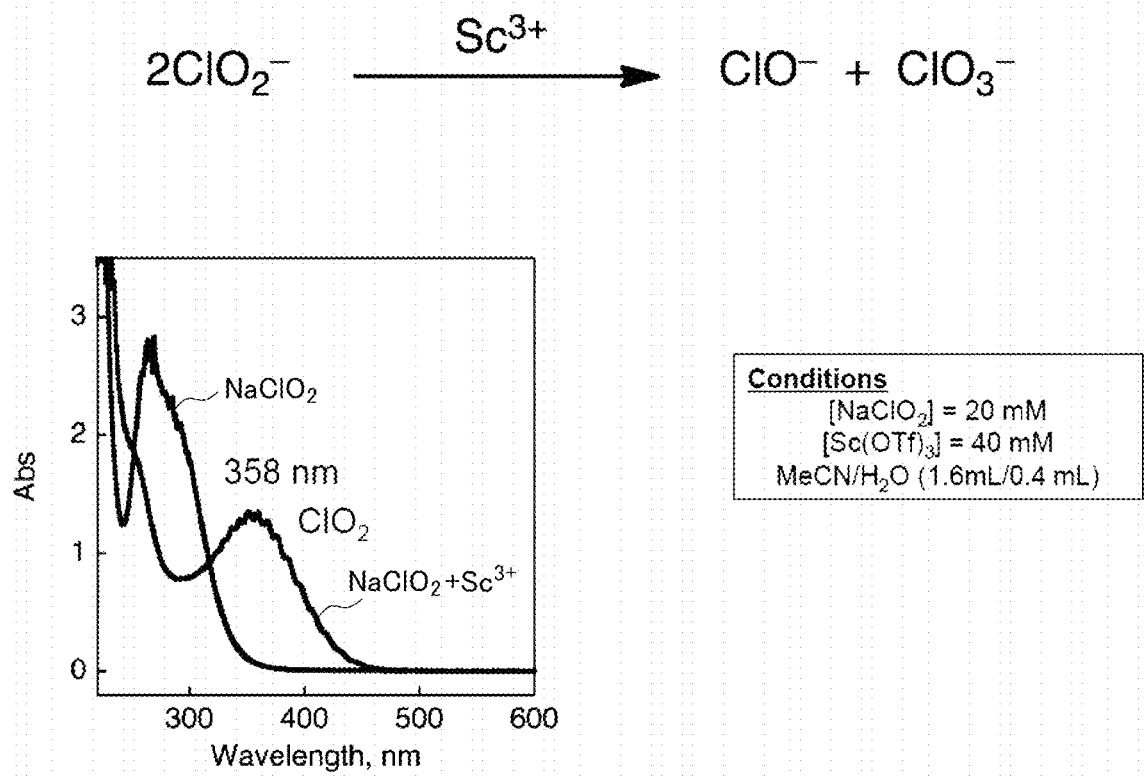
FIG. 16 shows an ultraviolet-visible absorption spectrum of $NaClO_2$ (20 mM) collected after mixing with $Sc(OTf)_3$ (40 mM) in an aqueous solution at 298 K.

The present example examined the acceleration effect of the disproportionation reaction of $NaClO_2$ by a Lewis acid.
As is confirmed in Example 8, degradation of sodium chlorite ($NaClO_2$) is not observed because it is very stable in a mixture solution of a neutral aqueous solution and acetonitrile. When $Sc(OTf)_3$ (40 mM) was added to this 20 mM solution, accompanying the decay of the absorption band of $NaClO_2$, an increase in absorption band characteristic of $ClO_2$ radicals ($ClO_2$) was observed at 358 nm immediately (FIG. 16). In FIG. 16, the horizontal axis indicates a wavelength (nm) and the vertical axis indicates an absorbance. The increase in this absorption band could be observed as a change over time by decreasing the concentration of $Sc(OTf)_3$ as confirmed in Example 8 (FIG. 6). By conducting similar studies on magnesium ions, lithium ions, and the like having lower Lewis acidities than scandium ions, the reaction rate constants of the respective ions were determined). It is known that Lewis acids catalyze various disproportionation reactions. In this reaction, it is considered that $ClO_2^-$ is disproportionated to $ClO^-$ and $ClO_3^-$ according to the reaction formula (2) of Example 8 by a similar mechanism. Thereafter, it is considered that the generated $ClO^-$ reacts with $ClO_2^-$, which is present in a large excessive amount, in the presence of an acid and gives $Cl_2O_2$ (reaction formula (3) of Example 8). Thereafter, it is considered that $Cl_2O_2$ further reacts with $ClO_2^-$ and gives $ClO_2$ radicals as active radical species (reaction formula (4) of Example 8).

Reference Example 1

Figure 17:
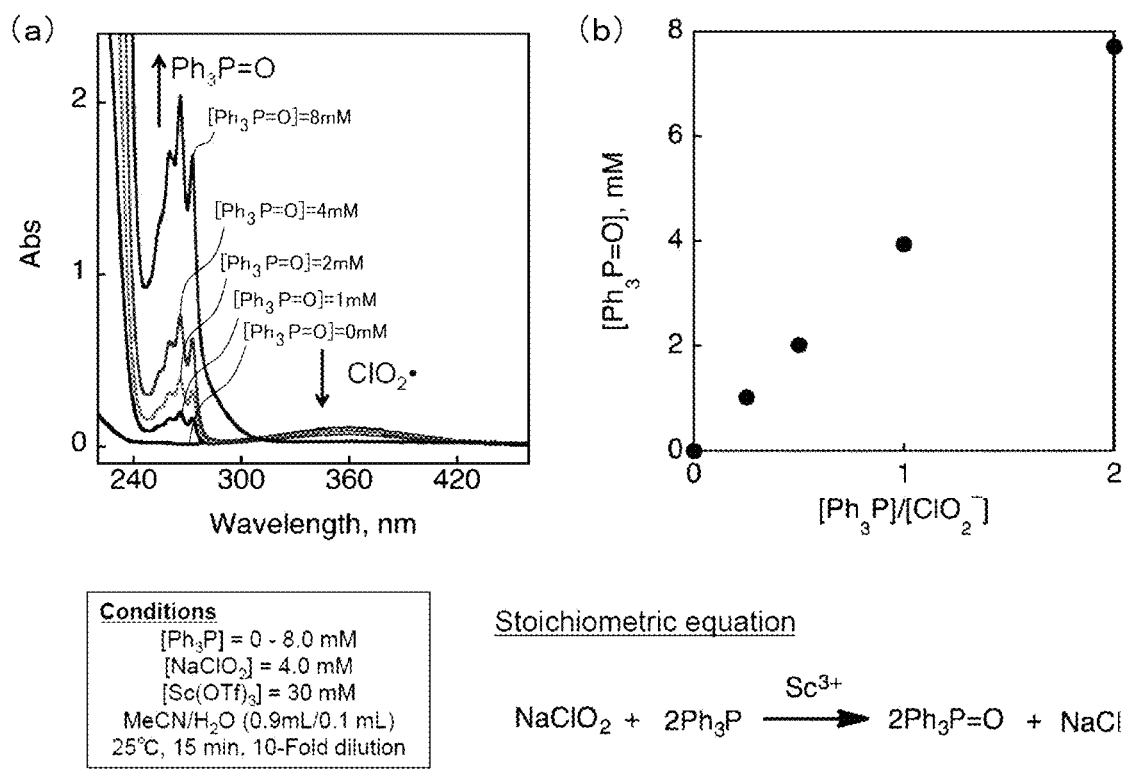
In FIG. 17, (a) is an ultraviolet-visible absorption spectrum showing the result of tracing an oxidation reaction of triphenylphosphine using $NaClO_2$ and scandium triflate; and (b) is a graph showing the relationship between an initial concentration of $Ph_3P$ and a concentration of generated $Ph_3P=O$ in the reaction shown in (a) of FIG. 17.

In the present reference example, the oxygenation reaction of a substrate by $NaClO_2$ using a Lewis acid was used for the oxygenation reaction from triphenylphosphine to triphenylphosphine oxide in order to examine whether it works. More specifically, the oxygenation reaction from triphenylphosphine to triphenylphosphine oxide by $NaClO_2$ was performed in the presence and the absence of scandium triflate$Sc(OTf)_3$, which is a Lewis acid, and in order to examine whether the Lewis acid promotes the reaction.
First, under the following conditions, in the presence or absence of $Sc(OTf)_3$, the reaction was performed at ordinary temperature and normal pressure (no light irradiation), and the reaction was traced by the ultraviolet-visible absorption spectrum. The ultraviolet-visible absorption spectrum shown in (a) of FIG. 19 shows the conversion of triphenylphosphine to triphenylphosphine oxide over time. In (a) of FIG. 19, the horizontal axis indicates a wavelength (nm) and the vertical axis indicates an absorbance. The graph shown in (b) of FIG. 19 shows the changes of a triphenylphosphine ($Ph_3P$) concentration over time in the presence and the absence of $Sc(OTf)_3$ ($Sc^{3+}$). In (b) of FIG. 19, the horizontal axis indicates a time (second) and the vertical axis indicates a triphenylphosphine ($Ph_3P$) concentration (mM). As shown in (b) of FIG. 19, while the reaction rate constant k calculated from the curve in the absence of $Sc^{3+}$ was $9.8 \times 10^{-4}$ $S^{-1}$, the reaction rate constant k calculated from the curve in the presence of $Sc^{3+}$ was increased to $1.7 \times 10^{-3}$ $S^{-1}$. Thus, it was confirmed that $Sc^{3+}$ (a Lewis acid) promoted the reaction.
[$Ph_3P$]=0.4 mM
[$NaClO_2$]=0.4 mM
$Sc(OTf)_3$=0 or 10 mM
0.12M acetate buffer, pH5.3
$MeCN/H_2O$ (4:6)
The reaction did not proceed at all by mixing triphenylphosphine and $NaClO_2$ (4.0 mM) in deoxygenated acetonitrile $MeCN/H_2O$ (0.9 ml/0.1 ml). By adding scandium triflate $Sc(OTf)_3$ (30 mM) thereto, oxygenated products were given efficiently. The initial concentration of triphenylphosphine was set to 1.0 mM, 2.0 mM, 4.0 mM, or 8.0 mM, and each reaction was performed at 25° C. for 15 minutes. The reaction was traced by monitoring the change in the ultraviolet-visible absorption spectrum ((a) of FIG. 17). In (a) of FIG. 17, the horizontal axis indicates a wavelength (nm) and the vertical axis indicates an absorbance. As can be seen from (a) of FIG. 17, it can be considered that a $CO_2$ radical, which is an active radical species, was generated by scandium ion $Sc^{3+}$, and $Ph_3P$ was oxygenated to $Ph_3P$=O. The stoichiometry is as represented by the following reaction formula (6), and it was confirmed that the reaction proceeds almost quantitatively ((b) of FIG. 17). In (b) of FIG. 17, the horizontal axis indicates the initial concentration of $Ph_3P$ and the vertical axis indicates the concentration of the generated $Ph_3P$=O.

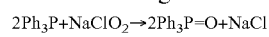

$$2Ph_3P + NaClO_2 \rightarrow 2Ph_3P=O + NaCl \qquad (6)$$

INDUSTRIAL APPLICABILITY

Industrial Applicability of First Aspect of Invention

As specifically described above, according to the production method of the first aspect of the present invention, using hydrocarbon or a derivative thereof as a raw material, an oxidation reaction product of the hydrocarbon or a derivative thereof can be produced efficiently. According to the first aspect of the present invention, for example, by a very simple method of simply performing light irradiation, hydrocarbon or a derivative thereof can be converted to an oxidation reaction product efficiently even under very mild conditions such as ordinary temperature and normal pressure. Furthermore, according to the first aspect of the present invention, for example, using hydrocarbon or a derivative thereof as a raw material, oxidation reaction products of great use in terms of industrial application, such as alcohol, carboxylic acid, ketone, phenol, and quinone can be produced efficiently. Because such oxidation reaction products conventionally could not be obtained efficiently using hydrocarbon as a raw material, it was very difficult to make effective use of hydrocarbon such as natural gas as a raw material. In contrast, the first aspect of the present invention can make effective use of hydrocarbon such as natural gas as a raw material. According to the first aspect of the present invention, compounds which had to be synthesized using petroleum as a raw material can be synthesized efficiently using natural gas as a raw material by a very simple method. Thus, the first aspect of the present invention can make a significant contribution to energy issues and the like. Furthermore, according to the first aspect of the present invention, for example, oxidation reaction products of the raw material (the hydrocarbon or a derivative thereof) can be obtained without using toxic heavy metal catalysts and the like. According to this, in addition to the fact that the reaction can be performed under very mild conditions such as ordinary temperature and normal pressure as described above, the oxidation reaction products can be obtained efficiently by a method with very small loads to the environment. As described above, the first aspect of the present invention is of great use in terms of industrial application.

Industrial Applicability of Second Aspect of Invention

As specifically described above, according to the production method of the second aspect of the present invention, using methane as a raw material, an oxidation reaction product of the methane can be produced efficiently. According to the second aspect of the present invention, for example, by a very simple method of simply performing light irradiation, methane can be converted to an oxidation reaction product efficiently even under very mild conditions such as ordinary temperature and normal pressure. Furthermore, according to the second aspect of the present invention, for example, using methane as a raw material, oxidation reaction products of great use in terms of industrial application, such as methanol, formic acid, formaldehyde, and methyl hydroperoxide can be produced efficiently. Because such oxidation reaction products conventionally could not be obtained efficiently using methane as a raw material, it was very difficult to make effective use of methane such as natural gas as a raw material. In contrast, the second aspect of the present invention can make effective use of methane such as natural gas as a raw material. According to the second aspect of the present invention, compounds which had to be synthesized using petroleum as a raw material can be synthesized efficiently using natural gas as a raw material by a very simple method. Thus, the second aspect of the present invention can make a significant contribution to energy issues and the like. Furthermore, according to the second aspect of the present invention, for example, oxidation reaction products of methane can be obtained without using toxic heavy metal catalysts and the like. According to this, in addition to the fact that the reaction can be performed under very mild conditions such as ordinary temperature and normal pressure as described above, the oxidation reaction products can be obtained efficiently by a method with very small loads to the environment. As described above, the second aspect of the present invention is of great use in terms of industrial application.

Industrial Applicability of Third Aspect of Invention

As specifically described above, according to the production method of the third aspect of the present invention, using ethane as a raw material, an oxidation reaction product of the ethane can be produced efficiently. According to the third aspect of the present invention, for example, by a very simple method of simply performing light irradiation, hydrocarbon or a derivative thereof can be converted to an oxidation reaction product efficiently even under very mild conditions such as ordinary temperature and normal pressure. Furthermore, according to the third aspect of the present invention, for example, using ethane as a raw material, oxidation reaction products of great use in terms of industrial application, such as ethanol, acetic acid, acetaldehyde, and ethyl hydroperoxide can be produced efficiently. Because such oxidation reaction products conventionally could not be obtained efficiently using hydrocarbon as a raw material, it was very difficult to make effective use of hydrocarbon such as natural gas as a raw material. In contrast, the third aspect of the present invention can make effective use of ethane contained in hydrocarbon such as natural gas as a raw material. According to the third aspect of the present invention, compounds which had to be synthesized using petroleum as a raw material can be synthesized efficiently using ethane contained in natural gas as a raw material by a very simple method. Thus, the third aspect of the present invention can make a significant contribution to energy issues and the like. Furthermore, according to the third aspect of the present invention, for example, oxidation reaction products of ethane can be obtained without using toxic heavy metal catalysts and the like. According to this, in addition to the fact that the reaction can be performed under very mild conditions such as ordinary temperature and normal pressure as described above, the oxidation reaction products can be obtained efficiently by a method with very small loads to the environment. As described above, the third aspect of the present invention is of great use in terms of industrial application.

Industrial Applicability of Fourth Aspect of Invention

As specifically described above, according to the production method of the fourth aspect of the present invention, using cyclohexane as a raw material, an oxidation reaction product of the cyclohexane can be produced efficiently. According to the fourth aspect of the present invention, for example, by a very simple method of simply performing light irradiation, cyclohexane can be converted to an oxidation reaction product efficiently even under very mild conditions such as ordinary temperature and normal pressure. Furthermore, according to the fourth aspect of the present invention, for example, using cyclohexane as a raw material, oxidation reaction products of great use in terms of industrial application, such as cyclohexanol, cyclohexanone, cyclohexane hydroperoxide, and ring-opening oxide (e.g., adipic acid) can be produced efficiently. Such oxidation reaction products conventionally could not be obtained efficiently using hydrocarbon as a raw material. In contrast, the fourth aspect of the present invention can make effective use of cyclohexane as a raw material. Thus, the fourth aspect of the present invention can make a significant contribution to energy issues and the like. Furthermore, according to the fourth aspect of the present invention, for example, oxidation reaction products of cyclohexane can be obtained without using toxic heavy metal catalysts and the like. According to this, in addition to the fact that the reaction can be performed under very mild conditions such as ordinary temperature and normal pressure as described above, the oxidation reaction products can be obtained efficiently by a method with very small loads to the environment. As described above, the fourth aspect of the present invention is of great use in terms of industrial application.

Industrial Applicability of Fifth Aspect of Invention

As specifically described above, according to the method for producing an oxidation reaction product of an olefin of the fifth aspect of the present invention, the reaction can be performed under mild conditions. Because the reaction can be performed under mild conditions, the reaction can be controlled easily at low cost. Thus, the method for producing an oxidation reaction product of an olefin of the fifth aspect of the present invention is applicable to a broad range of uses.

REFERENCE SIGNS LIST 1 organic layer (organic phase)
2 water layer (aqueous phase)

The invention claimed is:

1. A method for producing an oxidation reaction product, comprising the step of:
   irradiating a reaction system with light in the presence of a raw material and a chlorine dioxide radical, wherein
   the raw material is hydrocarbon or a derivative thereof,
   the reaction system is a reaction system containing an organic phase,
   the organic phase contains the raw material and the chlorine dioxide radical, and
   in the step of irradiating a reaction system with light, the raw material is oxidized by the light irradiation to generate an oxidation reaction product of the raw material.
2. The method according to claim 1, wherein
   the reaction system is a biphasic reaction system that further contains an aqueous phase.
3. The method according to claim 2, further comprising the step of:
   recovering the oxidation reaction product after the step of irradiating a reaction system with light, wherein
   the step of recovering the oxidation reaction product is a step of recovering the aqueous phase containing the oxidation reaction product from the reaction system.
4. The method according to claim 1, wherein
   the organic phase contains an organic solvent, and the organic solvent is a fluorous solvent.
5. The method according to claim 1 wherein
   the raw material is methane.
6. The method according to claim 5, wherein
   the oxidation reaction product includes at least one selected from the group consisting of methanol, formic acid, formaldehyde, and methyl hydroperoxide.
7. The method according to claim 1, wherein
   the raw material is ethane.
8. The method according to claim 7, wherein
   the oxidation reaction product includes at least one selected from the group consisting of ethanol, acetic acid, acetaldehyde, and ethyl hydroperoxide.
9. The method according to claim 1, wherein
   the raw material is cyclohexane.
10. The method according to claim 9, wherein
    the oxidation reaction product includes at least one selected from the group consisting of cyclohexanol, cyclohexanone, cyclohexane hydroperoxide, and ring-opening oxide.
11. The method according to claim 10, wherein
    the ring-opening oxide is adipic acid.
12. A method for producing an oxidation reaction product of an olefin, comprising the steps of:
    reacting at least one of a Lewis acid or a Brønsted acid with a radical source to generate a radical; and
    oxidizing an olefin using the radical as an oxidizing agent, wherein
    the Lewis acid has a Lewis acidity of 0.4 eV or more, and the Brønsted acid has an acid dissociation constant $pK_a$ of 5 or more.
13. The method according to claim 12, wherein
    the Lewis acid includes metal ions.
14. The method according to claim 12, wherein
    the Lewis acid is at least one selected from the group consisting of alkali earth metal ions, rare earth ions, $Mg^{2+}$, $Sc^{3+}$, $Li^+$, $Fe^{2+}$, $Fe^{3+}$, $Al^{3+}$, silicate ions, and borate ions.
15. The method according to claim 12, wherein
    the Lewis acid is at least one selected from the group consisting of $AlCl_3$, $AlMeCl_2$, $AlMe_2Cl$, $BF_3$, $BPh_3$, $BMe_3$, $TiCl_4$, $SiF_4$, and $SiCl_4$.
16. The method according to claim 12, wherein
    the radical source includes oxoacid.
17. The method according to claim 12, wherein
    the oxoacid includes a chlorite ion.
18. The method according to claim 12, wherein
    the olefin is an aromatic olefin.
19. The method according to claim 12, wherein
    the olefin is at least one selected from the group consisting of ethylene, propylene, styrene, and butadiene.
20. The method according to claim 12, wherein
    the oxidation reaction product is at least one of an epoxide or a diol.

* * * * *